(12) United States Patent
Tuttle et al.

(10) Patent No.: US 9,909,132 B2
(45) Date of Patent: Mar. 6, 2018

(54) FORMULATIONS AND METHODS FOR CONTROL OF WEEDY SPECIES

(71) Applicants: Chris Tuttle, Victoria (CA); Layne Woodfin, Port Alberni (CA)

(72) Inventors: Chris Tuttle, Victoria (CA); Layne Woodfin, Port Alberni (CA)

(*) Notice: Subject to any disclaimer, the term of this patent is extended or adjusted under 35 U.S.C. 154(b) by 0 days.

(21) Appl. No.: 14/783,341

(22) PCT Filed: Apr. 9, 2014

(86) PCT No.: PCT/IB2014/060565
§ 371 (c)(1),
(2) Date: Oct. 8, 2015

(87) PCT Pub. No.: WO2014/167514
PCT Pub. Date: Oct. 16, 2014

(65) Prior Publication Data
US 2016/0281099 A1    Sep. 29, 2016

Related U.S. Application Data

(60) Provisional application No. 61/810,024, filed on Apr. 9, 2013.

(51) Int. Cl.
*C12N 15/82* (2006.01)
*A01N 61/00* (2006.01)

(52) U.S. Cl.
CPC ......... *C12N 15/8218* (2013.01); *A01N 61/00* (2013.01); *C12N 15/8206* (2013.01); *C12N 15/8261* (2013.01)

(58) Field of Classification Search
CPC .................................... C12N 15/8218
USPC .......................................... 800/286
See application file for complete search history.

(56) References Cited

U.S. PATENT DOCUMENTS 7,741,086 B2 *  6/2010  Shi ........................... C12Q 1/26
                                                          435/183
2003/0113785 A1 *  6/2003  Zayed ................... C07K 14/415
                                                          435/6.12

* cited by examiner

*Primary Examiner* — Li Zheng
(74) *Attorney, Agent, or Firm* — Winstead PC

(57) ABSTRACT

A formulation is provided for application to a host plant to reduce, inhibit or impair one or more of growth and development of the host plant. A method of inhibiting growth plant growth and development is also provided as a means of controlling weedy species. The method comprises: selecting a suitable gene for growth suppression in a target plant; identifying an at least one target site accessible to base pairing in the suitable gene; identifying an at least one divergent site in the at least one target site; designing a construct complementary to the at least one divergent site; adding an at least one RNAi inducer to the construct; and delivering the construct to the target plant.

1 Claim, 11 Drawing Sheets

SEQUENCE LISTING

<160> NUMBER OF SEQ ID NOS: 71

<210> SEQ ID NO 1
<211> LENGTH: 21
<212> TYPE: RNA
<213> ORGANISM: Artificial Sequence
<220> FEATURE:
<223> OTHER INFORMATION: Actin 2 si-RNA-A strand 1

<400> SEQUENCE: 1
uuguagaaag ugugaugccu u                                        21

<210> SEQ ID NO 2
<211> LENGTH: 21
<212> TYPE: RNA
<213> ORGANISM: Artificial Sequence
<220> FEATURE:
<223> OTHER INFORMATION: Actin 2 si-RNA-B strand 1

<400> SEQUENCE: 2
uaauucauag uucuucucgu u                                        21

<210> SEQ ID NO 3
<211> LENGTH: 21
<212> TYPE: RNA
<213> ORGANISM: Artificial Sequence
<220> FEATURE:
<223> OTHER INFORMATION: CHI1 siRNA-A strand 1

<400> SEQUENCE: 3
uuccaguucc ucuaucuccu u                                        21

<210> SEQ ID NO 4
<211> LENGTH: 21
<212> TYPE: RNA
<213> ORGANISM: Artificial Sequence
<220> FEATURE:
<223> OTHER INFORMATION: CHI1 siRNA-B Strand 1

<400> SEQUENCE: 4
uugcagaaga agauguuccu u                                        21

<210> SEQ ID NO 5
<211> LENGTH: 21
<212> TYPE: RNA
<213> ORGANISM: Artificial Sequence
<220> FEATURE:
<223> OTHER INFORMATION: 18S siRNA-A Strand 1

<400> SEQUENCE: 5
uuuauuguca cuaccuccu u                                         21

<210> SEQ ID NO 6
<211> LENGTH: 21
<212> TYPE: RNA
<213> ORGANISM: Artificial Sequence
<220> FEATURE:
<223> OTHER INFORMATION: 18S siRNA-B Strand1

<400> SEQUENCE: 6
uuaucuaaua aaugcguccu u                                        21

<210> SEQ ID NO 7
<211> LENGTH: 23
<212> TYPE: DNA
<213> ORGANISM: Artificial Sequence

```
<220> FEATURE:
<223> OTHER INFORMATION: Actin 2 DNA encoding siRNA-A strand 1

<400> SEQUENCE: 7
aattgtagaa agtgtgatgc ctt                                              23

<210> SEQ ID NO 8
<211> LENGTH: 23
<212> TYPE: DNA
<213> ORGANISM: Artificial Sequence
<220> FEATURE:
<223> OTHER INFORMATION: Actin 2 DNA encoding siRNA-B strand 1

<400> SEQUENCE: 8
aataattcat agttcttctc gtt                                              23

<210> SEQ ID NO 9
<211> LENGTH: 23
<212> TYPE: DNA
<213> ORGANISM: Artificial Sequence
<220> FEATURE:
<223> OTHER INFORMATION: CHI1 DNA encoding siRNA-A strand 1

<400> SEQUENCE: 9
aattccagtt cctctatctc ctt                                              23

<210> SEQ ID NO 10
<211> LENGTH: 23
<212> TYPE: DNA
<213> ORGANISM: Artificial Sequence
<220> FEATURE:
<223> OTHER INFORMATION: CHI1 DNA encoding siRNA-b strand 1

<400> SEQUENCE: 10
aattgcagaa gaagatgttc ctt                                              23

<210> SEQ ID NO 11
<211> LENGTH: 23
<212> TYPE: DNA
<213> ORGANISM: Artificial Sequence
<220> FEATURE:
<223> OTHER INFORMATION: 18S DNA encoding siRNA-A strand 1

<400> SEQUENCE: 11
aatttattgt cactacctcc ctt                                              23

<210> SEQ ID NO 12
<211> LENGTH: 23
<212> TYPE: DNA
<213> ORGANISM: Artificial Sequence
<220> FEATURE:
<223> OTHER INFORMATION: 18S DNA encoding siRNA-b strand 1

<400> SEQUENCE: 12
aattatctaa taaatgcgtc ctt                                              23

<210> SEQ ID NO 13
<211> LENGTH: 492
<212> TYPE: DNA
<213> ORGANISM: Artificial Sequence
<220> FEATURE:
<223> OTHER INFORMATION: Synthetic construct targeting CHLI1 in A.
      thaliana, B. rapa, M. truncatula, Z. mays, N. tobacum

<400> SEQUENCE: 13
attccaacca gaagcagctg aatccaaaag aacatcaacc aaatgatcat ccaagagatt      60
```

```
aacttcatca acataaagaa tccctctatt agctttagcc tcgtaactca gcatccctaa      120
ccgtccctac ttgcgcgtgg ccctgaggtt aaagagagtg tgtgaatgga agggttggaa      180
gaaggagaag aaaggtaacg tgaaggaaga aatgcaatgg aagaaggata aactggcctc      240
gcactcttct ttgaatcaaa cttccctaca gttgtagatt ttccagttcc tctatctccc      300
ataatcataa aaacgagctc tttcctcaac tatcttcact ctcagctctg catctctcac      360
ggtccccact tagtgaagcc attttgttta gaattttttca gtgaagaaga agaagaagaa      420
ttttggggca atgggggag gaggaaggtt ttgaggaagg agaagagagt gaaggagaag       480
cccagattgc ag                                                          492

<210> SEQ ID NO 14
<211> LENGTH: 818
<212> TYPE: DNA
<213> ORGANISM: Artificial Sequence
<220> FEATURE:
<223> OTHER INFORMATION: Synthetic construct targeting mGFP5er, Acdl1,
      Acd2, Cat1, Cat2 and Lsd1 in B. rapa pekinensis

<400> SEQUENCE: 14
gtgcaactcg ctgatcatta tcaacaaaat actccaattg gcgatggccc cgcagagagg       60
ccgcttcgta aaatctcaac tgctttcaaa gaactagcag ccaccgtgag ctcgccgagt      120
cctgaagtct ccgtggctca gttctctcac gcttgctctc tcgtctcgcc tctctttggt      180
tgcctcggga tcgccttcaa gatattgagg caaactgtgt aaggaaagct ggtagtcata      240
ctagaaacct tttgagggta gagctaatgg ttgatctcat gtcgacgctg gaggatcgcc      300
tccactctca aagagagtgg tgggagaaga agagaaactg gagctggaaa gaagagataa      360
aagcttcaga aggaagagca tcaccaccaa ctctggtgct cctgtatgga acaacaactc      420
ctccatgacc gttggaccca gaggtcccca cgcgcttaaa ccaaacccta aatctcacat      480
tcaagaaaac tgaacctcac ttgtgctgac ttcctcagag ctccaggtgt tcaaactccg      540
gtcattcctg tccgctgcgc cgagaaagtt cctatcccta ccaaatccta cactggaata      600
agaacaaatg tatcctagag gagcaaccaa tgtgcgttgt gcgttatgtc acattgtcaa      660
catggttcct cttcatccta cccttacggt gcatcatctg ttaaatgcgc tgtttgccag      720
tttgttacta acgttaacaa aacttaccct taaatttatt tgcactactg gaaaactacc      780
tgttccatgg ccaacacttg tcactacttt ctcttatg                              818

<210> SEQ ID NO 15
<211> LENGTH: 742
<212> TYPE: DNA
<213> ORGANISM: Artificial Sequence
<220> FEATURE:
<223> OTHER INFORMATION: Synthetic construct targetingAtg5, Cat1, Jazh,
      MC2, Beclin1 in Nicotiana sylvestris

<400> SEQUENCE: 15
tctgaccagg tctcatcgtg tcgacggagg aagtgaagca cagaaatgga acaaaaataa       60
aaccttgggg tactctttga tcttctttgc aagaatgtaa tgaatatccc tgattacttt      120
cttcatatac cgtccgtcaa gtgccttcaa ttgctgaagc caaatcctaa atcccatacc      180
acaagattac aggcatagag tctcgaagca ttattaataa ctcattggcg atcaaattaa      240
gatgaatgtc agtttattaa aggaaaaagt aagaacaag aacaaaatca tttggcactt       300
ttcatactac aaccatcgac aaaattagct gctgccactg cttctttgac atgtaatacg      360
```

```
ggagactcac tgctatttca ttatttggct caaggcaaag gaattaggag atgaagtgga      420
tggatatgat gaaagctcct ccgccaccac ctaatcaata caatagcagc agtagtacta      480
ataaccttag ccaaagcaaa gaaatcagag aagaagaaga gcgaaaaagc ttgccttctt      540
ctccatacaa tccggccaaa gtttcaatat ccggatcatg acaccaata acaatactta       600 taggatcact atacagcaaa cgagatgcaa ttttagctaa gacagaagtt tcacaagctc      660
atttagagct gttaaagaag actaatgaag cagcaataga agaaacagag aagcaatctc      720
gagctcctga gacctggtcc tc                                              742

<210> SEQ ID NO 16
<211> LENGTH: 749
<212> TYPE: DNA
<213> ORGANISM: Artificial Sequence
<220> FEATURE:
<223> OTHER INFORMATION: Synthetic construct targeting Acd2, Bl-1, Llsl,
      NtTCTP, Beclinl in Nicotiana sylvestris

<400> SEQUENCE: 16
tctgaccagg tctcatcgtg tcgacatggt tgaacttata tcgactgtgg aggaaacaca      60
attagacgaa cagagacaat tgacagagga tgaaagttgg caaagaggga taaaataatt      120
aagaataaga caattgagat agaatggagt cttgcacatc gttcttcaat ttggagttac      180
gattctctta agaacttccg ccagatctct ccctttgttc aaactcatct caaaaatctg      240
gtatctctat cctttgctc aatttcatca cattacccaa tggcttcttc tctattatac       300
tccaccacca actcctcaaa ttctttcact tttcattctt ctctccctac taaaacccaa      360
tttgggtgct gatgaagatg aaggtggaga agcccaagaa gcatttaaaa agaacattga      420
atcagcaact aagttcctca tagtacttcc tgaactgttt cttaatgtta taagcagcag      480
tagtactaat aaccttagcc aaagcaaaga atcagagaa gaagaagagc gaaaaagctt      540
gccttcttct ccatacaatc cggccaaagt ttcaatatcc ggatcatgga caccaataac      600
aatacttata ggatcactat acagcaaact gtctgataaa cttgataagg acatacaagc      660
ctacgaagga gaaattgaag atagaacgga acgattaaca actttgccga ctttgcaaat      720
tcaactcgag ctcctgagac ctggtcctc                                       749

<210> SEQ ID NO 17
<211> LENGTH: 7883
<212> TYPE: DNA
<213> ORGANISM: Artificial Sequence
<220> FEATURE:
<223> OTHER INFORMATION: Synthetic construct consisting of CaMV35s
      promoter, TRV Ppk20 RNAI, ribozyme sequence and NOS terminator
<220> FEATURE:
<221> NAME/KEY: misc_feature
<222> LOCATION: (7256)..(7256)
<223> OTHER INFORMATION: n is a, c, g or t

<400> SEQUENCE: 17
aagcttgcat gcctgcaggt caacatggtg gagcacgaca ctctcgtcta ctccaagaat      60
atcaaagata cagtctcaga agaccagagg gctattgaga cttttcaaca aagggtaata      120
tcgggaaacc tcctcggatt ccattgccca gctatctgtc acttcatcga aggacagta       180 gaaaaggaag atggcttcta caaatgccat cattgcgata aaggaaaggc tatcgttcaa      240
gatgcctcta ccgacagtgg tcccaaagat ggacccccac ccacgaggaa catcgtggaa      300
aaagaagacg ttccaaccac gtcttcaaag caagtggatt gatgtgatgg tcaacatggt      360
ggagcacgac actctcgtct actccaagaa tatcaaagat acagtctcag aagaccagag      420
```

```
ggctattgag acttttcaac aaagggtaat atcgggaaac ctcctcggat tccattgccc      480
agctatctgt cacttcatcg aaaggacagt agaaaaggaa gatggcttct acaaatgcca      540
tcattgcgat aaaggaaagg ctatcgttca agatgcctct accgacagtg gtcccaaaga      600
tggaccccca cccacgagga acatcgtgga aaaagaagac gttccaacca cgtcttcaaa      660
gcaagtggat tgatgtgata ctccactga cgtaagggat gacgcacaat cccactatcc      720
ttcgcaagac ccttcctcta tataaggaag ttcatttcat ttggagagga taaacatttt     780
caatcctttg aacgcggtag aacgtgctaa ttggattttg gtgagaacgc ggtagaacgt      840
acttatcacc tacagttta ttttgttttt cttttggtt taatctatcc agcttagtac       900
cgagtggggg aaagtgactg gtgtgcctaa aaccttttct ttgatacttt gtaaaaatac      960
atacagatac aatggcgaac ggtaacttca agttgtctca attgctcaat gtggacgaga     1020
tgtctgctga gcagaggagt catttctttg acttgatgct gactaaacct gattgtgaga     1080
tcgggcaaat gatgcaagaa gttgttgttg ataaagtcga tgacatgatt agagaaagaa     1140
agactaaaga tccagtgatt gttcatgaag ttctttctca gaaggaacag aacaagttga     1200
tggaaattta tcctgaattc aatatcgtgt ttaaagacga caaaaacatg gttcatgggt     1260
ttgcggctgc tgagcgaaaa ctacaagctt tattgctttt agatagagtt cctgctctgc     1320
aagaggtgga tgcatcggt ggtcaatggt cgttttgggt aactagaggt gagaaaagga     1380
ttcattcctg ttgtccaaat ctagatattc gggatgatca gagagaaatt tctcgacaga     1440
tatttcttac tgctattggt gatcaagcta gaagtggtaa gagacagatg tcggagaatg     1500
agctgtggat gtatgaccaa tttcgtgaaa atattgctgc gcctaacgcg ttaggtgca      1560 ataatacata tcagggttgt acatgtaggg gtttttctga tggtaagaag aaaggcgcgc     1620
agtatgcgat agctcttcac agcctgtatg acttcaagtt gaaagacttg atggctacta     1680
tggttgagaa gaaaactaaa gtggttcatg ctgctatgct ttttgctcct gaaagtatgt     1740
tagtggacga aggtccatta ccttctgttg acggttacta catgaagaag aacgggaaga     1800
tctatttcgg ttttgagaaa gatccttcct tttcttacat tcatgactgg gaagagtaca     1860
agaagtatct actggggaag ccagtgagtt accaaggaa tgtgttctac ttcgaaccgt      1920
ggcaggtgag aggagacaca atgctttttt cgatctacag gatagctgga gttccgagga     1980
ggtctctatc atcgcaagag tactaccgaa gaatatat cagtagatgg gaaaacatgg       2040
ttgttgtccc aattttcgat ctggtcgaat caacgcgaga gttggtcaag aaagacctgt     2100
ttgtagagaa acaattcatg gacaagtgtt tggattacat agctaggtta tctgaccagc     2160
agctgaccat aagcaatgtt aaatcatact tgagttcaaa taattgggtc ttattcataa     2220
acggggcggc cgtgaagaac aagcaaagtg tagattctcg agatttacag ttgttggctc     2280
aaactttgct agtgaaggaa caagtggcga gacctgtcat gagggagttg cgtgaagcaa     2340
ttctgactga gacgaaacct atcacgtcat tgactgatgt gctgggttta atatcaagaa     2400
aactgtggaa gcagtttgct aacaagatcg cagtcggcgg attcgttggc atggttggta     2460
ctctaattgg attctatcca agaaggtac taacctgggc gaaggacaca ccaaatggtc       2520
cagaactatg ttacgagaac tcgcacaaaa ccaaggtgat agtatttctg agtgttgtgt     2580
atgccattgg aggaatcacg cttatgcgtc gagacatccg agatggactg gtgaaaaaac     2640
tatgtgatat gtttgatatc aaacgggggg cccatgtctt agacgttgag aatccgtgcc     2700
gctattatga aatcaacgat ttctttagca gtctgtattc ggcatctgag tccggtgaga     2760
```

```
ccgttttacc agatttatcc gaggtaaaag ccaagtctga taagctattg cagcagaaga      2820
aagaaatcgc tgacgagttt ctaagtgcaa aattctctaa ctattctggc agttcggtga      2880
gaacttctcc accatcggtg gtcggttcat ctcgaagcgg actgggtctg ttgttggaag      2940
acagtaacgt gctgacccaa gctagagttg gagtttcaag aaaggtagac gatgaggaga      3000
tcatggagca gtttctgagt ggtcttattg acactgaagc agaaattgac gaggttgttc      3060
cagccttttc agctgaatgt gaaagagggg aaacaagcgg tacaaaggtg ttgtgtaaac      3120
ctttaacgcc accaggattt gagaacgtgt tgccagctgt caaacctttg gtcagcaaag      3180
gaaaaacggt caaacgtgtc gattacttcc aagtgatggg aggtgagaga ttaccaaaaa      3240
ggccggttgt cagtggagac gattctgtgg acgctagaag agagtttctg tactacttag      3300
atgcggagag agtcgctcaa aatgatgaaa ttatgtctct gtatcgtgac tattcgagag      3360
gagttattcg aactggaggt cagaattacc cgcacggact gggagtgtgg gatgtggaga      3420
tgaagaactg gtgcatacgt ccagtggtca ctgaacatgc ttatgtgttc aaccagaca      3480 aacgtatgga tgattggtcg ggatacttag aagtggctgt tgggaacga ggtatgttgg      3540 tcaacgactt cgcggtcgaa aggatgagtg attatgtcat agtttgcgat cagacgtatc      3600
tttgcaataa caggttgatc ttggacaatt taagtgccct ggatctagga ccagttaact      3660
gttcttttga attagttgac ggtgtacctg gttgtggtaa gtcgacaatg attgtcaact      3720
cagctaatcc ttgtgtcgat gtggttctct ctactgggag agcagcaacc gacgacttga      3780
tcgagagatt cgcgagcaaa ggttttccat gcaaattgaa aggagagtg aagacggttg      3840 attcttttt gatgcattgt gttgatggtt ctttaaccgg agacgtgttg catttcgatg      3900
aagctctcat ggcccatgct ggtatggtgt acttttgcgc tcagatagct ggtgctaaac      3960
gatgtatctg tcaaggagat cagaatcaaa tttctttcaa gcctagggta tctcaagttg      4020
atttgaggtt ttctagtctg gtcggaaagt ttgacattgt tacagaaaaa agagaaactt      4080
acagaagtcc agcagatgtg gctgccgtat tgaacaagta ctatactgga gatgtcagaa      4140
cacataacgc gactgctaat tcgatgacgg tgaggaagat tgtgtctaaa gaacaggttt      4200
ctttgaagcc tggtgctcag tacataactt tccttcagtc tgagaagaag gagttggtaa      4260
atttgttggc attgaggaaa gtggcagcta aagtgagtac agtacacgag tcgcaaggag      4320
agacattcaa agatgtagtc ctagtcagga cgaaacctac ggatgactca atcgctagag      4380
gtcgggagta cttaatcgtg gcgttgtcgc gtcacacaca atcacttgtg tatgaaactg      4440
tgaaagagga cgatgtaagc aaagagatca gggaaagtgc cgcgcttacg aaggcggctt      4500
tggcaagatt ttttgttact gagaccgtct tatgacggtt tcggtctagg tttgatgtct      4560
ttagacatca tgaagggcct tgcgccgttc cagattcagg tacgattacg gacttggaga      4620
tgtggtacga cgctttgttt ccgggaaatt cgttaagaga ctcaagccta gacgggtatt      4680
tggtggcaac gactgattgc aatttgcgat tagacaatgt tacgatcaaa agtgaaaact      4740
ggaaagacaa gtttgctgaa aaagaaacgt ttctgaaacc ggttattcgt actgctatgc      4800
ctgacaaaag gaagactact cagttggaga gtttgttagc attgcagaaa aggaaccaag      4860
cggcacccga tctacaagaa aatgtgcacg caacagttct aatcgaagag acgatgaaga      4920
agttgaaatc tgttgtctac gatgtgggaa aaattcgggc tgatcctatt gtcaatagag      4980
ctcaaatgga gagatggtgg agaaatcaaa gcacagcggt acaggctaag gtagtagcag      5040
atgtgagaga gttacatgaa atagactatt cgtcttacat gtatatgatc aaatctgacg      5100
tgaaacctaa gactgatttta acaccgcaat ttgaatactc agctctacag actgttgtgt      5160
```

```
atcacgagaa gttgatcaac tcgttgttcg gtccaatttt caaagaaatt aatgaacgca    5220
agttggatgc tatgcaacca cattttgtgt tcaacacgag aatgacatcg agtgatttaa    5280
acgatcgagt gaagttctta aatacggaag cggcttacga ctttgttgag atagacatgt    5340
ctaaattcga caagtcggca aatcgcttcc atttacaact gcagctggag atttacaggt    5400
tatttgggct agatgagtgg gcggccttcc tttgggaggt gtcgcacact caaactactg    5460
tgagagatat tcaaaatggt atgatggcgc atatttggta ccaacaaaag agtggagatg    5520
ctgatactta taatgcaaat tcagatagaa cactgtgtgc actcttgtct gaattaccat    5580
tggagaaagc agtcatggtt acatatggag agatgactc actgattgcg tttcctagag     5640
gaacgcagtt tgttgatccg tgtccaaagt tggctactaa gtggaatttc gagtgcaaga    5700
tttttaagta cgatgtccca atgttttgtg ggaagttctt gcttaagacg tcatcgtgtt    5760
acgagttcgt gccagatccg gtaaaagttc tgacgaagtt ggggaaaaag agtataaagg    5820
atgtgcaaca tttagccgag atctacatct cgctgaatga ttccaataga gctcttggga    5880
actacatggt ggtatccaaa ctgtccgagt ctgtttcaga ccggtatttg tacaaaggtg    5940
attctgttca tgcgctttgt gcgctatgga agcatattaa gagttttaca gctctgtgta    6000
cattattccg agacgaaaac gataaggaat tgaacccggc taaggttgat tggaagaagg    6060
cacagagagc tgtgtcaaac ttttacgact ggtaatatgg aagacaagtc attggtcacc    6120
ttgaagaaga agactttcga agtctcaaaa ttctcaaatc taggggccat tgaattgttt    6180
gtggacggta ggaggaagag accgaagtat tttcacagaa gagagaaac tgtcctaaat     6240 catgttggtg gaagaagag tgaacacaag ttagacgttt ttgaccaaag ggattacaaa      6300
atgattaaat cttacgcgtt tctaaagata gtaggtgtac aactagttgt aacatcacat    6360
ctacctgcag atacgcctgg gttcattcaa atcgatctgt tggattcgag acttactgag    6420
aaaagaaaga gaggaaagac tattcagaga ttcaaagctc gagcttgcga taactgttca    6480
gttgcgcagt acaaggttga atacagtatt tccacacagg agaacgtact tgatgtctgg    6540
aaggtgggtt gtatttctga gggcgttccg gtctgtgacg gtacatacc tttcagtatc      6600 gaagtgtcgc taatatgggt tgctactgat tcgactaggc gcctcaatgt ggaagaactg    6660
aacagttcgg attacattga aggcgatttt accgatcaag aggttttcgg tgagttcatg    6720
tctttgaaac aagtggagat gaagacgatt gaggcgaagt acgatggtcc ttacagacca    6780
gctactacta gacctaagtc attattgtca agtgaagatg ttaagagagc gtctaataag    6840
aaaaactcgt cttaatgcat aaagaaattt attgtcaata tgacgtgtgt actcaagggt    6900
tgtgtgaatg aagtcactgt tcttggtcac gagacgtgta gtatcggtca tgctaacaaa    6960
ttgcgaaagc aagttgctga catggttggt gtcacacgta ggtgtgcgga aaataattgt    7020
ggatggtttg tctgtgttgt tatcaatgat tttacttttg atgtgtataa ttgttgtggc    7080
cgtagtcacc ttgaaaagtg tcgtaaacgt gttgaaacaa gaaatcgaga atttggaaa     7140 caaattcgac gaaatcaagc tgaaaacatg tctgcgacag ctaaaaagtc tcataattcg    7200
aagacctcta agaagaaatt caaagaggac agagaatttg ggacaccaaa aagatnttaa    7260
gagatgatgt tcctttcggg attgatcgtt tgtttgcttt ttgatttat tttatattgt     7320 tatctgtttc tgtgtataga ctgtttgaga ttggcgcttg gccgactcat tgtcttacca    7380
taggggaacg gactttgttt gtgttgttat tttatttgta tttttattaaa attctcaatg    7440 atctgaaaag gcctcgaggc taagagatta ttggggggtg agtaagtact tttaaagtga    7500
```

| tgatggttac aaaggcaaaa ggggtaaaac ccctcgccta cgtaagcgtt attacgcccg | 7560 |
| tctgtactta tatcagtaca ctgacgagtc cctaaaggac gaaacgggcc cctcgaattt | 7620 |
| ccccgatggg cgttcaaaca tttggcaata aagtttctta agattgaatc ctgttgccgg | 7680 |
| tcttgcgatg attatcatat aatttctgtt gaattacgtt aagcatgtaa taattaacat | 7740 |
| gtaatgcatg acgttattta tgagatgggt ttttatgatt agagtcccgc aattatacat | 7800 |
| ttaatacgcg atagaaaaca aaatatagcg cgcaaactag gataaattat cgcgcgcggt | 7860 |
| gtcatctatg ttactagatc ggg | 7883 |

<210> SEQ ID NO 18
<211> LENGTH: 9663
<212> TYPE: DNA
<213> ORGANISM: Artificial Sequence
<220> FEATURE:
<223> OTHER INFORMATION: TRV RNA2-MCS for transcription in plant cells

<400> SEQUENCE: 18

| ataaaacatt gcacctatgg tgttgccctg gctggggtat gtcagtgatc gcagtagaat | 60 |
| gtactaattg acaagttgga gaatacggta gaacgtcctt atccaacaca gcctttatcc | 120 |
| ctctccctga cgaggttttt gtcagtgtaa tatttctttt tgaactatcc agcttagtac | 180 |
| cgtacgggaa agtgactggt gtgcttatct ttgaaatgtt actttgggtt tcggttcttt | 240 |
| aggttagtaa gaaagcactt gtcttctcat acaaaggaaa acctgagacg tatcgcttac | 300 |
| gaaagtagca atgaaagaaa ggtggtggtt ttaatcgcra ccgcaaaaac gatggggtcg | 360 |
| ttttaattaa cttctcctac gcaagcgtct aaacggacgt tggggttttg ctagtttctt | 420 |
| tagagaaaac tagctaagtc tttaatgtta tcattagaga tggcataaat ataatacttg | 480 |
| tgtctgctga taagatcatt ttaatttgga cgattagact tgttgaacta caggttactg | 540 |
| aatcacttgc gctaatcaac atgggagata tgtacgatga atcatttgac aagtcgggcg | 600 |
| gtcctgctga cttgatggac gattcttggg tggaatcagt ttcgtggaaa gatctgttga | 660 |
| agaagttaca cagcataaaa tttgcactac agtctggtag agatgagatc actgggttac | 720 |
| tagcggcact gaatagacag tgtccttatt caccatatga gcagtttcca gataagaagg | 780 |
| tgtatttcct tttagactca cgggctaaca gtgctcttgg tgtgattcag aacgcttcag | 840 |
| cgttcaagag cgagctgat gagaagaatg cagtggcggg tgttacaaat attcctgcga | 900 |
| atccaaacac aacggttacg acgaaccaag ggagtactac tactaccaag gcgaacactg | 960 |
| gctcgacttt ggaagaagac ttgtacactt attacaaatt cgatgatgcc tctacagctt | 1020 |
| tccacaaatc tctaacttcg ttagagaaca tggagttgaa gagttattac cgaaggaact | 1080 |
| ttgagaaagt attcgggatt aagtttggtg gagcagctgc tagttcatct gcaccgcctc | 1140 |
| cagcgagtgg aggtccgata cgtcctaatc cctagggatt taaggacgtg aactctgttg | 1200 |
| agatctctgt gaaattcaga gggtgggtga taccatattc actgatgcca ttagcgacat | 1260 |
| ctaaataggg ctaattgtga ctaatttgag ggaatttcct ttaccattga cgtcagtgtc | 1320 |
| gttggtagca tttgagtttc gcaatgcacg aattacttag gaagtggctt gacgacacta | 1380 |
| atgtgttatt gttagataat ggtttggtgg tcaaggtacg tagtagagtc ccacatattc | 1440 |
| gcacgtatga agtaattgga aagttgtcag ttttgataa ttcactggga gatgatacgc | 1500 |
| tgtttgaggg aaaagtagag aacgtatttg ttttttatgtt caggcggttc ttgtgtgtca | 1560 |
| acaaagatgg acattgttac tcaaggaagc acgatgagct ttattattac ggacgagtgg | 1620 |
| acttagattc tgtgagtaag gttaccgaat tctctctagaag gcctccatgg ggatccggta | 1680 |

```
ccgagctcac gcgtctcgag gcccgggcat gtcccgaaga cattaaacta cggttcttta   1740
agtagatccg tgtctgaagt tttaggttca atttaaacct acgagattga cattctcgac   1800
tgatcttgat tgatcggtaa gtcttttgta atttaatttt cttttgatt ttattttaaa    1860 ttgttatctg tttctgtgta tagactgttt gagatcggcg tttggccgac tcattgtctt   1920
accatagggg aacggacttt gtttgtgttg ttattttatt tgtattttat taaaattctc   1980
aacgatctga aaagcctcg cggctaagag attgttgggg ggtgagtaag tacttttaaa    2040
gtgatgatgg ttacaaaggc aaaaggggta aaaccccctcg cctacgtaag cgttattacg   2100
cccgtctgta cttatatcag tacactgacg agtccctaaa ggacgaaacg ggagaacgct   2160
agccaccacc accaccacca cgtgtgaatt acaggtgacc agctcgaatt tccccgatcg   2220
ttcaaacatt tggcaataaa gtttcttaag attgaatcct gttgccggtc ttgcgatgat   2280
tatcatataa tttctgttga attacgttaa gcatgtaata attaacatgt aatgcatgac   2340
gttatttatg agatgggttt ttatgattag agtcccgcaa ttatacattt aatacgcgat   2400
agaaaacaaa atatagcgcg caaactagga taaattatcg cgcgcggtgt catctatgtt   2460
actagatcgg gaattaaact atcagtgttt gacaggatat attggcgggt aaacctaaga   2520
gaaaagagcg tttattagaa taacggatat ttaaagggc gtgaaaaggt ttatccgttc    2580
gtccatttgt atgtgcatgc caaccacagg gttcccctcg ggatcaaagt actttgatcc   2640
aacccctccg ctgctatagt gcagtcggct tctgacgttc agtgcagccg tcttctgaaa   2700
acgacatgtc gcacaagtcc taagttacgc gacaggctgc cgccctgccc ttttcctggc   2760
gttttcttgt cgcgtgtttt agtcgcataa agtagaatac ttgcgactag aaccggagac   2820
attacgccat gaacaagagc gccgccgctg gcctgctggg ctatgcccgc gtcagcaccg   2880
acgaccagga cttgaccaac caacgggccg aactgcacgc ggccggctgc accaagctgt   2940
tttccgagaa gatcaccggc accaggcgcg accgcccgga gctggccagg atgcttgacc   3000
acctacgccc tggcgacgtt gtgacagtga ccaggctaga ccgcctggcc cgcagcaccc   3060
gcgacctact ggacattgcc gagcgcatcc aggaggccgg cgcgggcctg cgtagcctgg   3120
cagagccgtg ggccgacacc accacgccgg ccggccgcat ggtgttgacc gtgttcgccg   3180
gcattgccga gttcgagcgt tccctaatca tcgaccgcac ccggagcggg cgcgaggccg   3240
ccaaggcccg aggcgtgaag tttggccccc gccctaccct caccccggca cagatcgcgc   3300
acgcccgcga gctgatcgac caggaaggcc gcaccgtgaa agaggcggct gcactgcttg   3360
gcgtgcatcg ctcgaccctg taccgcgcac ttgagcgcag cgaggaagtg acgcccaccg   3420
aggccaggcg gcgcggtgcc ttccgtgagg acgcattgac cgaggccgac gccctggcgg   3480
ccgccgagaa tgaacgccaa gaggaacaag catgaaaccg caccaggacg gccaggacga   3540 accgttttc attaccgaag agatcgaggc ggagatgatc gcggccgggt acgtgttcga   3600 gccgccgcg cacgtctcaa ccgtgcgcct gcatgaaatc ctggccggtt tgtctgatgc   3660
caagctggcg gcctggccgg ccagcttggc cgctgaagaa accgagcgcc gccgtctaaa   3720
aaggtgatgt gtatttgagt aaaacagctt gcgtcatgcg gtcgctgcgt atatgatgcg   3780
atgagtaaat aaacaaatac gcaaggggaa cgcatgaagg ttatcgctgt acttaaccag   3840
aaaggcgggt caggcaagac gaccatcgca acccatctag cccgcgccct gcaactcgcc   3900
ggggccgatg ttctgttagt cgattccgat ccccagggca gtgcccgcga ttgggcggcc   3960
gtgcgggaag atcaaccgct aaccgttgtc ggcatcgacc gcccgacgat tgaccgcgac   4020
```

-continued

```
gtgaaggcca tcggccggcg cgacttcgta gtgatcgacg gagcgcccca ggcggcggac      4080
ttggctgtgt ccgcgatcaa ggcagccgac ttcgtgctga ttccggtgca gccaagccct      4140
tacgacatat gggccaccgc cgacctggtg gagctggtta agcagcgcat tgaggtcacg      4200
gatggaaggc tacaagcggc ctttgtcgtg tcgcggggcga tcaaaggcac gcgcatcggc     4260
ggtgaggttg ccgaggcgct ggccgggtac gagctgccca ttcttgagtc ccgtatcacg      4320
cagcgcgtga gctacccagg cactgccgcc gccggcacaa ccgttcttga atcagaaccc      4380
gagggcgacg ctgccgcga ggtccaggcg ctggccgctg aaattaaatc aaaactcatt       4440
tgagttaatg aggtaaagag aaaatgagca aaagcacaaa cacgctaagt gccggccgtc      4500
cgagcgcacg cagcagcaag gctgcaacgt tggccagcct ggcagacacg ccagccatga      4560
agcgggtcaa ctttcagttg ccggcggagg atcacaccaa gctgaagatg tacgcggtac      4620
gccaaggcaa gaccattacc gagctgctat ctgaatacat cgcgcagcta ccagagtaaa      4680
tgagcaaatg aataaatgag tagatgaatt ttagcggcta aaggaggcgg catggaaaat      4740
caagaacaac caggcaccga cgccgtggaa tgccccatgt gtggaggaac gggcggttgg      4800
ccaggcgtaa gcggctgggt tgtctgccgg ccctgcaatg gcactggaac ccccaagccc      4860
gaggaatcgg cgtgacggtc gcaaaccatc cggcccggta caaatcggcg cggcgctggg      4920
tgatgacctg gtggagaagt tgaaggccgc gcaggccgcc cagcggcaac gcatcgaggc      4980
agaagcacgc cccggtgaat cgtggcaagc ggccgctgat cgaatccgca agaatcccg       5040 gcaaccgccg gcagccggtg cgccgtcgat taggaagccg cccaagggcg acgagcaacc      5100
agattttttc gttccgatgc tctatgacgt gggcacccgc gatagtcgca gcatcatgga      5160
cgtggccgtt ttccgtctgt cgaagcgtga ccgacgagct ggcgaggtga tccgctacga      5220
gcttccagac gggcacgtag aggtttccgc agggccggcc ggcatggcca gtgtgtggga      5280
ttacgacctg gtactgatgg cggtttccca tctaaccgaa tccatgaacc gataccggga      5340
agggaaggga gacaagcccg gccgcgtgtt ccgtccacac gttgcggacg tactcaagtt      5400
ctgccggcga gccgatggcg gaaagcagaa agacgacctg gtagaaacct gcattcggtt      5460
aaacaccacg cacgttgcca tgcagcgtac gaagaaggcc aagaacggcc gcctggtgac      5520
ggtatccgag ggtgaagcct tgattagccg ctacaagatc gtaaagagcg aaaccgggcg      5580
gccggagtac atcgagatcg agctagctga ttggatgtac cgcgagatca cagaaggcaa      5640
gaacccggac gtgctgacgg ttcacccgga ttactttttg atcgatcccg gcatcggccg      5700
ttttctctac cgcctggcac gccgcgcgc aggcaaggca gaagccagat ggttgttcaa       5760
gacgatctac gaacgcagtg gcagcgccgg agagttcaag aagttctgtt tcaccgtgcg      5820
caagctgatc gggtcaaatg acctgccgga gtacgatttg aaggaggagg cggggcaggc      5880
tggcccgatc ctagtcatgc gctaccgcaa cctgatcgag ggcgaagcat ccgccggttc      5940
ctaatgtacg gagcagatgc tagggcaaat tgccctagca ggggaaaaag gtcgaaaagg      6000 tctcttttcct gtggatagca cgtacattgg gaacccaaag ccgtacattg ggaaccggaa      6060
cccgtacatt gggaacccaa agccgtacat gggaaccgg tcacacatgt aagtgactga      6120
tataaaagag aaaaaaggcg atttttccgc ctaaaactct ttaaaactta ttaaaactct      6180
taaaacccgc ctggcctgtg cataactgtc tggccagcgc acagccgaag agctgcaaaa      6240
agcgcctacc cttcggtcgc tgcgctccct acgccccgcc gcttcgcgtc ggcctatcgc      6300
ggccgctggc cgctcaaaaa tggctggcct acggccaggc aatctaccag ggcgcggaca      6360
agccgcgccg tcgccactcg accgccggcg cccacatcaa ggcaccctgc ctcgcgcgtt      6420
```

```
tcggtgatga cggtgaaaac ctctgacaca tgcagctccc ggagacggtc acagcttgtc    6480
tgtaagcgga tgccgggagc agacaagccc gtcaggcgc gtcagcgggt gttggcgggt    6540 gtcgggcgc agccatgacc cagtcacgta gcgatagcgg agtgtatact ggcttaacta    6600
tgcggcatca gagcagattg tactgagagt gcaccatatg cggtgtgaaa taccgcacag    6660
atgcgtaagg agaaaatacc gcatcaggcg ctcttccgct tcctcgctca ctgactcgct    6720
gcgctcggtc gttcggctgc ggcgagcggt atcagctcac tcaaaggcgg taatacggtt    6780
atccacagaa tcaggggata acgcaggaaa gaacatgtga gcaaaaggcc agcaaaaggc    6840
caggaaccgt aaaaaggccg cgttgctggc gtttttccat aggctccgcc ccctgacga    6900 gcatcacaaa aatcgacgct caagtcagag gtggcgaaac ccgacaggac tataaagata    6960
ccaggcgttt ccccctggaa gctccctcgt gcgctctcct gttccgaccc tgccgcttac    7020
cggatacctg tccgcctttc tcccttcggg aagcgtggcg ctttctcata gctcacgctg    7080
taggtatctc agttcggtgt aggtcgttcg ctccaagctg ggctgtgtgc acgaaccccc    7140
cgttcagccc gaccgctgcg ccttatccgg taactatcgt cttgagtcca acccggtaag    7200
acacgactta tcgccactgg cagcagccac tggtaacagg attagcagag cgaggtatgt    7260
aggcggtgct acagagttct tgaagtggtg gcctaactac ggctacacta aaggacagt    7320 atttggtatc tgcgctctgc tgaagccagt taccttcgga aaagagttg gtagctcttg    7380 atccggcaaa caaaccaccg ctggtagcgg tggtttttt gtttgcaagc agcagattac    7440
gcgcagaaaa aaggatctc aagaagatcc tttgatcttt tctacggggt ctgacgctca    7500
gtggaacgaa aactcacgtt aagggatttt ggtcatgcat tctaggtact aaaacaattc    7560
atccagtaaa atataatatt ttattttctc ccaatcaggc ttgatcccca gtaagtcaaa    7620
aaatagctcg acatactgtt cttccccgat atcctccctg atcgaccgga cgcagaaggc    7680
aatgtcatac cacttgtccg ccctgccgct ctcccaaga tcaataaagc cacttacttt    7740
gccatctttc acaaagatgt tgctgtctcc caggtcgccg tgggaaaaga caagttcctc    7800
ttcgggcttt tccgtctta aaaatcata cagctcgcgc ggatctttaa atggagtgtc    7860
ttcttcccag ttttcgcaat ccacatcggc cagatcgtta ttcagtaagt aatccaattc    7920
ggctaagcgg ctgtctaagc tattcgtata gggacaatcc gatatgtcga tggagtgaaa    7980
gagcctgatg cactccgcat acagctcgat aatcttttca gggctttgtt catcttcata    8040
ctcttccgag caaaggacgc catcggcctc actcatgagc agattgctcc agccatcatg    8100
ccgttcaaag tgcaggacct ttggaacagg cagctttcct tccagccata gcatcatgtc    8160
cttttcccgt tccacatcat aggtggtccc tttataccgg ctgtccgtca tttttaaata    8220
taggttttca ttttctccca ccagcttata taccttagca ggagacattc cttccgtatc    8280
ttttacgcag cggtattttt cgatcagttt tttcaattcc ggtgatattc tcattttagc    8340
catttattat ttccttcctc ttttctacag tatttaaaga taccccaaga agctaattat    8400
aacaagacga actccaattc actgttcctt gcattctaaa accttaaata ccagaaaaca    8460 gcttttcaa agttgttttc aaagttggcg tataacatag tatcgacgga gccgattttg    8520
aaaccgcggt gatcacaggc agcaacgctc tgtcatcgtt acaatcaaca tgctaccctc    8580
cgcgagatca tccgtgtttc aaacccggca gcttagttgc cgttcttccg aatagcatcg    8640
gtaacatgag caaagtctgc cgccttacaa cggctctccc gctgacgccg tcccggactg    8700
atgggctgcc tgtatcgagt ggtgattttg tgccgagctg ccggtcgggg agctgttggc    8760
```

| | |
|---|---|
| tggctggtgg caggatatat tgtggtgtaa acaaattgac gcttagacaa cttaataaca | 8820 |
| cattgcggac gtttttaatg tactgaatta acgccgaatt aattcctagg ccaccatgtt | 8880 |
| gggcccggcg cgccaagctt gcatgcctgc aggtcaacat ggtggagcac gacactctcg | 8940 |
| tctactccaa gaatatcaaa gatacagtct cagaagacca gagggctatt gagacttttc | 9000 |
| aacaaagggt aatatcggga aacctcctcg gattccattg cccagctatc tgtcacttca | 9060 |
| tcgaaaggac agtagaaaag gaagatggct tctacaaatg ccatcattgc gataaaggaa | 9120 |
| aggctatcgt tcaagatgcc tctaccgaca gtggtcccaa agatggaccc ccacccacga | 9180 |
| ggaacatcgt ggaaaaagaa gacgttccaa ccacgtcttc aaagcaagtg gattgatgtg | 9240 |
| atggtcaaca tggtggagca cgacactctc gtctactcca agaatatcaa agatacagtc | 9300 |
| tcagaagacc agagggctat tgagactttt caacaaaggg taatatcggg aaacctcctc | 9360 |
| ggattccatt gcccagctat ctgtcacttc atcgaaagga cagtagaaaa ggaagatggc | 9420 |
| ttctacaaat gccatcattg cgataaagga aggctatcg ttcaagatgc ctctaccgac | 9480 |
| agtggtccca agatggaccc ccacccacg aggaacatcg tggaaaaaga agacgttcca | 9540 |
| accacgtctt caaagcaagt ggattgatgt gatatctcca ctgacgtaag ggatgacgca | 9600 |
| caatcccact atccttcgca agaccctcc tctatataag gaagttcatt tcatttggag | 9660 |
| agg | 9663 |

<210> SEQ ID NO 19
<211> LENGTH: 7117
<212> TYPE: DNA
<213> ORGANISM: Artificial Sequence
<220> FEATURE:
<223> OTHER INFORMATION: Truncated T7 driven Tobacco Rattle Virus
      RNA1(T7-RNA1 inducer)

<400> SEQUENCE: 19

| | |
|---|---|
| taatacgact cactatagat aaaacatttc aatcctttga acgcggtaga acgtgctaat | 60 |
| tggattttgg tgagaacgcg gtagaacgta cttatcacct acagttttat tttgttttc | 120 |
| tttttggttt aatctatcca gcttagtacc gagtggggga aagtgactgg tgtgcctaaa | 180 |
| acctttctt tgatactttg taaaaataca tacagataca atggcgaacg gtaacttcaa | 240 |
| gttgtctcaa ttgctcaatg tggacgagat gtctgctgag cagaggagtc atttctttga | 300 |
| cttgatgctg actaaacctg attgtgagat cgggcaaatg atgcaaagag ttgttgttga | 360 |
| taaagtcgat gacatgatta gagaaagaaa gactaaagat ccagtgattg ttcatgaagt | 420 |
| tctttctcag aaggaacaga acaagttgat ggaaatttat cctgaattca atatcgtgtt | 480 |
| taaagacgac aaaaacatgg ttcatgggtt tgcggctgct gagcgaaaac tacaagcttt | 540 |
| attgctttta gatagagttc ctgctctgca agaggtggat gacatcggtg gtcaatggtc | 600 |
| gttttgggta actagaggtg agaaaaggat tcattcctgt tgtccaaatc tagatattcg | 660 |
| ggatgatcag agagaaattt ctcgacagat atttcttact gctattggtg atcaagctag | 720 |
| aagtggtaag agacagatgt cggagaatga gctgtggatg tatgaccaat tcgtgaaaaa | 780 |
| tattgctgcg cctaacgcgg ttaggtgcaa taatacatat cagggttgta catgtagggg | 840 |
| ttttctgat ggtaagaaga aaggcgcgca gtatgcgata gctcttcaca gcctgtatga | 900 |
| cttcaagttg aaagacttga tggctactat ggttgagaag aaaactaaag tggttcatgc | 960 |
| tgctatgctt tttgctcctg aaagtatgtt agtggacgaa ggtccattac cttctgttga | 1020 |
| cggttactac atgaagaaga acgggaagat ctatttcggt tttgagaaag atccttcctt | 1080 |

```
ttcttacatt catgactggg aagagtacaa gaagtatcta ctggggaagc cagtgagtta    1140
ccaagggaat gtgttctact tcgaaccgtg gcaggtgaga ggagacacaa tgcttttttc    1200
gatctacagg atagctggag ttccgaggag gtctctatca tcgcaagagt actaccgaag    1260
aatatatatc agtagatggg aaaacatggt tgttgtccca attttcgatc tggtcgaatc    1320
aacgcgagag ttggtcaaga aagacctgtt tgtagagaaa caattcatgg acaagtgttt    1380
ggattacata gctaggttat ctgaccagca gctgaccata agcaatgtta atcatactt    1440 gagttcaaat aattgggtct tattcataaa cggggcggcc gtgaagaaca agcaaagtgt    1500
agattctcga gatttacagt tgttggctca aactttgcta gtgaaggaac aagtggcgag    1560
acctgtcatg agggagttgc gtgaagcaat tctgactgag acgaaaccta tcacgtcatt    1620
gactgatgtg ctgggtttaa tatcaagaaa actgtggaag cagtttgcta acaagatcgc    1680
agtcggcgga ttcgttggca tggttggtac tctaattgga ttctatccaa agaaggtact    1740
aacctgggcg aaggacacac caaatggtcc agaactatgt tacgaaact cgcacaaaac    1800 caaggtgata gtatttctga gtgttgtgta tgccattgga ggaatcacgc ttatgcgtcg    1860
agacatccga gatggactgg tgaaaaaact atgtgatatg tttgatatca acgggggc    1920 ccatgtctta gacgttgaga atccgtgccg ctattatgaa atcaacgatt tctttagcag    1980
tctgtattcg gcatctgagt ccggtgagac cgttttacca gatttatccg aggtaaaagc    2040
caagtctgat aagctattgc agcagaagaa agaaatcgct gacgagtttc taagtgcaaa    2100
attctctaac tattctggca gttcggtgag aacttctcca ccatcggtgg tcggttcatc    2160
tcgaagcgga ctgggtctgt tgttggaaga cagtaacgtg ctgacccaag ctagagttgg    2220
agtttcaaga aaggtagacg atgaggagat catggagcag tttctgagtg gtcttattga    2280
cactgaagca gaaattgacg aggttgttcc agccttttca gctgaatgtg aaagagggga    2340
aacaagcggt acaaaggtgt tgtgtaaacc tttaacgcca ccaggatttg agaacgtgtt    2400
gccagctgtc aaacctttgg tcagcaaagg aaaaacggtc aaacgtgtcg attacttcca    2460
agtgatggga ggtgagagat taccaaaaag gccggttgtc agtggagacg attctgtgga    2520
cgctagaaga gagtttctgt actacttaga tgcggagaga gtcgctcaaa atgatgaaat    2580
tatgtctctg tatcgtgact attcgagagg agttattcga actggaggtc agaattaccc    2640
gcacggactg ggagtgtggg atgtggagat gaagaactgg tgcatacgtc cagtggtcac    2700
tgaacatgct tatgtgttcc aaccagacaa acgtatggat gattggtcgg atacttaga    2760 agtggctgtt tgggaacgag gtatgttggt caacgacttc gcggtcgaaa ggatgagtga    2820
ttatgtcata gtttgcgatc agacgtatct ttgcaataac aggttgatct tggacaattt    2880
aagtgccctg gatctaggac cagttaactg ttcttttgaa ttagttgacg gtgtacctgg    2940
ttgtggtaag tcgacaatga ttgtcaactc agctaatcct tgtgtcgatg tggttctctc    3000
tactgggaga gcagcaaccg acgacttgat cgagagattc gcgagcaaag gttttccatg    3060
caaattgaaa aggagagtga agacggttga ttcttttttg atgcattgtg ttgatggttc    3120
tttaaccgga gacgtgttgc atttcgatga agctctcatg gcccatgctg gtatggtgta    3180
cttttgcgct cagatagctg gtgctaaacg atgtatctgt caaggagatc agaatcaaat    3240 ttcttttcaag cctagggtat ctcaagttga tttgaggttt tctagtctgg tcggaaagtt    3300
tgacattgtt acagaaaaaa gagaaactta cagaagtcca gcagatgtgg ctgccgtatt    3360
gaacaagtac tatactggag atgtcagaac acataacgcg actgctaatt cgatgacggt    3420
gaggaagatt gtgtctaaag aacaggtttc tttgaagcct ggtgctcagt acataacttt    3480
```

```
ccttcagtct gagaagaagg agttggtaaa tttgttggca ttgaggaaag tggcagctaa    3540
agtgagtaca gtacacgagt cgcaaggaga gacattcaaa gatgtagtcc tagtcaggac    3600
gaaacctacg gatgactcaa tcgctagagg tcgggagtac ttaatcgtgg cgttgtcgcg    3660
tcacacacaa tcacttgtgt atgaaactgt gaaagaggac gatgtaagca agagatcag    3720 ggaaagtgcc gcgcttacga aggcggcttt ggcaagattt tttgttactg agaccgtctt    3780
atgacggttt cggtctaggt ttgatgtctt tagacatcat gaagggcctt gcgccgttcc    3840
agattcaggt acgattacgg acttggagat gtggtacgac gctttgtttc cgggaaattc    3900
gttaagagac tcaagcctag acgggtattt ggtggcaacg actgattgca atttgcgatt    3960
agacaatgtt acgatcaaaa gtggaaactg gaaagacaag tttgctgaaa agaaacgtt    4020 tctgaaaccg gttattcgta ctgctatgcc tgacaaaagg aagactactc agttggagag    4080
tttgttagca ttgcagaaaa ggaaccaagc ggcacccgat ctacaagaaa atgtgcacgc    4140
aacagttcta atcgaagaga cgatgaagaa gttgaaatct gttgtctacg atgtgggaaa    4200
aattcgggct gatcctattg tcaatagagc tcaaatggag agatggtgga gaaatcaaag    4260
cacagcggta caggctaagg tagtagcaga tgtgagagag ttacatgaaa tagactattc    4320
gtcttacatg tatatgatca aatctgacgt gaaacctaag actgatttaa caccgcaatt    4380
tgaatactca gctctacaga ctgttgtgta tcacgagaag ttgatcaact cgttgttcgg    4440
tccaattttc aaagaaatta atgaacgcaa gttggatgct atgcaaccac attttgtgtt    4500
caacacgaga atgacatcga gtgatttaaa cgatcgagtg aagttcttaa atacggaagc    4560
ggcttacgac tttgttgaga tagacatgtc taaattcgac aagtcggcaa atcgcttcca    4620
tttacaactg cagctggaga tttacaggtt atttgggcta gatgagtggg cggccttcct    4680
ttgggaggtg tcgcacactc aaactactgt gagagatatt caaaatggta tgatggcgca    4740
tatttggtac caacaaaaga gtggagatgc tgatacttat aatgcaaatt cagatagaac    4800
actgtgtgca ctcttgtctg aattaccatt ggagaaagca gtcatggtta catatggagg    4860
agatgactca ctgattgcgt ttcctagagg aacgcagttt gttgatccgt gtccaaagtt    4920
ggctactaag tggaatttcg agtgcaagat ttttaagtac gatgtcccaa tgttttgtgg    4980
gaagttcttg cttaagacgt catcgtgtta cgagttcgtg ccagatccgg taaaagttct    5040
gacgaagttg gggaaaaaga gtataaagga tgtgcaacat ttagccgaga tctacatctc    5100
gctgaatgat tccaatagag ctcttgggaa ctacatggtg gtatccaaac tgtccgagtc    5160
tgtttcagac cggtatttgt acaaaggtga ttctgttcat gcgctttgtg cgctatggaa    5220
gcatattaag agttttacag ctctgtgtac attattccga gacgaaaacg ataaggaatt    5280
gaacccggct aaggttgatt ggaagaaggc acagagagct gtgtcaaact tttacgactg    5340
gtaatatgga agacaagtca ttggtcacct tgaagaagaa gactttcgaa gtctcaaaat    5400
tctcaaatct aggggccatt gaattgtttg tggacggtag gaggaagaga ccgaagtatt    5460
ttcacagaag aagagaaact gtcctaaatc atgttggtgg gaagaagagt gaacacaagt    5520
tagacgtttt tgaccaaagg gattacaaaa tgattaaatc ttacgcgttt ctaaagatag    5580
taggtgtaca actagttgta acatcacatc tacctgcaga tacgcctggg ttcattcaaa    5640
tcgatctgtt ggattcgaga cttactgaga aaagaaagag aggaaagact attcagagat    5700
tcaaagctcg agcttgcgat aactgttcag ttgcgcagta caaggttgaa tacagtattt    5760
ccacacagga gaacgtactt gatgtctgga aggtgggttg tatttctgag ggcgttccgg    5820
```

```
tctgtgacgg tacataccct ttcagtatcg aagtgtcgct aatatgggtt gctactgatt    5880
cgactaggcg cctcaatgtg gaagaactga acagttcgga ttacattgaa ggcgatttta    5940
ccgatcaaga ggttttcggt gagttcatgt ctttgaaaca agtggagatg aagacgattg    6000
aggcgaagta cgatggtcct tacagaccag ctactactag acctaagtca ttattgtcaa    6060
gtgaagatgt taagagagcg tctaataaga aaaactcgtc ttaatgcata aagaaattta    6120
ttgtcaatat gacgtgtgta ctcaagggtt gtgtgaatga agtcactgtt cttggtcacg    6180
agacgtgtag tatcggtcat gctaacaaat tgcgaaagca agttgctgac atggttggtg    6240
tcacacgtag gtgtgcggaa aataattgtg gatggtttgt ctgtgttgtt atcaatgatt    6300
ttacttttga tgtgtataat tgttgtggcc gtagtcacct tgaaaagtgt cgtaaacgtg    6360
ttgaaacaag aaatcgagaa atttggaaac aaattcgacg aaatcaagct gaaaacatgt    6420
ctgcgacagc taaaaagtct cataattcga agacctctaa gaagaaattc aaagaggaca    6480
gagaatttgg gacaccaaaa agattttttaa gagatgatgt tcctttcggg attgatcgtt    6540
tgtttgcttt ttgatttttat tttatattgt tatctgtttc tgtgtataga ctgtttgaga    6600
ttggcgcttg gccgactcat tgtcttacca taggggaacg gactttgttt gtgttgttat    6660
tttatttgta ttttattaaa attctcaatg atctgaaaag gcctcgaggc taagagatta    6720 ttgggggtg agtaagtact tttaaagtga tgatggttac aaaggcaaaa ggggtaaaac    6780
ccctcgccta cgtaagcgtt attacgcccg tctgtactta tatcagtaca ctgacgagtc    6840
cctaaaggac gaaacgggcc cgggcgttca acatttggc aataaagttt cttaagattg    6900
aatcctgttg ccggtcttgc gatgattatc atataatttc tgttgaatta cgttaagcat    6960
gtaataatta acatgtaatg catgacgtta tttatgagat gggtttttat gattagagtc    7020
ccgcaattat acatttaata cgcgatagaa acaaaaatat agcgcgcaaa ctaggataaa    7080
ttatcgcgcg cggtgtcatc tatgttacta gatcggg                              7117
```

<210> SEQ ID NO 20
<211> LENGTH: 10665
<212> TYPE: DNA
<213> ORGANISM: Artificial Sequence
<220> FEATURE:
<223> OTHER INFORMATION: Synthetic sequence consisting of optimized TRV
      coat protein driven by T7 promoter and a strong RBS and TRV Ppk20
      TNAI and ribozyme sequence driven by T7 promoter. All elements are
      in the pUC57 vector

<400> SEQUENCE: 20

```
gacgaaaggg cctcgtgata cgcctatttt tataggttaa tgtcatgata ataatggttt     60
cttagacgtc aggtggcact tttcggggaa atgtgcgcgg aacccctatt tgtttatttt    120
tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gttttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
```

```
gggatcatgt aactcgcctt gatcgttggg aaccggagct gaatgaagcc ataccaaacg      720
acgagcgtga caccacgatg cctgtagcaa tggcaacaac gttgcgcaaa ctattaactg      780
gcgaactact tactctagct tcccggcaac aattaataga ctggatggag gcggataaag      840
ttgcaggacc acttctgcgc tcggcccttc cggctggctg gtttattgct gataaatctg      900
gagccggtga gcgtgggtct cgcggtatca ttgcagcact ggggccagat ggtaagccct      960
cccgtatcgt agttatctac acgacgggga gtcaggcaac tatggatgaa cgaaatagac     1020
agatcgctga gataggtgcc tcactgatta agcattggta actgtcagac caagtttact     1080
catatatact ttagattgat ttaaaacttc atttttaatt taaaaggatc taggtgaaga     1140
tcctttttga taatctcatg accaaaatcc cttaacgtga gttttcgttc cactgagcgt     1200
cagaccccgt agaaaagatc aaaggatctt cttgagatcc ttttttttctg cgcgtaatct     1260
gctgcttgca aacaaaaaaa ccaccgctac cagcggtggt ttgtttgccg gatcaagagc     1320
taccaactct ttttccgaag gtaactggct tcagcagagc gcagatacca aatactgttc     1380
ttctagtgta gccgtagtta ggccaccact tcaagaactc tgtagcaccg cctacatacc     1440
tcgctctgct aatcctgtta ccagtggctg ctgccagtgg cgataagtcg tgtcttaccg     1500
ggttggactc aagacgatag ttaccggata aggcgcagcg tcgggctgaa cggggggtt     1560
cgtgcacaca gcccagcttg gagcgaacga cctacaccga actgagatac ctacagcgtg     1620
agctatgaga aagcgccacg cttcccgaag ggagaaaggc ggacaggtat ccggtaagcg     1680
gcagggtcgg aacaggagag cgcacgaggg agcttccagg gggaaacgcc tggtatcttt     1740
atagtcctgt cgggtttcgc cacctctgac ttgagcgtcg atttttgtga tgctcgtcag     1800
gggggcggag cctatggaaa aacgccagca acgcggcctt tttacggttc ctggcctttt     1860
gctggccttt tgctcacatg ttctttcctg cgttatcccc tgattctgtg ataaccgta      1920
ttaccgcctt tgagtgagct gataccgctc gccgcagccg aacgaccgag cgcagcgagt     1980
cagtgagcga ggaagcggaa gagcgcccaa tacgcaaacc gcctctcccc gcgcgttggc     2040
cgattcatta atgcagctgg cacgactaat acgactcact atagggagac cacaacggtt     2100
tccctctaga aataattttg tttaacttta agaaggagat ataccatggc ggacatgtac     2160
gacgagtcgt tcgataagtc cggtggcccg gccgacttga tggacgacag ctgggtggaa     2220
tccgtcagct ggaaagattt gctgaaaaag ctccattcta tcaagtttgc gttacaatcc     2280
ggtcgtgatg agattaccgg cctgctggcg ccctgaacc gccagtgccc gtacagcccg     2340
tatgagcaat tccagacaa aaaagtctat ttcctgctgg atagccgtgc taatagcgcc     2400
ctgggcgtta ttcagaatgc gtctgcgttt aagcgccgcg cggacgagaa gaacgcggtg     2460
gcgggcgtta ccaatatccc ggctaacccg aacaccacgg ttacgaccaa tcaaggtagc     2520
actaccacca ccaaggctaa caccggctcg accctggaag aggacttgta cacttactat     2580
aaatttgacg acgcgtcgac cgcattccac aaatcgctga cctccttgga aaatatggaa     2640
ctgaagtctt attaccgccg taacttcgag aaagtgtttg gtattaaatt tggtggcgca     2700
gccgcatcca gctcggcgcc gccaccggcg agcggtggcc cgattcgtcc gaatccttaa     2760
atgtcaggct cccttataca cagggtctca ctccgagctc gaatttcccc gatcgttcaa     2820
acatttggca ataaagtttc ttaagattga atcctgttgc cggtcttgcg atgattatca     2880
tataatttct gttgaattac gttaagcatg taataattaa catgtaatgc atgacgttat     2940
ttatgagatg ggtttttatg attagagtcc cgcaattata catttaatac gcgatagaaa     3000
acaaaatata gcgcgcaaac taggataaat tatcgcgcgc ggtgtcatct atgttactag     3060
```

```
atcggaggtt tcccgactgg aaagcgggca gtgagcgcaa cgcaattaat acgactcact    3120
atagataaaa catttcaatc ctttgaacgc ggtagaacgt gctaattgga ttttggtgag    3180
aacgcggtag aacgtactta tcacctacag ttttatttg ttttctttt tggtttaatc     3240
tatccagctt agtaccgagt gggggaaagt gactggtgtg cctaaaacct tttctttgat    3300
actttgtaaa aatacataca gatacaatgg cgaacggtaa cttcaagttg tctcaattgc    3360
tcaatgtgga cgagatgtct gctgagcaga ggagtcattt ctttgacttg atgctgacta    3420
aacctgattg tgagatcggg caaatgatgc aaagagttgt tgttgataaa gtcgatgaca    3480
tgattagaga aagaaagact aaagatccag tgattgttca tgaagttctt tctcagaagg    3540
aacagaacaa gttgatggaa atttatcctg aattcaatat cgtgtttaaa gacgacaaaa    3600
acatggttca tgggtttgcg gctgctgagc gaaaactaca agctttattg cttttagata    3660
gagttcctgc tctgcaagag gtggatgaca tcggtggtca atggtcgttt tgggtaacta    3720
gaggtgagaa aaggattcat tcctgttgtc caaatctaga tattcgggat gatcagagag    3780
aaatttctcg acagatattt cttactgcta ttggtgatca agctagaagt ggtaagagac    3840
agatgtcgga gaatgagctg tggatgtatg accaatttcg tgaaaatatt gctgcgccta    3900
acgcggttag gtgcaataat acatatcagg gttgtacatg taggggtttt tctgatggta    3960
agaagaaagg cgcgcagtat gcgatagctc ttcacagcct gtatgacttc aagttgaaag    4020
acttgatggc tactatggtt gagaagaaaa ctaaagtggt tcatgctgct atgcttttg     4080
ctcctgaaag tatgttagtg gacgaaggtc cattaccttc tgttgacggt tactacatga    4140
agaagaacgg gaagatctat ttcggttttg agaaagatcc ttccttttct tacattcatg    4200
actgggaaga gtacaagaag tatctactgg ggaagccagt gagttaccaa gggaatgtgt    4260
tctacttcga accgtggcag gtgagaggag acacaatgct ttttcgatc tacaggatag     4320
ctggagttcc gaggaggtct ctatcatcgc aagagtacta ccgaagaata tatatcagta    4380
gatgggaaaa catggttgtt gtcccaattt tcgatctggt cgaatcaacg cgagagttgg    4440
tcaagaaaga cctgtttta gagaaacaat tcatggacaa gtgtttggat tacatagcta     4500
ggttatctga ccagcagctg accataagca atgttaaatc atacttgagt tcaaataatt    4560
gggtcttatt cataaacggg gcggccgtga agaacaagca aagtgtagat tctcgagatt    4620
tacagttgtt ggctcaaact ttgctagtga aggaacaagt ggcgagacct gtcatgaggg    4680
agttgcgtga agcaattctg actgagacga aacctatcac gtcattgact gatgtgctgg    4740
gtttaatatc aagaaaactg tggaagcagt ttgctaacaa gatcgcagtc ggcggattcg    4800
ttggcatggt tggtactcta attggattct atccaaagaa ggtactaacc tgggcgaagg    4860
acacaccaaa tggtccagaa ctatgttacg agaactcgca caaaccaag gtgatagtat      4920
ttctgagtgt tgtgtatgcc attggaggaa tcacgcttat gcgtcgagac atccgagatg    4980
gactggtgaa aaaactatgt gatatgtttg atatcaaacg gggggcccat gtcttagacg    5040
ttgagaatcc gtgccgctat tatgaaatca acgatttctt tagcagtctg tattcggcat    5100
ctgagtccgg tgagaccgtt ttaccagatt tatccgaggt aaaagccaag tctgataagc    5160
tattgcagca aagaaagaa atcgctgacg agtttctaag tgcaaaattc tctaactatt    5220
ctggcagttc ggtgagaact ctccaccat cggtggtcgg ttcatctcga agcggactgg     5280
gtctgttgtt ggaagacagt aacgtgctga cccaagctag agttggagtt tcaagaaagg    5340
tagacgatga ggagatcatg gagcagtttc tgagtggtct tattgacact gaagcagaaa    5400
```

```
ttgacgaggt tgttccagcc tttttcagctg aatgtgaaag agggaaaaca agcggtacaa    5460
aggtgttgtg taaaccttta acgccaccag gatttgagaa cgtgttgcca gctgtcaaac    5520
ctttggtcag caaaggaaaa acggtcaaac gtgtcgatta cttccaagtg atgggaggtg    5580
agagattacc aaaaaggccg gttgtcagtg gagacgattc tgtggacgct agaagagagt    5640
ttctgtacta cttagatgcg gagagagtcg ctcaaaatga tgaaattatg tctctgtatc    5700
gtgactattc gagaggagtt attcgaactg gaggtcagaa ttacccgcac ggactgggag    5760
tgtgggatgt ggagatgaag aactggtgca tacgtccagt ggtcactgaa catgcttatg    5820
tgttccaacc agacaaacgt atggatgatt ggtcgggata cttagaagtg gctgtttggg    5880
aacgaggtat gttggtcaac gacttcgcgg tcgaaaggat gagtgattat gtcatagttt    5940
gcgatcagac gtatctttgc aataacaggt tgatcttgga caatttaagt gccctggatc    6000
taggaccagt taactgttct tttgaattag ttgacggtgt acctggttgt ggtaagtcga    6060
caatgattgt caactcagct aatccttgtg tcgatgtggt tctctctact gggagagcag    6120
caaccgacga cttgatcgag agattcgcga gcaaaggttt tccatgcaaa ttgaaaagga    6180
gagtgaagac ggttgattct mttgatgcat tgtgttgatg gttctttaac cggagacgtg    6240
ttgcatttcg atgaagctct catggcccat gctggtatgg tgtacttttg cgctcagata    6300
gctggtgcta aacgatgtat ctgtcaagga gatcagaatc aaatttcttt caagcctagg    6360
gtatctcaag ttgatttgag gttttctagt ctggtcggaa agtttgacat tgttacagaa    6420
aaaagagaaa cttacagaag tccagcagat gtggctgccg tattgaacaa gtactatact    6480
ggagatgtca gaacacataa cgcgactgct aattcgatga cggtgaggaa gattgtgtct    6540
aaagaacagg tttctttgaa gcctggtgct cagtacataa ctttccttca gtctgagaag    6600
aaggagttgg taaatttgtt ggcattgagg aaagtggcag ctaaagtgag tacagtacac    6660
gagtcgcaag gagagacatt caaagatgta gtcctagtca ggacgaaacc tacggatgac    6720
tcaatcgcta gaggtcggga gtacttaatc gtggcgttgt cgcgtcacac acaatcactt    6780
gtgtatgaaa ctgtgaaaga ggacgatgta agcaaagaga tcagggaaag tgccgcgctt    6840
acgaaggcgg ctttggcaag attttttgtt actgagaccg tcttatgacg gtttcggtct    6900
aggtttgatg tctttagaca tcatgaaggg ccttgcgccg ttccagattc aggtacgatt    6960
acggacttgg agatgtggta cgacgctttg tttccgggaa attcgttaag agactcaagc    7020
ctagacgggt atttggtggc aacgactgat tgcaatttgc gattagacaa tgttacgatc    7080
aaaagtggaa actggaaaga caagtttgct gaaaaagaaa cgtttctgaa accggttatt    7140
cgtactgcta tgcctgacaa aaggaagact actcagttgg agagtttgtt agcattgcag    7200
aaaaggaacc aagcggcacc cgatctacaa gaaaatgtgc acgcaacagt tctaatcgaa    7260
gagacgatga agaagttgaa atctgttgtc tacgatgtgg gaaaaattcg ggctgatcct    7320
attgtcaata gagctcaaat ggagagatgg tggagaaatc aaagcacagc ggtacaggct    7380
aaggtagtag cagatgtgag agagttacat gaaatagact attcgtctta catgtatatg    7440
atcaaatctg acgtgaaacc taagactgat ttaacaccgc aatttgaata ctcagctcta    7500
cagactgttg tgtatcacga gaagttgatc aactcgttgt tcggtccaat tttcaaagaa    7560
attaatgaac gcaagttgga tgctatgcaa ccacattttg tgttcaacac gagaatgaca    7620
tcgagtgatt taaacgatcg agtgaagttc ttaaatacgg aagcggctta cgactttgtt    7680
gagatagaca tgtctaaatt cgacaagtcg gcaaatcgct tccatttaca actgcagctg    7740
gagatttaca ggttatttgg gctagatgag tgggcggcct tccctttggga ggtgtcgcac    7800
```

```
actcaaacta ctgtgagaga tattcaaaat ggtatgatgg cgcatatttg gtaccaacaa    7860
aagagtggag atgctgatac ttataatgca aattcagata gaacactgtg tgcactcttg    7920
tctgaattac cattggagaa agcagtcatg gttacatatg gaggagatga ctcactgatt    7980
gcgtttccta gaggaacgca gtttgttgat ccgtgtccaa agttggctac taagtggaat    8040
ttcgagtgca agatttttaa gtacgatgtc ccaatgtttt gtgggaagtt cttgcttaag    8100
acgtcatcgt gttacgagtt cgtgccagat ccggtaaaag ttctgacgaa gttggggaaa    8160
aagagtataa aggatgtgca acatttagcc gagatctaca tctcgctgaa tgattccaat    8220
agagctcttg gaactacat ggtggtatcc aaactgtccg agtctgtttc agaccggtat    8280
ttgtacaaag gtgattctgt tcatgcgctt tgtgcgctat ggaagcatat aagagttttt    8340
acagctctgt gtacattatt ccgagacgaa acgataagg aattgaaccc ggctaaggtt    8400
gattggaaga aggcacagag agctgtgtca aacttttacg actggtaata tggaagacaa    8460
gtcattggtc accttgaaga agaagacttt cgaagtctca aaattctcaa atctaggggc    8520
cattgaattg tttgtggacg gtaggaggaa gagaccgaag tattttcaca gaagaagaga    8580
aactgtccta aatcatgttg gtgggaagaa gagtgaacac aagttagacg tttttgacca    8640
aagggattac aaaatgatta aatcttacgc gtttctaaag atagtaggtg tacaactagt    8700
tgtaacatca catctacctg cagatacgcc tgggttcatt caaatcgatc tgttggattc    8760
gagacttact gagaaaagaa agagaggaaa gactattcag agattcaaag ctcgagcttg    8820
cgataactgt tcagttgcgc agtacaaggt tgaatacagt atttccacac aggagaacgt    8880
acttgatgtc tggaaggtgg gttgtatttc tgagggcgtt ccggtctgtg acggtacata    8940 cccctttcagt atcgaagtgt cgctaatatg ggttgctact gattcgacta ggcgcctcaa    9000
tgtggaagaa ctgaacagtt cggattacat tgaaggcgat tttaccgatc aagaggtttt    9060
cggtgagttc atgtctttga aacaagtgga gatgaagacg attgaggcga agtacgatgg    9120
tccttacaga ccagctacta ctagacctaa gtcattattg tcaagtgaag atgttaagag    9180
agcgtctaat aagaaaaact cgtcttaatg cataaagaaa tttattgtca atatgacgtg    9240
tgtactcaag ggttgtgtga atgaagtcac tgttcttggt cacgagacgt gtagtatcgg    9300
tcatgctaac aaaattgcgaa agcaagttgc tgacatggtt ggtgtcacac gtaggtgtgc    9360
ggaaaataat tgtggatggt ttgtctgtgt tgttatcaat gattttactt ttgatgtgta    9420
taattgttgt ggccgtagtc accttgaaaa gtgtcgtaaa cgtgttgaaa caagaaatcg    9480
agaaatttgg aaacaaattc gacgaaatca agctgaaaac atgtctgcga cagctaaaaa    9540
gtctcataat tcgaagacct ctaagaagaa attcaaagag gacagagaat tgggacacc    9600 aaaaagattt taagagatg atgttccttt cgggattgat cgtttgtttg cttttttgatt    9660 ttatttata ttgttatctg tttctgtgta tagactgttt gagattggcg cttggccgac    9720
tcattgtctt accataggg aacggacttt gtttgtgttg ttatttatt tgtatttat     9780 taaaattctc aatgatctga aaaggcctcg aggctaagag attattgggg ggtgagtaag    9840
tacttttaaa gtgatgatgg ttacaaaggc aaaaggggta aaaccctcg cctacgtaag    9900 cgttattacg cccgtctgta cttatatcag tacactgacg agtccctaaa ggacgaaacg    9960
ggcccgggcg ttcaaacatt tggcaataaa gtttcttaag attgaatcct gttgccggtc   10020
ttgcgatgat tatcatataa tttctgttga attacgttaa gcatgtaata attaacatgt   10080
aatgcatgac gttatttatg agatgggttt ttatgattag agtcccgcaa ttatacattt   10140
```

```
aatacgcgat agaaaacaaa atatagcgcg caaactagga taaattatcg cgcgcggtgt    10200
catctatgtt actagatcgg ggtcgggatc cgatatctag atgcattcgc gaggtaccga    10260
gctcgaattc actggccgtc gttttacaac gtcgtgactg ggaaaaccct ggcgttaccc    10320
aacttaatcg ccttgcagca catccccctt tcgccagctg cgtaatagc gaagaggccc     10380 gcaccgatcg cccttcccaa cagttgcgca gcctgaatgg cgaatggcgc ctgatgcggt    10440
attttctcct tacgcatctg tgcggtattt cacaccgcat atggtgcact ctcagtacaa    10500
tctgctctga tgccgcatag ttaagccagc cccgacaccc gccaacaccc gctgacgcgc    10560
cctgacgggc ttgtctgctc ccggcatccg cttacagaca agctgtgacc gtctccggga    10620
gctgcatgtg tcagaggttt tcaccgtcat caccgaaacg cgcga                    10665
```

<210> SEQ ID NO 21
<211> LENGTH: 2484
<212> TYPE: DNA
<213> ORGANISM: Artificial Sequence
<220> FEATURE:
<223> OTHER INFORMATION: Synthetic T7-RNA2-MCS inducer sequence
<220> FEATURE:
<221> NAME/KEY: misc_feature
<222> LOCATION: (1972)..(1972)
<223> OTHER INFORMATION: n is a, c, g, or t

<400> SEQUENCE: 21

```
taatacgact cactatagga taaaacattg cacctatggt gttgccctgg ctggggtatg      60
tcagtgatcg cagtagaatg tactaattga caagttggag aatacggtag aacgtcctta    120
tccaacacag cctttatccc tctccctgac gaggttttg tcagtgtaat atttctttt      180 gaactatcca gcttagtacc gtacgggaaa gtgactggtg tgcttatctt gaaatgtta    240 ctttgggttt cggttcttta ggttagtaag aaagcacttg tcttctcata caaggaaaa    300 cctgagacgt atcgcttacg aaagtagcaa tgaaagaaag gtggtggttt taatcgctac    360
cgcaaaaacg atgggtcgt tttaattaac ttctcctacg caagcgtcta aacgacgtt      420 ggggttttgc tagtttcttt agagaaaact agctaagtct ttaatgttat cattagagat    480
ggcataaata taatacttgt gtctgctgat aagatcattt taatttggac gattagactt    540
gttgaactac aggttactga atcacttgcg ctaatcaaca tgggagatat gtacgatgaa    600
tcatttgaca agtcgggcgg tcctgctgac ttgatggacg attcttgggt ggaatcagtt    660
tcgtggaaag atctgttgaa gaagttacac agcataaaat ttgcactaca gtctggtaga    720
gatgagatca ctgggttact agcggcactg aatagacagt gtccttattc accatatgag    780
cagtttccag ataagaaggt gtatttcctt ttagactcac gggctaacag tgctcttggt    840
gtgattcaga acgcttcagc gttcaagaga cgagctgatg agaagaatgc agtggcgggt    900
gttacaaata ttcctgcgaa tccaaacaca acggttacga cgaaccaagg gagtactact    960
actaccaagg cgaacactgg ctcgactttg gaagaagact tgtacactta ttacaaattc   1020
gatgatgcct ctacagcttt ccacaaatct ctaacttcgt tagagaacat ggagttgaag   1080
agttattacc gaaggaactt tgagaaagta ttcgggatta gtttggtgg agcagctgct    1140 agttcatctg caccgcctcc agcgagtgga ggtccgatac gtcctaatcc ctagggattt   1200
aaggacgtga actctgttga gatctctgtg aaattcagag ggtgggtgat accatattca   1260
ctgatgccat tagcgacatc taaataggc taattgtgac taatttgagg gaatttcctt    1320
taccattgac gtcagtgtcg ttggtagcat ttgagtttcg caatgcacga attacttagg   1380
aagtggcttg acgacactaa tgtgttattg ttagataatg gtttggtggt caaggtacgt   1440
```

```
agtagagtcc cacatattcg cacgtatgaa gtaattggaa agttgtcagt ttttgataat      1500
tcactgggag atgatacgct gtttgaggga aaagtagaga acgtatttgt ttttatgttc      1560
aggcggttct tgtgtgtcaa caaagatgga cattgttact caaggaagca cgatgagctt      1620
tattattacg gacgagtgga cttagattct gtgagtaagg ttaccgaatt ctctagaagg      1680
cctccatggg gatccggtac cgagctcacg cgtctcgagg cccgggcatg tcccgaagac      1740
attaaactac ggttctttaa gtagatccgt gtctgaagtt ttaggttcaa tttaaaccta      1800
cgagattgac attctcgact gatcttgatt gatcggtaag tcttttgtaa tttaattttc      1860
tmtgatttta ttttaaattg ttatctgttt ctgtgtatag actgtttgag atcggcgttt      1920
ggccgactca ttgtcttacc ataggggaac ggactttgtt tgtgttgtta tntatttgta      1980
ttttattaaa attctcaacg atctgaaaaa gcctcgcggc taagagattg ttggggggtg      2040
agtaagtact tttaaagtga tgatggttac aaaggcaaaa ggggtaaaac ccctcgccta      2100
cgtaagcgtt attacgcccg tctgtactta tatcagtaca ctgacgagtc cctaaaggac      2160
gaaacgggag aacgctagcc accaccacca ccaccacgtg tgaattacag gtgaccagct      2220
cgaatttccc cgatcgttca aacatttggc aataaagttt cttaagattg aatcctgttg      2280
ccggtcttgc gatgattatc atataatttc tgttgaatta cgttaagcat gtaataatta      2340
acatgtaatg catgacgtta tttatgagat gggtttttat gattagagtc ccgcaattat      2400
acatttaata cgcgatagaa aacaaaatat agcgcgcaaa ctaggataaa ttatcgcgcg      2460
cggtgtcatc tatgttacta gatc                                            2484
```

<210> SEQ ID NO 22
<211> LENGTH: 3160
<212> TYPE: DNA
<213> ORGANISM: Artificial Sequence
<220> FEATURE:
<223> OTHER INFORMATION: Synthetic T7 driven RNA2 with sample construct
      (C3) in MCS, ribozyme, NOS

<400> SEQUENCE: 22

```
taatacgact cactatagga taaaacattg cacctatggt gttgccctgg ctggggtatg        60
tcagtgatcg cagtagaatg tactaattga caagttggag aatacggtag aacgtcctta       120
tccaacacag cctttatccc tctccctgac gaggttttg tcagtgtaat atttcttttt        180
gaactatcca gcttagtacc gtacgggaaa gtgactggtg tgcttatctt tgaaatgtta       240
ctttgggttt cggttcttta ggttagtaag aaagcacttg tcttctcata caaaggaaaa       300
cctgagacgt atcgcttacg aaagtagcaa tgaaagaaag gtggtggttt taatcgctac       360
cgcaaaaacg atgggtcgt tttaattaac ttctcctacg caagcgtcta acgacgtt         420 ggggttttgc tagtttcttt agagaaaact agctaagtct ttaatgttat cattagagat       480
ggcataaata taatacttgt gtctgctgat aagatcattt taatttggac gattagactt       540
gttgaactac aggttactga atcacttgcg ctaatcaaca tggagatat gtacgatgaa        600 tcatttgaca agtcgggcgg tcctgctgac ttgatggacg attcttgggt ggaatcagtt       660
tcgtggaaag atctgttgaa gaagttacac agcataaaat ttgcactaca gtctggtaga       720
gatgagatca ctgggttact agcggcactg aatagacagt gtccttattc accatatgag       780
cagtttccag ataagaaggt gtatttcctt ttagactcac gggctaacag tgctcttggt       840
gtgattcaga acgcttcagc gttcaagaga cgagctgatg agaagaatgc agtggcgggt       900
gttacaaata ttcctgcgaa tccaaacaca acggttacga cgaaccaagg gagtactact       960
```

```
actaccaagg cgaacactgg ctcgactttg gaagaagact tgtacactta ttacaaattc    1020
gatgatgcct ctacagcttt ccacaaatct ctaacttcgt tagagaacat ggagttgaag    1080
agttattacc gaaggaactt tgagaaagta ttcgggatta gtttggtgg agcagctgct     1140 agttcatctg caccgcctcc agcgagtgga ggtccgatac gtcctaatcc ctagggattt    1200
aaggacgtga actctgttga gatctctgtg aaattcagag ggtgggtgat accatattca    1260
ctgatgccat tagcgacatc taaatagggc taattgtgac taatttgagg gaatttcctt    1320
taccattgac gtcagtgtcg ttggtagcat ttgagtttcg caatgcacga attacttagg    1380
aagtggcttg acgacactaa tgtgttattg ttagataatg gtttggtggt caaggtacgt    1440
agtagagtcc cacatattcg cacgtatgaa gtaattggaa agttgtcagt ttttgataat    1500
tcactgggag atgatacgct gtttgaggga aaagtagaga acgtatttgt ttttatgttc    1560
aggcggttct tgtgtgtcaa caaagatgga cattgttact caaggaagca cgatgagctt    1620
tattattacg gacgagtgga cttagattct gtgagtaatc tgaccaggtc tcatcgtgtc    1680
gacggaggaa gtgaagcaca gaaatggaac aaaaataaaa ccttggggta ctctttgatc    1740
ttctttgcaa gaatgtaatg aatatccctg attactttct tcatataccg tccgtcaagt    1800
gccttcaatt gctgaagcca atcctaaat cccataccac aagattacag gcatagagtc      1860
tcgaagcatt attaataact cattggcgat caaattaaga tgaatgtcag tttattaaag    1920
gaaaaagtaa agaacaagaa caaatcatt tggcactttt catactacaa ccatcgacaa      1980
aattagctgc tgccactgct tctttgacat gtaatacggg agactcactg ctatttcatt    2040
atttggctca aggcaaagga attaggagat gaagtggatg gatatgatga aagctcctcc    2100
gccaccacct aatcaataca atagcagcag tagtactaat aaccttagcc aaagcaaaga    2160
aatcagagaa gaagaagagc gaaaaagctt gccttcttct ccatacaatc cggccaaagt    2220
ttcaatatcc ggatcatgga caccaataac aatacttata ggatcactat acagcaaacg    2280
agatgcaatt ttagctaaga cagaagtttc acaagctcat ttagagctgt taaagaagac    2340
taatgaagca gcaatagaag aaacagaaa gcaatctcga gctcctgaga cctggtcctc     2400
atgtcccgaa gacattaaac tacggttctt taagtagatc cgtgtctgaa gttttaggtt    2460
caatttaaac ctacgagatt gacattctcg actgatcttg attgatcggt aagtcttttg    2520
taatttaatt ttcttttga ttttatttta aattgttatc tgtttctgtg tatagactgt      2580
ttgagatcgg cgtttggccg actcattgtc ttaccatagg ggaacggact ttgtttgtgt    2640
tgttatttta tttgtatttt attaaaattc tcaacgatct gaaaaagcct cgcggctaag    2700
agattgttgg ggggtgagta agtacttta aagtgatgat ggttacaaag gcaaagggg      2760 taaaacccct cgcctacgta agcgttatta cgcccgtctg tacttatatc agtacactga    2820
cgagtcccta aaggacgaaa cgggagaacg ctagccacca ccaccaccac cacgtgtgaa    2880
ttacaggtga ccagctcgaa tttccccgat cgttcaaaca tttggcaata agtttctta    2940 agattgaatc ctgttgccgg tcttgcgatg attatcatat aatttctgtt gaattacgtt    3000
aagcatgtaa taattaacat gtaatgcatg acgttattta tgagatgggt ttttatgatt    3060
agagtcccgc aattatacat ttaatacgcg atagaaaaca aaatatagcg cgcaaactag    3120
gataaattat cgcgcgcggt gtcatctatg ttactagatc                          3160
```

<210> SEQ ID NO 23
<211> LENGTH: 3232
<212> TYPE: DNA

<213> ORGANISM: Artificial Sequence
<220> FEATURE:
<223> OTHER INFORMATION: Synthetic T7-RNA2-sgP-C3 sequence

<400> SEQUENCE: 23

```
taatacgact cactatagga taaaacattg cacctatggt gttgccctgg ctggggtatg      60
tcagtgatcg cagtagaatg tactaattga caagttggag aatacggtag aacgtcctta     120
tccaacacag cctttatccc tctccctgac gaggttttttg tcagtgtaat atttcttttt    180
gaactatcca gcttagtacc gtacgggaaa gtgactggtg tgcttatctt tgaaatgtta    240
ctttgggttt cggttcttta ggttagtaag aaagcacttg tcttctcata caaaggaaaa    300
cctgagacgt atcgcttacg aaagtagcaa tgaaagaaag gtggtggttt taatcgctac    360
cgcaaaaacg atgggtcgt tttaattaac ttctccctacg caagcgtcta aacggacgtt    420
ggggttttgc tagtttcttt agagaaaact agctaagtct ttaatgttat cattagagat    480
ggcataaata taatacttgt gtctgctgat aagatcattt taatttggac gattagactt    540
gttgaactac aggttactga atcacttgcg ctaatcaaca tgggagatat gtacgatgaa    600
tcatttgaca agtcgggcgg tcctgctgac ttgatggacg attcttgggt ggaatcagtt    660
tcgtggaaag atctgttgaa gaagttacac agcataaaat ttgcactaca gtctggtaga    720
gatgagatca ctgggttact agcggcactg aatagacagt gtccttattc accatatgag    780
cagtttccag ataagaaggt gtatttcctt ttagactcac gggctaacag tgctcttggt    840
gtgattcaga acgcttcagc gttcaagaga cgagctgatg agaagaatgc agtggcgggt    900
gttacaaata ttcctgcgaa tccaaacaca acgttacga cgaaccaagg gagtactact    960
actaccaagg cgaacactgg ctcgactttg aagaagact tgtacactta ttacaaattc    1020
gatgatgcct ctcagctttt ccacaaatct ctaacttcgt tagagaacat ggagttgaag    1080
agttattacc gaaggaactt tgagaaagta ttcgggatta gtttggtgg agcagctgct    1140
agttcatctg caccgcctcc agcgagtgga ggtccgatac gtcctaatcc ctagggattt    1200
aaggacgtga actctgttga gatctctgtg aaattcagag ggtgggtgat accatattca    1260
ctgatgccat tagcgacatc taaataaggc taattgtgac taatttgagg gaatttcctt    1320
taccattgac gtcagtgtcg ttggtagcat ttgagtttcg gagcatcttg ttctggggtt    1380
tcacactatc tttagagaaa gtgttaagtt aattaagtta tcttaattaa gagcataatt    1440
atactgattt gtctctcgtt gatagagtct atcattctgt tactaaaaat ttgacaactc    1500
ggtttgctga cctactggtt actgtatcac ttacccgagt taacgaggga ggaagtgaag    1560
cacagaaatg gaacaaaaat aaaaccttgg ggtactcttt gatcttcttt gcaagaatgt    1620
aatgaatatc cctgattact ttcttcatat accgtccgtc aagtgccttc aattgctgaa    1680
gccaaatcct aaatcccata ccacaagatt acaggcatag agtctcgaag cattattaat    1740
aactcattgg cgatcaaatt aagatgaatg tcagtttatt aaaggaaaaa gtaaagaaca    1800
agaacaaaat catttggcac ttttcatact acaaccatcg acaaaattag ctgctgccac    1860
tgcttctttg acatgtaata cgggagactc actgctattt cattatttgg ctcaaggcaa    1920
aggaattagg agatgaagtg gatggatatg atgaaagctc ctccgccacc acctaatcaa    1980
tacaatagca gcagtagtac taataacctt agccaaagca agaaatcag agaagaagaa    2040
gagcgaaaaa gcttgccttc ttctccatac aatccggcca agttcaat atccggatca    2100
tggacaccaa taacaatact tataggatca ctatacagca aacagagatgc aatttttagct    2160
aagacagaag tttcacaagc tcatttagag ctgttaaaga agactaatga agcagcaata    2220
```

```
gaagaaacag agaagcaatc tcgagctcct gagacctggt cctcctcgtt aactcgggta    2280
agtgatacag taaccagtag gtcagcaaac cgagttgtca aatttttagt aacagaatga    2340
tagactctat caacgagaga caaatcagta taattatgct cttaattaag ataacttaat    2400
taacttaaca ctttctctaa agatagtgtg aaacccaga acaagatgct catgtcccga     2460
agacattaaa ctacggttct ttaagtagat ccgtgtctga agttttaggt tcaatttaaa    2520
cctacgagat tgacattctc gactgatctt gattgatcgg taagtctttt gtaatttaat    2580 tttcttttg attttatttt aaattgttat ctgtttctgt gtatagactg tttgagatcg     2640
gcgtttggcc gactcattgt cttaccatag gggaacggac tttgtttgtg ttgttatttt    2700
atttgtattt tattaaaatt ctcaacgatc tgaaaaagcc tcgcggctaa gagattgttg    2760
gggggtgagt aagtactttt aaagtgatga tggttacaaa ggcaaaaggg gtaaaacccc    2820
tcgcctacgt aagcgttatt acgcccgtct gtacttatat cagtacactg acgagtccct    2880
aaaggacgaa acgggagaac gctagccacc accaccacca ccacgtgtga attacaggtg    2940
accagctcga atttccccga tcgttcaaac atttggcaat aaagtttctt aagattgaat    3000
cctgttgccg gtcttgcgat gattatcata taatttctgt tgaattacgt taagcatgta    3060
ataattaaca tgtaatgcat gacgttattt atgagatggg ttttatgat tagagtcccg     3120 caattataca tttaatacgc gatagaaaac aaaatatagc gcgcaaacta ggataaatta    3180
tcgcgcgcgg tgtcatctat gttactagat cgggaattaa actatcagtg tt            3232
```

<210> SEQ ID NO 24
<211> LENGTH: 2823
<212> TYPE: DNA
<213> ORGANISM: Artificial Sequence
<220> FEATURE:
<223> OTHER INFORMATION: Synthetic sequence consisting of PUC57 MCS
      flanked by PEBV subgenomic promoters all of which are flanked by
      T7 promoters
<220> FEATURE:
<221> NAME/KEY: misc_feature
<222> LOCATION: (1720)..(1720)
<223> OTHER INFORMATION: n is a, c, g or t

<400> SEQUENCE: 24

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaataata cgactcacta tagggagata ccattgacgt    180
cagtgtcgtt ggtagcattt gagtttcgga gcatcttgtt ctggggtttc acactatctt    240
tagagaaagt gttaagttaa ttaagttatc ttaattaaga cataattat actgatttgt     300 ctctcgttga tagagtctat cattctgtta ctaaaaattt gacaactcgg tttgctgacc    360
tactggttac tgtatcactt acccgagtta acgaggtgaa ttcgagctcg gtacctcgcg    420
aatgcatcta gatatcggat cccgggcccg tcgactgcag aggcctgcat gcaagcttgc    480
tcgttaactc gggtaagtga tacagtaacc agtaggtcag caaaccgagt tgtcaaattt    540
ttagtaacag aatgatagac tctatcaacg agagacaaat cagtataatt atgctcttaa    600
ttaagataac ttaattaact taacactttc tctaaagata gtgtgaaacc ccagaacaag    660
atgctccgaa actcaaatgc taccaacgac actgacgtca atggtatctc cctatagtga    720
gtcgtattat cactgcccgc tttccagtcg ggaaacctgt cgtgccagct gcattaatga    780
atcggccaac gcgcggggag aggcggtttg cgtattgggc gctcttccgc ttcctcgctc    840
```

-continued

```
actgactcgc tgcgctcggt cgttcggctg cggcgagcgg tatcagctca ctcaaaggcg    900
gtaatacggt tatccacaga atcaggggat aacgcaggaa agaacatgtg agcaaaaggc    960
cagcaaaagg ccaggaaccg taaaaaggcc gcgttgctgg cgtttttcca taggctccgc   1020 cccccctgacg agcatcacaa aaatcgacgc tcaagtcaga ggtggcgaaa cccgacagga  1080
ctataaagat accaggcgtt tccccctgga agctccctcg tgcgctctcc tgttccgacc   1140
ctgccgctta ccggatacct gtccgccttt ctcccttcgg gaagcgtggc gctttctcat   1200
agctcacgct gtaggtatct cagttcggtg taggtcgttc gctccaagct gggctgtgtg   1260
cacgaacccc ccgttcagcc cgaccgctgc gccttatccg gtaactatcg tcttgagtcc   1320
aacccggtaa gacacgactt atcgccactg gcagcagcca ctggtaacag gattagcaga   1380
gcgaggtatg taggcggtgc tacagagttc ttgaagtggt ggcctaacta cggctacact   1440
agaagaacag tatttggtat ctgcgctctg ctgaagccag ttaccttcgg aaaaagagtt   1500
ggtagctctt gatccggcaa acaaaccacc gctggtagcg gtggtttttt tgtttgcaag   1560
cagcagatta cgcgcagaaa aaaaggatct caagaagatc ctttgatctt ttctacgggg   1620
tctgacgctc agtggaacga aaactcacgt taagggattt tggtcatgag attatcaaaa   1680
aggatcttca cctagatcct tttaaattaa aaatgaagtn taaatcaatc taaagtatat   1740
atgagtaaac ttggtctgac agttaccaat gcttaatcag tgaggcacct atctcagcga   1800
tctgtctatt tcgttcatcc atagttgcct gactccccgt cgtgtagata actacgatac   1860
gggagggctt accatctggc cccagtgctg caatgatacc gcgagaccca cgctcaccgg   1920
ctccagattt atcagcaata aaccagccag ccggaagggc cgagcgcaga agtggtcctg   1980
caactttatc cgcctccatc cagtctatta attgttgccg ggaagctaga gtaagtagtt   2040
cgccagttaa tagtttgcgc aacgttgttg ccattgctac aggcatcgtg gtgtcacgct   2100
cgtcgtttgg tatggcttca ttcagctccg gttcccaacg atcaaggcga gttacatgat   2160
cccccatgtt gtgcaaaaaa gcggttagct ccttcggtcc tccgatcgtt gtcagaagta   2220
agttggccgc agtgttatca ctcatggtta tggcagcact gcataattct cttactgtca   2280
tgccatccgt aagatgcttt tctgtgactg gtgagtactc aaccaagtca ttctgagaat   2340
agtgtatgcg gcgaccgagt tgctcttgcc cggcgtcaat acgggataat accgcgccac   2400
atagcagaac tttaaaagtg ctcatcattg gaaaacgttc ttcggggcga aaactctcaa   2460
ggatcttacc gctgttgaga tccagttcga tgtaacccac tcgtgcaccc aactgatctt   2520
cagcatcttt tactttcacc agcgtttctg ggtgagcaaa aacaggaagg caaaatgccg   2580
caaaaaaggg aataagggcg acacggaaat gttgaatact catactcttc ctttttcaat   2640
attattgaag catttatcag ggttattgtc tcatgagcgg atacatattt gaatgtattt   2700
agaaaaataa acaaataggg gttccgcgca catttccccg aaaagtgcca cctgacgtct   2760
aagaaaccat tattatcatg acattaacct ataaaaatag gcgtatcacg aggccctttc   2820
gtc                                                                 2823
```

```
<210> SEQ ID NO 25
<211> LENGTH: 7560
<212> TYPE: RNA
<213> ORGANISM: Artificial Sequence
<220> FEATURE:
<223> OTHER INFORMATION: Synthetic RNA1 of TRV Ppk20 sequence

<400> SEQUENCE: 25
aagcuugcau gccugcaggu caacauggug gagcacgaca cucucgucua cuccaagaau     60
```

| | |
|---|---|
| aucaaagaua cagucucaga agaccagagg gcuauugaga cuuuucaaca aaggguaaua | 120 |
| ucgggaaacc uccucggauu ccauugccca gcuaucuguc acuucaucga aaggacagua | 180 |
| gaaaaggaag auggcuucua caaaugccau cauugcgaua aaggaaaggc uaucguucaa | 240 |
| gaugccucua ccgacagugg ucccaaagau ggaccccac ccacgaggaa caucuggaa | 300 |
| aaagaagacg uuccaaccac gucuucaaag caaguggauu gaugugaugg ucaacauggu | 360 |
| ggagcacgac acucucgucu acuccaagaa uaucaaagau acagucucag aagaccagag | 420 |
| ggcuauugag acuuucaac aaaggguaau aucgggaaac cuccucggau uccauugccc | 480 |
| agcuaucugu cacuucaucg aaaggacagu agaaaaggaa gauggcuucu acaaaugcca | 540 |
| ucauugcgau aaaggaaagg cuaucguuca agaugccucu accgacagug ucccaaaga | 600 |
| uggaccccca cccacgagga caucgugga aaaagaagac guuccaacca cgucuucaaa | 660 |
| gcaaguggau ugaugugaua ucccacuga cguaagggau gacgcacaau cccacuaucc | 720 |
| uucgcaagac ccuccucua uauaaggaag uucauucau uggagagga uaaaacauuu | 780 |
| caauccuuug aacgcgguag aacgugcuaa uuggauuuug ugagaacgc gguagaacgu | 840 |
| acuuaucacc uacaguuuua uuuguuuuu cuuuuugguu uaaucuaucc agcuuaguac | 900 |
| cgagugggg aaagugacug gugugccuaa aaccuuuucu uugauacuuu guaaaauac | 960 |
| auacagauac aauggcgaac gguaacuuca aguugcuca auugcucaau gggacgaga | 1020 |
| ugucugcuga gcagaggagu cauuucuuug acuugaugcu gacuaaaccu gauugugaga | 1080 |
| ucgggcaaau gaugcaaaga guuguuguug auaaagucga ugacaugauu agagaaagaa | 1140 |
| agacuaaaga uccagugauu guucaugaag uucuuucuca gaaggaacag aacaaguuga | 1200 |
| uggaaauuua uccugaauuc aauaucgugu uaaagacga caaaaacaug guucaugggu | 1260 |
| uugcggcugc ugagcgaaaa cuacaagcuu uauugcuuuu agauagaguu ccugcucugc | 1320 |
| aagaggugga ugacaucggu ggucaauggu cguuugggu aacagaggu gagaaaagga | 1380 |
| uucauuccug uuguccaaau cuagauauuc gggaugauca gagagaaauu ucucgacaga | 1440 |
| uauuucuuac ugcuauuggu gaucaagcua aagugguaa agacagaug ucggagaaug | 1500 |
| agcugguggau guaugaccaa uuucgugaaa auauugcugc gccuaacgcg guuaggugca | 1560 |
| auaauacaua ucagguugu acauguaggg guuuuucuga ugguaagaag aaaggcgcgc | 1620 |
| aguaugcgau agcucuucac agccuguaug acuucaaguu gaaagacuug auggcuacua | 1680 |
| ugguugagaa gaaaacuaaa gugguucaug cugcuaugcu uuuugcccu gaaaguaugu | 1740 |
| uaguggacga agguccauua ccuucuguug acguuacua caugaagaag aacgggaaga | 1800 |
| ucuauuucgg uuuugagaaa gauccuuccu uuucuuacau ucaugacugg gaagaguaca | 1860 |
| agaaguaucu acuggggaag ccagugaguu accaagggaa uguuucuac uucgaaccgu | 1920 |
| ggcaggugag aggagacaca augcuuuuuu cgaucuacag gauagcugga guccgagga | 1980 |
| ggucucuauc aucgcaagag uacuaccgaa gaauauauau caguagaugg gaaaacaugg | 2040 |
| uuguguccc aauuuucgau cuggucgaau caacgcgaga guuggucaag aaagaccugu | 2100 |
| uuguagagaa acaauucaug gacaagugu uggauuacau agcuagguua ucugaccagc | 2160 |
| agcugaccau aagcaauguu aaaucauacu ugaguucaaa uaauuggguc uuauucauaa | 2220 |
| acggggcggc cgugaagaac aagcaaagug uagauucucg agauuuacag uuguuggcuc | 2280 |
| aaacuuugcu aguaaggaa caagugcga gaccugucau gagggaguug cgugaagcaa | 2340 |
| uucugacuga gacgaaaccu aucacgucau ugacugaugu gcuggguuua auaucaagaa | 2400 |

```
aacuguggaa gcaguuugcu aacaagaucg cagucggcgg auucguuggc augguuggua    2460
cucuaauugg auucuaucca aagaagguac uaaccugggc gaaggacaca ccaaaugguc    2520
cagaacuaug uuacgagaac ucgcacaaaa ccaaggugau aguauuucug aguguugugu    2580
augccauugg aggaaucacg cuuaugcguc gagacauccg agauggacug ugaaaaaac     2640
uaugugauau guuugauauc aaacgggggg cccaugucuu agacguugag aauccgugcc    2700
gcuauuauga aaucaacgau uucuuuagca gucuguauuc ggcaucgag uccggugaga     2760
ccguuuuacc agauuuaucc gagguaaaag ccaagucuga uaagcuauug cagcagaaga    2820
aagaaaucgc ugacgaguuu cuaagugcaa aauucucuaa cuauucggc aguucgguga     2880
gaacuucucc accaucgguc gucgguucau cucgaagcgg acuggucug uuguuggaag     2940
acaguaacgu gcugacccaa gcuagaguug gaguuucaag aaaggugac gaugaggaga     3000
ucauggagca guuucugagu ggucuuauug acacugaagc agaaauugac gagguuguuc    3060
cagccuuuuc agcugaaugu gaaagagggg aaacaagcgg uacaaaggug uuguguaaac    3120
cuuuaacgcc accaggauuu gagaacgugu ugccagcugu caaaccuuug gucagcaaag    3180
gaaaaacggu caaacugugc gauuacuucc aagugauggg aggugagaga uuaccaaaaa    3240
ggccgguugu caguggagac gauucugugg acgcuagaag agaguuucug uacuacuuag    3300
augcggagag agucgcucaa aaugaugaaa uuaugucucu guaucgugac uauucgagag    3360
gaguuauucg aacuggaggu cagaauuacc cgcacgacu gggagugugg gauguggaga     3420
ugaagaacug gugcauacgu ccaguggucaa cugaacaugc uuaugguuc caaccagaca    3480
aacguaugga ugauuggucg ggauacuuag aaguggcugu uugggaacga gguauguugg    3540
ucaacgacuu cgcggucgaa aggaugagug auuaugucau aguuugcgau cagacguauc    3600
uuugcaauaa cagguugauc uuggacaauu uaagugcccu ggaucuagga ccaguuaacu    3660
guucuuuuga auuaguugac gguguaccug uuguggua ucgacaaug auugucaacu       3720
cagcuaaucc uugugucgau guggucucu cuacugggag agcagcaacc gacgacuuga     3780
ucgagagau cgcgagcaaa gguuuuccau gcaaauugaa aggagagug aagacgguug      3840
auucuuuuuu gaugcauugu guugaugguu cuuuaaccgg agacguuug cauuucgaug     3900
aagcucucau ggcccaugcu gguauggugu acuuugcgc ucagauagcu ggugcuaaac     3960
gauguaucug ucaaggagau cagaaucaaa uuucuuucaa gccuagggua ucucaaguug    4020
auuugagguu uucuagucug gucggaaagu uugacauugu uacagaaaaa agagaaacuu    4080
acagaaguccc agcagaugug gcugccguau ugaacaagua cuauacugga gaugucagaa   4140
cacauaacgc gacugcuaau ucgaugacgg ugaggaagau ugugucuaaa gaacagguuu    4200
cuuugaagcc uggugcucag uacauaacuu uccuucaguc ugagaagaag gaguggguaa    4260
auugguuggc auugaggaaa guggcagcua aagugaguac aguacacgag ucgcaaggag    4320
agacauucaa agauguaguc cuagucagga cgaaaccuac ggaugacuca aucgcuagag    4380
gucgggagua cuuaaucgug gcguugucgc gucacacaca aucacuugug uaugaaacug    4440
ugaaagagga cgauguaagc aaagagauca gggaagugc cgcgcuuacg aaggcggcuu     4500
uggcaagauu uuuguuacu gagaccgucu uaugacgguu ucggcuuagg uuugaugucu     4560
uuagacauca ugaagggccu ugcgccguuc cagauucagg uacgauuacg gacuugaga     4620
uguggugacgu cgcuuuguuu ccgggaaauu cguuagagaa cucaagccua gacggguauu    4680
uggggcaac gacugauugc aauuugcgau uagacauugu uacgaucaaa aguggaaacu      4740
ggaaagacaa guuugcugaa aaagaaacgu uucugaaacc gguuauucgu acugcuaugc     4800
```

-continued

```
cugacaaaag gaagacuacu caguuggaga guuuguuagc auugcagaaa aggaaccaag    4860
cggcacccga ucuacaagaa aaugugcacg caacaguucu aaucgaagag acgaugaaga    4920
aguugaaauc uguugucuac gaugugggaa aaauucgggc ugauccuauu gucaauagag    4980
cucaaaugga gagauggugg agaaaucaaa gcacagcggu acaggcuaag guaguagcag    5040
augugagaga guuacaugaa auagacuauu cgucuuacau guauaugauc aaaucugacg    5100
ugaaaccuaa gacugauuua acaccgcaau uugaauacuc agcucuacag acuguugugu    5160
aucacgagaa guugaucaac ucguuguucg guccaauuuu caaagaaauu aaugaacgca    5220
aguuggaugc uaugcaacca cauuuugugu caacacgag aaugacaucg agugauuuaa     5280
acgaucgagu gaaguucuua aauacggaag cggcuuacga cuuuguugag auagacaugu    5340
cuaaauucga caagucggca aaucgcuucc auuuacaacu gcagcuggag auuuacaggu    5400
uauuugggcu agaugagugg gcggccuucc uuugggaggu gucgcacacu caaacuacug    5460
ugagagauau ucaaaauggu augauggcgc auauuuggua ccaacaaaag aguggagaug    5520
cugauacuua uaaugcaaau ucagauagaa cacgugugc acucuugucu gaauuaccau     5580
uggagaaagc agucauggu acauauggag gagaugacuc acugauugcg uuuccuagag     5640
gaacgcaguu uguugauccg uguccaaagu uggcuacuaa guggaauuuc gagugcaaga    5700
uuuuuaagua cgauguccca auguuuugug gaaguucuu gcuuaagacg ucaucguguu     5760
acgaguucgu gccagauccg uaaaaguuc ugacgaaguu ggggaaaaag aguauaaagg     5820
augugcaaca uuuagccgag aucuacaucu cgcugaauga uuccaauaga gcucuuggga    5880
acuacauggu gguauccaaa cuguccgagu cuguuucaga ccgguauuug uacaaaggug    5940
auucuguuca ugcgcuuugu gcgcuaugga agcauauuaa gaguuuuaca gcucugugua    6000
cauuauuccg agacgaaaac gauaaggaau ugaacccggc uaagguugau uggaagaagg    6060
cacagagagc uguguccaaac uuuuacgacu gguauauugg aagacaaguc auuggucacc    6120
uugaagaaga agacuuucga agcucaaaaa uucucaaauc uaggggccau ugaauuguuu     6180
guggacggua ggaggaagag accgaaguau uuucacagaa gaagagaaac uguccuaaau    6240
caguguggug ggaagaagag ugaacacaag uuagacguuu ugaccaaag ggauuacaaa     6300 augauuaaau cuuacgcguu ucuaaagaua guagguguac aacuaguguga aaucacau     6360 cuaccugcag auacgccugg guucauucaa aucgaucugu uggauucgag acuuacugag    6420
aaaagaaaga gaggaaagac uauucagaga uucaaagcuc gagcuugcga uaacuguuca    6480
guugcgcagu acaagguuga auacaguauu uccacacagg agaacguacu ugaugucugg    6540 aaggugggu guauuucuga gggcguuccg gucugugacg guacauaccc uuucaguauc     6600
gaagugucgc uaauaugggu ugcuacgau ucgacuaggc gccucaaugu ggaagaacug      6660
aacaguucgg auuacauuga aggcgauuuu accgaucaag agguuuucgg ugaguucaug    6720
ucuuugaaac aaguggagau gaagacgauu gaggcgaagu acgauggucc uuacagacca    6780
gcuacuacua gaccuaaguc auuauugca agugaagaug uuaagagagc gucuaauaag    6840
aaaaacucgu cuuaaugcau aaagaaauuu auugucaaua ugacgugugu acucaagggu    6900
ugugugaaug aagucacugu ucuuggucac gagacgugua guaucgggca ugcuaacaaa    6960
uugcgaaagc aaguugcuga cauggguugu gucacacgua ggugugcgga aaauaauugu    7020
ggauggauug ucugugguu uaucaagau uuuacuuuug auguguauaa uguugugggc      7080
cguagucacc uugaaaagug ucguaaacgu guugaaacaa gaaaucgaga aauuggaaa    7140
```

| | | |
|---|---|---|
| caaauucgac gaaaucaagc ugaaaacaug ucugcgacag cuaaaaaguc ucauaauucg | | 7200 |
| aagaccucua agaagaaauu caaagaggac agagaauuug ggacaccaaa aagauuuuua | | 7260 |
| agagaugaug uuccuuucgg gauugaucgu uguuugcuuu uugauuuua uuuuauauug | | 7320 |
| uuaucuguuu cuguguauag acuguuugag auuggcgcuu ggccgacuca uugucuuacc | | 7380 |
| auaggggaac ggacuuuguu uguuguuua uuuuauuugu auuuuauuaa aauucucaau | | 7440 |
| gaucugaaaa ggccucgagg cuaagagauu auuggggggu gaguaaguac uuuuaaagug | | 7500 |
| augauguua caaaggcaaa aggguaaaa ccccucgccu acguaagcgu uauuacgccc | | 7560 |

<210> SEQ ID NO 26
<211> LENGTH: 2776
<212> TYPE: RNA
<213> ORGANISM: Artificial Sequence
<220> FEATURE:
<223> OTHER INFORMATION: Synthetic RNA2 of pTRV2 with C3 insert sequence

<400> SEQUENCE: 26

| | | |
|---|---|---|
| auaaaacauu gcaccuaugg uguugcccug gcuggggauu ucagugaauc gcaguagaau | | 60 |
| guacuaauug acaaguugga gaauacggua gaacguccuu auccaacaca gccuuuaucc | | 120 |
| cucucccuga cgagguuuuu gucaguguaa uauuucuuuu ugaacuaucc agcuuaguac | | 180 |
| cguacgggaa agugacuggu gugcuuaucu ugaaauguu acuuuggguu ucgguucuuu | | 240 |
| agguuaguaa gaaagcacuu gucuucucau acaaaggaaa accugagacg uaucgcuuac | | 300 |
| gaaaguagca augaaagaaa ggugguгuggu uuaaucgcua ccgcaaaaac gauggggucg | | 360 |
| uuuuaauuaa cuuccucccuac gcaagcgucu aaacggacgu uggggguuuug cuaguuucuu | | 420 |
| uagagaaaac uagcuaaguc uuuaauguua ucauagaga uggcauaaau auaauacuug | | 480 |
| ugucugcuga uaagaucauu uuaauuugga cgauugacu uguugaacua cagguuacg | | 540 |
| aaucacuugc gcuaaucaac augggagaua uguacgauga aucauuugac aagucgggcg | | 600 |
| guccugcuga cuugauggac gauucuuggg uggaaucagu uucgggaaa gaucuguuga | | 660 |
| agaaguuaca cagcauaaaa uuugcacuac agucugguag agaugagauc acuggguuac | | 720 |
| uagcggcacu gaauagacag uguccuuauu caccauauga gcaguuucca gauaagaagg | | 780 |
| uguauuuccu uuuagacuca cgggcuaaca gugcucuugg ugugauucag aacgcuucag | | 840 |
| cguucaagag acgagcugau gagaagaaug caguggcggg uguuacaaau auuccugcga | | 900 |
| auccaaacac aacgguuacg acgaaccaag ggaguacuac uacuaccaag gcgaacacug | | 960 |
| gcucgacuuu ggaagaagac uuguacacuu auuacaaauu cgaugaugcc ucuacagcuu | | 1020 |
| uccacaaauc ucuaacuucg uuagagaaca uggaguugaa gaguuauuac cgaaggaacu | | 1080 |
| uugaaaagu auucgggauu aaguuuggug gagcagcugc uaguucaucu gcaccgccuc | | 1140 |
| cagcgagugg agguccgaua cguccuaauc ccuagggauu uaaggacgug aacucuguug | | 1200 |
| agaucucugu gaaauucaga gggguggguga uaccauauuc acugaugcca uuagcgacau | | 1260 |
| cuaaauaggg cuaauuguga cuaauuugag ggaauuuccu uuaccauuga cgucagcuc | | 1320 |
| guuggguagca uuugaguuuc gcaaugcacg aauuacuuag gaaguggcuu gacgacacua | | 1380 |
| auguguuauu guuagauaau gguuuggugg ucaaggacag uaguagaguc ccacauauuc | | 1440 |
| gcacguauga aguaauugga aaguugucag uuuugauaa uucacuggga gaugauacgc | | 1500 |
| uguuugaggg aaaaguagag aacguauuug uuuuauguu caggcgguuc uugugugugca | | 1560 |
| acaaagaugg acauuguuac ucaaggaagc acgaugagcu uauuauuac ggacgagugg | | 1620 |
| acuuagauuc uguguagaau cugaccaggu cucaucgugu cgacggagga agugaagcac | | 1680 |

| | | | | |
|---|---|---|---|---|
| agaaauggaa | caaaaauaaa | accuuggggu | acucuuugau | cuucuuugca agaauguaau | 1740 |
| gaauacccu | gauuacuuuc | uucauauacc | guccgucaag | ugccuucaau ugcugaagcc | 1800 |
| aaauccuaaa | ucccauacca | caagauuaca | ggcauagagu | cucgaagcau uauuaauaac | 1860 |
| ucauuggcga | ucaaauuaag | augaauguca | guuuauuaaa | ggaaaaagua aagaacaaga | 1920 |
| acaaaaucau | uuggcacuuu | ucauacuaca | accaucgaca | aaauuagcug cugccacugc | 1980 |
| uucuuugaca | uguaauacgg | gagacucacu | gcauuucau | uauuuggcuc aaggcaaagg | 2040 |
| aauuaggaga | ugaaguggau | ggauaugaug | aaagcccuc | cgccaccacc uaaucaauac | 2100 |
| aauagcagca | guaguacuaa | uaaccuuagc | caaagcaaag | aaaucagaga agaagaagag | 2160 |
| cgaaaaagcu | ugccuucuuc | uccauacaau | ccggccaaag | uuucaauauc cggaucaugg | 2220 |
| acaccaauaa | caauacuuau | aggaucacua | uacagcaaac | gagaugcaau uuuagcuaag | 2280 |
| acagaaguuu | cacaagcuca | uuuagagcug | uuaaagaaga | cuaaugaagc agcaauagaa | 2340 |
| gaaacagaga | agcaaucucg | agcuccugag | accggaccu | caugucccga agacauuaaa | 2400 |
| cuacgguucu | uuaaguagau | ccgugucuga | aguuuuaggu | ucaauuuaaa ccuacgagau | 2460 |
| ugacauucuc | gacugaucuu | gauugaucgg | uaagucuuuu | guaauuuaau uuucuuuuug | 2520 |
| auuuuauuuu | aaauuguuau | cuguuucugu | guauagacug | uuugagaucg gcguuuggcc | 2580 |
| gacucauugu | cuuaccauag | gggaacggac | uuuguuugug | uuguuauuuu auuuguauuu | 2640 |
| uauuaaaauu | cucaacgauc | ugaaaaagcc | ucgcggcuaa | gagauuguug gggggugagu | 2700 |
| aaguacuuuu | aaagugauga | ugguuacaaa | ggcaaaaggg | guaaaacccc ucgccuacgu | 2760 |
| aagcguuauu | acgccc | | | | 2776 |

<210> SEQ ID NO 27
<211> LENGTH: 1091
<212> TYPE: RNA
<213> ORGANISM: Artificial Sequence
<220> FEATURE:
<223> OTHER INFORMATION: Synthetic sequence consisting of SEQ_15 flanked
 by PEBV subgenomic promoters

<400> SEQUENCE: 27

| | | | | |
|---|---|---|---|---|
| gagcaucuug | uucuggggu | ucacacuauc | uuuagagaaa | guguuaaguu aauuaaguua | 60 |
| ucuuaauuaa | gagcauaauu | auacugauuu | gucucucguu | gauagagucu aucauucugu | 120 |
| uacuaaaaau | uugacaacuc | gguuugcuga | ccuacugguu | acuguaucac uuacccgagu | 180 |
| uaacgaggga | ggaagugaag | cacagaaaug | gaacaaaaau | aaaaccuugg gguacucuuu | 240 |
| gaucuucuuu | gcaagaaugu | aaugaauauc | ccugauuacu | uucuucauau accguccguc | 300 |
| aagugccuuc | aauugcugaa | gccaaauccu | aaaucccaua | ccacaagauu acaggcauag | 360 |
| agucucgaag | cauuauuaau | aacucauugg | cgaucaaauu | aagaugaaug ucaguuuauu | 420 |
| aaaggaaaaa | guaagaaca | agaacaaaau | cauuuggcac | uuuucauacu acaaccaucg | 480 |
| acaaaauuag | cugcugccac | ugcuucuuug | acauguaaua | cggagacuc acugcuauuu | 540 |
| cauuauuugg | ucaaggcaa | aggaauuagg | agaugaagug | gauggauaug augaaagcuc | 600 |
| cuccgccacc | accuaaucaa | uacaauagca | gcaguaguac | uaauaaccuu agccaaagca | 660 |
| aagaaaucag | agaagaagaa | gagcgaaaaa | gcuugccuuc | uucuccauac aauccggcca | 720 |
| aaguuucaau | auccggauca | uggacaccaa | uaacaauacu | uauaggauca cuauacagca | 780 |
| aacgagaugc | aauuuuagcu | aagacagaag | uuucacaagc | ucauuuagag cuguuaaaga | 840 |
| agacuaauga | agcagcaaua | gaagaaacag | agaagcaauc | ucgagcuccu gagaccuggu | 900 |

| | | |
|---|---|---|
| ccuccucguu aacucgggua agugauacag uaaccaguag gucagcaaac cgaguuguca | 960 | |
| aauuuuuagu aacagaauga uagacucuau caacgagaga caaaucagua uaauuaugcu | 1020 | |
| cuuaauuaag auaacuuaau uaacuuaaca cuuucucuaa agauagugug aaacccagca | 1080 | |
| acaagaugcu c | 1091 | |

```
<210> SEQ ID NO 28
<211> LENGTH: 15791
<212> TYPE: DNA
<213> ORGANISM: Artificial Sequence
<220> FEATURE:
<223> OTHER INFORMATION: Synthetic pRNAi-GG sequence
<220> FEATURE:
<221> NAME/KEY: misc_feature
<222> LOCATION: (11788)..(11788)
<223> OTHER INFORMATION: n is a, c, g or t
```

<400> SEQUENCE: 28

| | | |
|---|---|---|
| aagctttcaa catgtggagc acgacacact tgtctactcc aaaaatatca aagatacagt | 60 | |
| ctcagaagac caaagggcaa ttgagacttt tcaacaaagg gtaatatccg gaaacctcct | 120 | |
| cggattccat tgcccagcta tctgtcactt tattgtgaag atagtggaaa aggaaggtgg | 180 | |
| ctcctacaaa tgccatcatt gcgataaagg aaaggccatc gttgaagatg cctctgccga | 240 | |
| cagtggtccc aaagatggac ccccacccac gaggagcatc gtggaaaaag aagacgttcc | 300 | |
| aaccacgtct tcaaagcaag tggattgatg tgataacatg gtggagcacg acacacttgt | 360 | |
| ctactccaaa aatatcaaag atacagtctc agaagaccaa aggcaattg agactttttca | 420 | |
| acaagggta atatccggaa acctcctcgg attccattgc ccagctatct gtcactttat | 480 | |
| tgtgaagata gtggaaaagg aaggtggctc ctacaaatgc catcattgcg ataaaggaaa | 540 | |
| ggccatcgtt gaagatgcct ctgccgacag tggtcccaaa gatggacccc cacccacgag | 600 | |
| gagcatcgtg gaaaagaag acgttccaac cacgtcttca aagcaagtgg attgatgtga | 660 | |
| tatctccact gacgtaaggg atgacgcaca atcccactat ccttcgcaag cccttcctc | 720 | |
| tatataagga agttcatttc atttggagag gacgtcgaga gttctcaaca caacatatac | 780 | |
| aaaacaaacg aatctcaagc aatcaagcat tctacttcta ttgcagcaat ttaaatcatt | 840 | |
| tcttttaaag caaagcaat tttctgaaaa ttttcaccat ttacgaacga tagccagggc | 900 | |
| ccggagtgag accaattctc gactaagttg gcagcatcac ccgacgcact ttgcgccgaa | 960 | |
| taaatacctg tgacggaaga tcacttcgca gaataaataa atcctggtgt ccctgttgat | 1020 | |
| accgggaagc cctgggccaa cttttggcga aaatgagacg ttgatcggca cgtaagaggt | 1080 | |
| tccaactttc accataatga aataagatca ctaccgggcg tatttttga gttatcgaga | 1140 | |
| ttttcaggag ctaaggaagc taaacttttg ctgacgagaa cagggactgg tgaaatgcag | 1200 | |
| tttaaggttt acacctataa aagagagagc cgttatcgtc tgtttgtgga tgtacagagt | 1260 | |
| gatattattg acacgcctgg gcgacggatg gtgatccccc tggccagtgc acgtctgctg | 1320 | |
| tcagataaag tctcccgtga actttacccg gtggtgcata tcggggatga aagctggcgc | 1380 | |
| atgatgacca ccgatatggc cagtgtgccg gtatccgtta tcggggaaga agtggctgat | 1440 | |
| ctcagccacc gcgaaaatga catcaaaaac gccattaacc tgatgttctg gggaatataa | 1500 | |
| atgtcaggct cccttataca caggtcgacg gtctcaacga gcccttggta aggaaataat | 1560 | |
| tattttcttt tttccttta gtataaaata gttaagtgat gttaattagt atgattataa | 1620 | |
| taatatagtt gttataattg tgaaaaaata atttataaat atattgttta cataaacaac | 1680 | |

-continued

```
atagtaatgt aaaaaaatat gacaagtgat gtgtaagacg aagaagataa aagttgagag    1740
taagtatatt atttttaatg aatttgatcg aacatgtaag atgatatacg gccggtaaga    1800
ggttccaact ttcaccataa tgaaataaga tcactaccgg gcgtattttt tgagttatcg    1860
agattttcag gagctaagga agctaaaatg gagaaaaaaa tcactggata taccaccgtt    1920
gatatatccc aatggcatcg taaagaacat tttgaggcat ttcagtcagt tgctcaatgt    1980
acctataacc agaccgttca gctggatatt acggcctttt taaagaccgt aaagaaaaat    2040
aagcacaagt tttatccggc ctttattcac attcttgccc gcctgatgaa tgctcatccg    2100
gaattccgta tggcaatgaa agacggtgag ctggtgatat gggatagtgt tcacccttgt    2160
tacaccgttt tccatgagca aactgaaacg ttttcatcgc tctggagtga ataccacgac    2220
gatttccggc agtttctaca catatattcg caagatgtgg cgtgttacgg tgaaaacctg    2280
gcctatttcc ctaaagggtt tattgagaat atgttttttcg tctcagccaa tccctgggtg    2340
agtttcacca gttttgattt aaacgtggcc aatatggaca acttcttcgc ccccgttttc    2400
accatgggca aatattatac gcaaggcgac aaggtgctga tgccgctggc gattcaggtt    2460
catcatgccg tctgtgatgg cttccatgtc ggcagaatgc ttaatgaatt acaacagtac    2520
tgcgatgagt ggcagggcgg ggcgtaatcg cgtggatccg gcttactaaa agccagataa    2580
cagtatgcgt atttgcgcgc tgattttttgc ggtataagaa tatatactga tatgtcggtc    2640
ccataatagt aattctagct ggtttgatga attaaatatc aatgataaaa tactatagta    2700
aaaataagaa taaataaatt aaaataatat ttttttatga ttaatagttt attatataat    2760
taaatatcta taccattact aaatatttta gtttaaaagt taataaatat tttgttagaa    2820
attccaatct gcttgtaatt tatcaataaa caaaatatta aataacaagc taaagtaaca    2880
aataatatca aactaataga aacagtaatc taatgtaaca aaacataatc taatgctaat    2940
ataacaaagc gcaagatcta tcattttata tagtattatt ttcaatcaac attcttatta    3000
atttctaaat aatacttgta gttttattaa cttctaaatg gattgactat taattaaatg    3060
aattagtcga acatgaataa acaaggtaac atgatagatc atgtcattgt gttatcattg    3120
atcttacatt tggattgatt acagttggtc tagagatttc gtctagatcg ttgagaccaa    3180
ttctcgacta agttggcagc atcacccgac gcactttgcg ccgaataaat acctgtgacg    3240
gaagatcact tcgcagaata aataaatcct ggtgtccctg ttgataccgg gaagccctgg    3300
gccaactttt ggcgaaaatg agacgttgat cggcacgtaa gaggttccaa cttttcaccat    3360
aatgaaataa gatcactacc gggcgtattt tttgagttat cgagattttc aggagctaag    3420
gaagctaaac ttttgctgac gagaacaggg actggtgaaa tgcagtttaa ggtttacacc    3480
tataaagag agagccgtta tcgtctgttt gtggatgtac agagtgatat tattgacacg    3540
cctgggcgac ggatggtgat cccctggcc agtgcacgtc tgctgtcaga taaagtctcc    3600
cgtgaacttt acccgtggt gcatatcggg gatgaaagct ggcgcatgat gaccaccgat    3660
atggccagtg tgccggtatc cgttatcggg gaagaagtgg ctgatctcag ccaccgcgaa    3720
aatgacatca aaaacgccat taacctgatg ttctggggaa tataaatgtc aggctcccctt    3780
atacacaggt tctcactccg agctcgaatt tccccgatcg ttcaaacatt tggcaataaa    3840
gtttcttaag attgaatcct gttgccggtc ttgcgatgat tatcatataa tttctgttga    3900
attacgttaa gcatgtaata attaacatgt aatgcatgac gttatttatg agatgggttt    3960
ttatgattag agtcccgcaa ttatacattt aatacgcgat agaaaacaaa atatagcgcg    4020
caaactagga taaattatcg cgcgcggtgt catctatgtt actagatcgg gaattcactg    4080
```

```
gccgtcgttt tacaacgtcg tgactgggaa aaccctggcg ttacccaact taatcgcctt    4140
gcagcacatc ccccttttcgc cagctggcgt aatagcgaag aggcccgcac cgatcgccct    4200
tcccaacagt tgcgcagcct gaatggcgcc cgctcctttc gctttcttcc cttcctttct    4260
cgccacgttc gccggctttc cccgtcaagc tctaaatcgg gggctccctt tagggttccg    4320
atttagtgct ttacggcacc tcgaccccaa aaaacttgat tgggtgatg gttcacgtag     4380
tgggccatcg ccctgataga cggtmtcgcc ctttgacgtt ggagtccacg ttctttaata    4440
gtggactctt gttccaaact ggaacaacac tcaaccctat ctcgggctat tcttttgatt    4500
tataagggat tttgccgatt tcggaaccac catcaaacag gattttcgcc tgctggggca    4560
aaccagcgtg gaccgcttgc tgcaactctc tcagggccag gcggtgaagg gcaatcagct    4620
gttgcccgtc tcactggtga aagaaaaac caccccagta cattaaaaac gtccgcaatg    4680
tgttattaag ttgtctaagc gtcaatttgt ttacaccaca atatatcctg ccaccagcca    4740
gccaacagct ccccgaccgg cagctcggca caaaatcacc actcgataca ggcagcccat    4800
cagtccggga cggcgtcagc gggagagccg ttgtaaggcg gcagactttg ctcatgttac    4860
cgatgctatt cggaagaacg gcaactaagc tgccgggttt gaaacacgga tgatctcgcg    4920
gagggtagca tgttgattgt aacgatgaca gagcgttgct gcctgtgatc aaatatcatc    4980
tccctcgcag agatccgaat tatcagcctt cttattcatt tctcgcttaa ccgtgacagg    5040
ctgtcgatct tgagaactat gccgacataa taggaaatcg ctggataaag ccgctgagga    5100
agctgagtgg cgctatttct ttagaagtga acgttgacga tatcaactcc cctatccatt    5160
gctcaccgaa tggtacaggt cggggacccg aagttccgac tgtcggcctg atgcatcccc    5220
ggctgatcga ccccagatct ggggctgaga agcccagta aggaaacaac tgtaggttcg    5280
agtcgcgaga tcccccggaa ccaaaggaag taggttaaac ccgctccgat caggccgagc    5340
cacgccaggc cgagaacatt ggttcctgta ggcatcggga ttggcggatc aaacactaaa    5400
gctactggaa cgagcagaag tcctccggcc gccagttgcc aggcggtaaa ggtgagcaga    5460
ggcacgggag gttgccactt gcgggtcagc acggttccga acgccatgga aaccgccccc    5520
gccaggcccg ctgcgacgcc gacaggatct agcgctgcgt ttggtgtcaa caccaacagc    5580
gccacgcccg cagttccgca aatagccccc aggaccgcca tcaatcgtat cgggctacct    5640
agcagagcgg cagagatgaa cacgaccatc agcggctgca cagcgcctac cgtcgccgcg    5700
accccgcccg gcaggcggta gaccgaaata acaacaagc tccagaatag cgaaatatta    5760
agtgcgccga ggatgaagat gcgcatccac cagattcccg ttggaatctg tcggacgatc    5820
atcacgagca ataaacccgc cggcaacgcc cgcagcagca taccggcgac ccctcggcct    5880
cgctgttcgg gctccacgaa aacgccggac agatgcgcct tgtgagcgtc cttggggccg    5940
tcctcctgtt tgaagaccga cagcccaatg atctcgccgt cgatgtaggc gccgaatgcc    6000
acggcatctc gcaaccgttc agcgaacgcc tccatgggct ttttctcctc gtgctcgtaa    6060
acggacccga acatctctgg agctttcttc agggccgaca atcggatctc gcggaaatcc    6120
tgcacgtcgg ccgctccaag ccgtcgaatc tgagccttaa tcacaattgt caattttaat    6180
cctctgttta tcggcagttc gtagagcgcg ccgtgcgtcc cgagcgatac tgagcgaagc    6240
aagtgcgtcg agcagtgccc gcttgttcct gaaatgccag taaagcgctg gctgctgaac    6300
ccccagccgg aactgacccc acaaggccct agcgtttgca atgcaccagg tcatcattga    6360
cccaggcgtg ttccaccagg ccgctgcctc gcaactcttc gcaggcttcg ccgacctgct    6420
```

-continued

```
cgcgccactt cttcacgcgg gtggaatccg atccgcacat gaggcggaag gtttccagct    6480
tgagcgggta cggctcccgg tgcgagctga aatagtcgaa catccgtcgg gccgtcggcg    6540
acagcttgcg gtacttctcc catatgaatt tcgtgtagtg gtcgccagca aacagcacga    6600
cgatttcctc gtcgatcagg acctggcaac gggacgtttt cttgccacgg tccaggacgc    6660
ggaagcggtg cagcagcgac accgattcca ggtgcccaac gcggtcggac gtgaagccca    6720
tcgccgtcgc ctgtaggcgc gacaggcatt cctcggcctt cgtgtaatac cggccattga    6780
tcgaccagcc caggtcctgg caaagctcgt agaacgtgaa ggtgatcggc tcgccgatag    6840
gggtgcgctt cgcgtactcc aacacctgct gccacaccag ttcgtcatcg tcggcccgca    6900
gctcgacgcc ggtgtaggtg atcttcacgt ccttgttgac gtggaaaatg accttgtttt    6960
gcagcgcctc gcgcgggatt ttcttgttgc gcgtggtgaa cagggcagag cgggccgtgt    7020
cgtttggcat cgctcgcatc gtgtccggcc acggcgcaat atcgaacaag gaaagctgca    7080
tttccttgat ctgctgcttc gtgtgtttca gcaacgcggc ctgcttggcc tcgctgacct    7140
gttttgccag gtcctcgccg gcggtttttc gcttcttggt cgtcatagtt cctcgcgtgt    7200
cgatggtcat cgacttcgcc aaacctgccg cctcctgttc gagacgacgc gaacgctcca    7260
cggcggccga tggcgcgggc agggcagggg gagccagttg cacgctgtcg cgctcgatct    7320
tggccgtagc ttgctggacc atcgagccga cggactggaa ggtttcgcgg ggcgcacgca    7380
tgacggtgcg gcttgcgatg gtttcggcat cctcggcgga aaaccccgcg tcgatcagtt    7440
cttgcctgta tgccttccgg tcaaacgtcc gattcattca ccctccttgc gggattgccc    7500
cgactcacgc cggggcaatg tgcccttatt cctgatttga cccgcctggt gccttggtgt    7560
ccagataatc caccttatcg gcaatgaagt cggtcccgta gaccgtctgg ccgtccttct    7620
cgtacttggt attccgaatc ttgccctgca cgaataccag cgacccttg cccaaatact    7680 tgccgtgggc ctcggcctga gagccaaaac acttgatgcg gaagaagtcg gtgcgctcct    7740
gcttgtcgcc ggcatcgttg cgccacatct aggtactaaa acaattcatc cagtaaaata    7800 taatattta ttttctccca atcaggcttg atccccagta agtcaaaaaa tagctcgaca    7860
tactgttctt ccccgatatc ctccctgatc gaccggacgc agaaggcaat gtcataccac    7920
ttgtccgccc tgccgcttct cccaagatca ataaagccac ttactttgcc atctttcaca    7980
aagatgttgc tgtctcccag gtcgccgtgg gaaaagacaa gttcctcttc gggcttttcc    8040
gtctttaaaa aatcatacag ctcgcgcgga tctttaaatg gagtgtcttc ttcccagttt    8100
tcgcaatcca catcggccag atcgttattc agtaagtaat ccaattcggc taagcggctg    8160
tctaagctat tcgtataggg acaatccgat atgtcgatgg agtgaaagag cctgatgcac    8220
tccgcataca gctcgataat cttttcaggg ctttgttcat cttcatactc ttccgagcaa    8280
aggacgccat cggcctcact catgagcaga ttgctccagc catcatgccg ttcaaagtgc    8340
aggacctttg gaacaggcag ctttccttcc agccatagca tcatgtcctt ttcccgttcc    8400
acatcatagg tggtcccttt ataccggctg tccgtcattt ttaaatatag gttttcattt    8460
tctcccacca gcttatatac cttagcagga gacattcctt ccgtatcttt tacgcagcgg    8520 tattttcga tcagtttttt caattccggt gatattctca tttagccat ttattatttc    8580 cttcctcttt tctacagtat ttaaagatac cccaagaagc taattataac aagacgaact    8640
ccaattcact gttccttgca ttctaaaacc ttaaatacca gaaaacagct ttttcaaagt    8700
tgttttcaaa gttggcgtat aacatagtat cgacggagcc gattttgaaa ccacaattat    8760
gggtgatgct gccaacttac tgatttagtg tatgatggtg tttttgaggt gctccagtgg    8820
```

-continued

```
cttctgtgtc tatcagctgt ccctcctgtt cagctactga cggggtggtg cgtaacggca    8880
aaagcaccgc cggacatcag cgctatctct gctctcactg ccgtaaaaca tggcaactgc    8940
agttcactta caccgcttct caacccggta cgcaccagaa aatcattgat atggccatga    9000
atggcgttgg atgccgggca acagcccgca ttatgggcgt tggcctcaac acgattttac    9060
gtcacttaaa aaactcaggc cgcagtcggt aacctcgcgc atacagccgg gcagtgacgt    9120
catcgtctgc gcggaaatgg acgaacagtg gggctatgtc ggggctaaat cgcgccagcg    9180
ctggctgttt tacgcgtatg acagtctccg gaagacggtt gttgcgcacg tattcggtga    9240
acgcactatg gcgacgctgg ggcgtcttat gagcctgctg tcacccttg acgtggtgat    9300
atggatgacg gatggctggc cgctgtatga atcccgcctg aagggaaagc tgcacgtaat    9360
cagcaagcga tatacgcagc gaattgagcg gcataacctg aatctgaggc agcacctggc    9420
acggctggga cggaagtcgc tgtcgttctc aaaatcggtg gagctgcatg acaaagtcat    9480
cgggcattat ctgaacataa aacactatca ataagttgga gtcattaccc aattatgata    9540
gaatttacaa gctataaggt tattgtcctg ggtttcaagc attagtccat gcaagttttt    9600
atgctttgcc cattctatag atatattgat aagcgcgctg cctatgcctt gccccctgaa    9660
atccttacat acggcgatat cttctatata aaagatatat tatcttatca gtattgtcaa    9720
tatattcaag gcaatctgcc tcctcatcct cttcatcctc ttcgtcttgg tagcttttta    9780
aatatggcgc ttcatagagt aattctgtaa aggtccaatt ctcgttttca tacctcggta    9840
taatcttacc tatcacctca aatggttcgc tgggtttatc gcaccccga acacgagcac    9900
ggcacccgcg accactatgc caagaatgcc caaggtaaaa attgccggcc ccgccatgaa    9960
gtccgtgaat gccccgacgg ccgaagtgaa gggcaggccg ccacccaggc cgccgccctc    10020
actgcccggc acctggtcgc tgaatgtcga tgccagcacc tgcggcacgt caatgcttcc    10080
gggcgtcgcg ctcgggctga tcgcccatcc cgttactgcc ccgatcccgg caatggcaag    10140
gactgccagc gctgccattt ttggggtgag gccgttcgcg ccgaggggc gcagcccctg    10200
gggggatggg aggcccgcgt tagcgggccg ggagggttcg agaaggggg gcacccccct    10260
tcggcgtgcg cggtcacgcg cacagggcgc agccctggtt aaaaacaagg tttataaata    10320
ttggtttaaa agcaggttaa aagacaggtt agcggtggcc gaaaaacggg cggaaaccct    10380
tgcaaatgct ggattttctg cctgtggaca gccccctcaaa tgtcaatagg tgcgcccctc    10440
atctgtcagc actctgcccc tcaagtgtca aggatcgcgc ccctcatctg tcagtagtcg    10500
cgcccctcaa gtgtcaatac cgcagggcac ttatccccag gcttgtccac atcatctgtg    10560
ggaaactcgc gtaaaatcag gcgttttcgc cgatttgcga ggctggccag ctccacgtcg    10620
ccggccgaaa tcgagcctgc ccctcatctg tcaacgccgc gccgggtgag tcggcccctc    10680
aagtgtcaac gtccgcccct catctgtcag tgagggccaa gttttccgcg aggtatccac    10740
aacgccggcg gccgcggtgt ctcgcacacg gcttcgacgg cgtttctggc gcgtttgcag    10800
ggccatagac ggccgccagc ccagcggcga gggcaaccag cccggtgagc gtcgcaaagg    10860
cgctcggtct tgccttgctc gtcggtgatg tacttcacca gctccgcgaa gtcgctcttc    10920
ttgatggagc gcatgggac gtgcttggca atcacgcgca ccccccggcc gttttagcgg    10980
ctaaaaaagt catggctctg ccctcgggcg gaccacgccc atcatgacct tgccaagctc    11040
gtcctgcttc tcttcgatct tcgccagcag ggcgaggatc gtggcatcac cgaaccgcgc    11100
cgtgcgcggg tcgtcggtga gccagagttt cagcaggccg cccaggcggc ccaggtcgcc    11160
```

```
attgatgcgg gccagctcgc ggacgtgctc atagtccacg acgcccgtga ttttgtagcc   11220
ctggccgacg gccagcaggt aggccgacag gctcatgccg gccgccgccg ccttttcctc   11280
aatcgctctt cgttcgtctg gaaggcagta caccttgata ggtgggctgc ccttcctggt   11340
tggcttggtt tcatcagcca tccgcttgcc ctcatctgtt acgccggcgg tagccggcca   11400
gcctcgcaga gcaggattcc cgttgagcac cgccaggtgc gaataaggga cagtgaagaa   11460
ggaacacccg ctcgcgggtg ggcctacttc acctatcctg cccggctgac gccgttggat   11520
acaccaagga aagtctacac gaacccttg gcaaaatcct gtatatcgtg cgaaaaagga    11580
tggatatacc gaaaaaatcg ctataatgac cccgaagcag ggttatgcag cggaaaagcg   11640
ccacgcttcc cgaagggaga aaggcggaca ggtatccggt aagcggcagg gtcggaacag   11700
gagagcgcac gagggagctt ccaggggaa acgcctggta tctttatagt cctgtcgggt     11760
ttcgccacct ctgacttgag cgtcgatntt gtgatgctcg tcagggggc ggagcctatg    11820 gaaaaacgcc agcaacgcgg cctmtacggt tcctggcctt ttgctggcct tttgctcaca   11880
tgttctttcc tgcgttatcc cctgattctg tggataaccg tattaccgcc tttgagtgag   11940
ctgataccgc tcgccgcagc cgaacgaccg agcgcagcga gtcagtgagc gaggaagcgg   12000
aagagcgcca gaaggccgcc agagaggccg agcgcggccg tgaggcttgg acgctagggc   12060
agggcatgaa aaagcccgta gcgggctgct acgggcgtct gacgcggtgg aaaggggag    12120 gggatgttgt ctacatggct ctgctgtagt gagtgggttg cgctccggca gcggtcctga   12180
tcaatcgtca ccctttctcg gtccttcaac gttcctgaca acgagcctcc ttttcgccaa   12240
tccatcgaca atcaccgcga gtccctgctc gaacgctgcg tccggaccgg cttcgtcgaa   12300
ggcgtctatc gcggcccgca acagcggcga gagcggagcc tgttcaacgg tgccgccgcg   12360
ctcgccggca tcgctgtcgc cggcctgctc ctcaagcacg gccccaacag tgaagtagct   12420
gattgtcatc agcgcattga cggcgtcccc ggccgaaaaa cccgcctcgc agaggaagcg   12480
aagctgcgcg tcgccgtttt ccatctgcgg tgcgcccgt cgcgtgccgg catggatgcg     12540
cgcgccatcg cggtaggcga gcagcgcctg cctgaagctg cgggcattcc cgatcagaaa   12600
tgagcgccag tcgtcgtcgg ctctcggcac cgaatgcgta tgattctccg ccagcatggc   12660
ttcggccagt gcgtcgagca gcgcccgctt gttcctgaag tgccagtaaa gcgccggctg   12720
ctgaaccccc aaccgttccg ccagtttgcg tgtcgtcaga ccgtctacgc cgacctcgtt   12780
caacaggtcc agggcggcac ggatcactgt attcggctgc aactttgtca tgcttgacac   12840
tttatcactg ataaacataa tatgtccacc aacttatcag tgataaagaa tccgcgcgtt   12900
caatcggacc agcggaggct ggtccggagg ccagacgtga aacccaacat acccctgatc   12960
gtaattctga gcactgtcgc gctcgacgct gtcggcatcg gcctgattat gccggtgctg   13020
ccgggcctcc tgcgcgatct ggttcactcg aacgacgtca ccgcccacta tggcattctg   13080
ctggcgctgt atgcgttggt gcaatttgcc tgcgcacctg tgctgggcgc gctgtcggat   13140
cgtttcgggc ggcggccaat cttgctcgtc tcgctggccg cgccagatc tggggaaccc    13200 tgtggttggc atgcacatac aaatggacga acggataaac ctttttcacgc ccttttaaat   13260 atccgattat tctaataaac gctcttttct cttaggttta cccgccaata tatcctgtca   13320
aacactgata gtttaaactg aaggcgggaa acgacaatct gatcatgagc ggagaattaa   13380
gggagtcacg ttatgacccc cgccgatgac gcgggacaag ccgttttacg tttggaactg   13440
acagaaccgc aacgttgaag gagccactca gccgcgggtt tctggagttt aatgagctaa   13500
gcacatacgt cagaaaccat tattgcgcgt tcaaaagtcg cctaaggtca ctatcagcta   13560
```

```
gcaaatattt cttgtcaaaa atgctccact gacgttccat aaattccccct cggtatccaa    13620 ttagagtctc atattcactc tcaatccaaa taatctgcac cggatctgga tcgtttcgca    13680
tgattgaaca agatggattg cacgcaggtt ctccggccgc ttgggtggag aggctattcg    13740
gctatgactg ggcacaacag acaatcggct gctctgatgc cgccgtgttc cggctgtcag    13800
cgcaggggcg cccggttctt tttgtcaaga ccgacctgtc cggtgccctg aatgaactgc    13860
aggacgaggc agcgcggcta tcgtggctgg ccacgacggg cgttccttgc gcagctgtgc    13920
tcgacgttgt cactgaagcg ggaagggact ggctgctatt gggcgaagtg ccggggcagg    13980
atctcctgtc atctcacctt gctcctgccg agaaagtatc catcatggct gatgcaatgc    14040
ggcggctgca tacgcttgat ccggctacct gcccattcga ccaccaagcg aaacatcgca    14100
tcgagcgagc acgtactcgg atggaagccg gtcttgtcga tcaggatgat ctggacgaag    14160
agcatcaggg gctcgcgcca gccgaactgt tcgccaggct caaggcgcgc atgcccgacg    14220
gcgatgatct cgtcgtgacc catggcgatg cctgcttgcc gaatatcatg gtggaaaatg    14280
gccgcttttc tggattcatc gactgtggcc ggctgggtgt ggcggaccgc tatcaggaca    14340
tagcgttggc tacccgtgat attgctgaag agcttggcgg cgaatgggct gaccgcttcc    14400
tcgtgcttta cggtatcgcc gctcccgatt cgcagcgcat cgccttctat cgccttcttg    14460
acgagttctt ctgagcggga ctctggggtt cgaaatgacc gaccaagcga cgcccaacct    14520
gccatcacga gatttcgatt ccaccgccgc cttctatgaa aggttgggct tcggaatcgt    14580
tttccgggac gccggctgga tgatcctcca gcgcggggat ctcatgctgg agttcttcgc    14640
ccacgggatc tctgcggaac aggcggtcga aggtgccgat atcattacga cagcaacggc    14700
cgacaagcac aacgccacga tcctgagcga caatatgatc gggcccggcg tccacatcaa    14760
cggcgtcggc ggcgactgcc caggcaagac cgagatgcac cgcgatatct tgctgcgttc    14820
ggatattttc gtggagttcc cgccacagac ccggatgatc cccgatcgtt caaacatttg    14880
gcaataaagt ttcttaagat tgaatcctgt tgccggtctt gcgatgatta tcatataatt    14940
tctgttgaat tacgttaagc atgtaataat taacatgtaa tgcatgacgt tatttatgag    15000
atgggttttt atgattagag tcccgcaatt atacatttaa tacgcgatag aaaacaaaat    15060
atagcgcgca aactaggata aattatcgcg cgcggtgtca tctatgttac tagatcgggc    15120
ctcctgtcaa tgctggcggc ggctctggtg gtggttctgg tggcggctct gagggtggtg    15180
gctctgaggg tggcggttct gagggtggcg gctctgaggg aggcggttcc ggtggtggct    15240
ctggttccgg tgattttgat tatgaaaaga tggcaaacgc taataagggg gctatgaccg    15300
aaaatgccga tgaaaacgcg ctacagtctg acgctaaagg caaacttgat tctgtcgcta    15360
ctgattacgg tgctgctatc gatggtttca ttggtgacgt ttccggcctt gctaatggta    15420
atggtgctac tggtgatttt gctggctcta attcccaaat ggctcaagtc ggtgacggtg    15480
ataattcacc tttaatgaat aatttccgtc aatatttacc ttccctccct caatcggttg    15540
aatgtcgccc ttttgtcttt ggcccaatac gcaaaccgcc tctccccgcg cgttggccga    15600
ttcattaatg cagctggcac gacaggtttc ccgactggaa agcgggcagt gagcgcaacg    15660
caattaatgt gagttagctc actcattagg caccccaggc tttacacttt atgcttccgg    15720
ctcgtatgtt gtgtggaatt gtgagcggat aacaatttca cacaggaaac agctatgacc    15780
atgattacgc c                                                        15791
```

<210> SEQ ID NO 29

<211> LENGTH: 16178
<212> TYPE: DNA
<213> ORGANISM: Artificial Sequence
<220> FEATURE:
<223> OTHER INFORMATION: Synthetic pRNAi-GG with SEQ_14 inserts

<400> SEQUENCE: 29

| | | | | | | |
|---|---|---|---|---|---|---|
| aagcttttcaa | catgtggagc | acgacacact | tgtctactcc | aaaaatatca | aagatacagt | 60 |
| ctcagaagac | caaagggcaa | ttgagacttt | tcaacaaagg | gtaatatccg | gaaacctcct | 120 |
| cggattccat | tgcccagcta | tctgtcactt | tattgtgaag | atagtggaaa | aggaaggtgg | 180 |
| ctcctacaaa | tgccatcatt | gcgataaagg | aaaggccatc | gttgaagatg | cctctgccga | 240 |
| cagtggtccc | aaagatggac | ccccacccac | gaggagcatc | gtggaaaaag | aagacgttcc | 300 |
| aaccacgtct | tcaaagcaag | tggattgatg | tgataacatg | gtggagcacg | acacacttgt | 360 |
| ctactccaaa | aatatcaaag | atacagtctc | agaagaccaa | agggcaattg | agacttttca | 420 |
| acaaagggta | atatccggaa | acctcctcgg | attccattgc | ccagctatct | gtcactttat | 480 |
| tgtgaagata | gtggaaaagg | aaggtggctc | ctacaaatgc | catcattgcg | ataaaggaaa | 540 |
| ggccatcgtt | gaagatgcct | ctgccgacag | tggtcccaaa | gatggacccc | acccacgag | 600 |
| gagcatcgtg | gaaaaagaag | acgttccaac | cacgtcttca | aagcaagtgg | attgatgtga | 660 |
| tatctccact | gacgtaaggg | atgacgcaca | atcccactat | ccttcgcaag | acccttcctc | 720 |
| tatataagga | agttcatttc | atttggagag | acgtcgaga | gttctcaaca | caacatatac | 780 |
| aaaacaaacg | aatctcaagc | aatcaagcat | tctacttcta | ttgcagcaat | ttaaatcatt | 840 |
| tcttttaaag | caaaagcaat | tttctgaaaa | ttttcaccat | ttacgaacga | tagccagggc | 900 |
| ccggaggtgc | aactcgctga | tcattatcaa | caaaatactc | caattggcga | tggccccgca | 960 |
| gagaggccgc | ttcgtaaaat | ctcaactgct | ttcaaagaac | tagcagccac | cgtgagctcg | 1020 |
| ccgagtcctg | aagtctccgt | ggctcagttc | tctcacgctt | gctctctcgt | ctcgcctctc | 1080 |
| tttggttgcc | tcgggatcgc | cttcaagata | ttgaggcaaa | ctgtgtaagg | aaagctggta | 1140 |
| gtcatactag | aaaccttttg | agggtagagc | taatggttga | tctcatgtcg | acgctggagg | 1200 |
| atcgcctcca | ctctcaaaga | gagtggtggg | agaagaagag | aaactggagc | tggaaagaag | 1260 |
| agataaaagc | ttcagaagga | agagcatcac | caccaactct | ggtgctcctg | tatggaacaa | 1320 |
| caactcctcc | atgaccgttg | gacccagagg | tccccacgcg | cttaaaccaa | accctaaatc | 1380 |
| tcacattcaa | gaaaactgaa | cctcacttgt | gctgacttcc | tcagagctcc | aggtgttcaa | 1440 |
| actccggtca | ttcctgtccg | ctgcgccgag | aaagttccta | tccctaccaa | atcctacact | 1500 |
| ggaataagaa | caaatgtatc | ctagaggagc | aaccaatgtg | cgttgtgcgt | tatgtcacat | 1560 |
| tgtcaacatg | gttcctcttc | atcctaccct | tacggtgcat | catctgttaa | atgcgctgtt | 1620 |
| tgccagtttg | ttactaacgt | taacaaaact | taccctttaa | tttatttgca | ctactggaaa | 1680 |
| actacctgtt | ccatggccaa | cacttgtcac | tactttctct | tatgacgagc | ccttggtaag | 1740 |
| gaaataatta | ttttctttt | tccttttagt | ataaaatagt | taagtgatgt | taattagtat | 1800 |
| gattataata | atatagttgt | tataattgtg | aaaaaataat | ttataaatat | attgtttaca | 1860 |
| taaacaacat | agtaatgtaa | aaaaatatga | caagtgatgt | gtaagacgaa | gaagataaaa | 1920 |
| gttgagagta | agtatattat | ttttaatgaa | tttgatcgaa | catgtaagat | gatatacggc | 1980 |
| cggtaagagg | ttccaacttt | caccataatg | aaataagatc | actaccgggc | gtatttttg | 2040 |
| agttatcgag | attttcagga | gctaaggaag | ctaaaatgga | gaaaaaatc | actggatata | 2100 |
| ccaccgttga | tatatcccaa | tggcatcgta | aagaacattt | tgaggcattt | cagtcagttg | 2160 |

```
ctcaatgtac ctataaccag accgttcagc tggatattac ggccttttta aagaccgtaa    2220
agaaaaataa gcacaagttt tatccggcct ttattcacat tcttgcccgc ctgatgaatg    2280
ctcatccgga attccgtatg gcaatgaaag acggtgagct ggtgatatgg gatagtgttc    2340
acccttgtta caccgttttc catgagcaaa ctgaaacgtt ttcatcgctc tggagtgaat    2400
accacgacga tttccggcag tttctacaca tatattcgca agatgtggcg tgttacggtg    2460
aaaacctggc ctatttccct aaagggttta ttgagaatat gttttcgtc tcagccaatc    2520
cctgggtgag tttcaccagt tttgatttaa acgtggccaa tatggacaac ttcttcgccc    2580
ccgttttcac catgggcaaa tattatacgc aaggcgacaa ggtgctgatg ccgctggcga    2640
ttcaggttca tcatgccgtc tgtgatggct ccatgtcgg cagaatgctt aatgaattac    2700
aacagtactg cgatgagtgg cagggcgggg cgtaatcgcg tggatccggc ttactaaaag    2760
ccagataaca gtatgcgtat ttgcgcgctg atttttgcgg tataagaata tatactgata    2820
tgtcggtccc ataatagtaa ttctagctgg tttgatgaat aaatatcaa tgataaaata    2880
ctatagtaaa aataagaata aataaattaa ataatatttt tttatgatt aatagtttat    2940
tatataatta aatatctata ccattactaa atattttagt ttaaaagtta ataaatattt    3000
tgttagaaat tccaatctgc ttgtaattta tcaataaaca aaatattaaa taacaagcta    3060
aagtaacaaa taatatcaaa ctaatagaaa cagtaatcta atgtaacaaa acataatcta    3120
atgctaatat aacaaagcgc aagatctatc attttatata gtattatttt caatcaacat    3180
tcttattaat ttctaaataa tacttgtagt tttattaact tctaaatgga ttgactatta    3240
attaaatgaa ttagtcgaac atgaataaac aaggtaacat gatagatcat gtcattgtgt    3300
tatcattgat cttacatttg gattgattac agttggtcta gagatttcgt ctagatcgtc    3360
ataagagaaa gtagtgacaa gtgttggcca tggaacaggt agttttccag tagtgcaaat    3420
aaatttaagg gtaagttttg ttaacgttag taacaaactg gcaaacagcg catttaacag    3480
atgatgcacc gtaagggtag gatgaagagg aaccatgttg acaatgtgac ataacgcaca    3540
acgcacattg gttgctcctc taggatacat ttgttcttat tccagtgtag gatttggtag    3600
ggataggaac tttctcggcg cagcggacag gaatgaccgg agtttgaaca cctggagctc    3660
tgaggaagtc agcacaagtg aggttcagtt ttcttgaatg tgagatttag ggtttggttt    3720
aagcgcgtgg ggacctctgg gtccaacggt catggaggag ttgttgttcc atacaggagc    3780
accagagttg gtggtgatgc tcttccttct gaagctttta tctcttcttt ccagctccag    3840
tttctcttct tctcccacca ctctctttga gagtggaggc gatcctccag cgtcgacatg    3900
agatcaacca ttagctctac cctcaaaagg tttctagtat gactaccagc tttccttaca    3960
cagtttgcct caatatcttg aaggcgatcc cgaggcaacc aaagagaggc gagacgagag    4020
agcaagcgtg agagaactga gccacggaga cttcaggact cggcgagctc acggtggctg    4080
ctagttcttt gaaagcagtt gagatttac gaagcggcct ctctgcgggg ccatcgccaa    4140
ttggagtatt ttgttgataa tgatcagcga gttgcacctc cgagctcgaa tttccccgat    4200
cgttcaaaca tttggcaata aagtttctta agattgaatc ctgttgccgg tcttgcgatg    4260
attatcatat aatttctgtt gaattacgtt aagcatgtaa taattaacat gtaatgcatg    4320
acgttattta tgagatgggt ttttatgatt agagtcccgc aattatacat ttaatacgcg    4380
atagaaaaca aaatatagcg cgcaaactag gataaaattat cgcgcgcggt gtcatctatg    4440
ttactagatc gggaattcac tggccgtcgt tttacaacgt cgtgactggg aaaaccctgg    4500
```

```
cgttacccaa cttaatcgcc ttgcagcaca tcccccttc gccagctggc gtaatagcga    4560
agaggcccgc accgatcgcc cttcccaaca gttgcgcagc ctgaatggcg cccgctcctt    4620
tcgctttctt cccttccttt ctcgccacgt tcgccggctt tccccgtcaa gctctaaatc    4680
gggggctccc tttagggttc cgatttagtg ctttacggca cctcgacccc aaaaaacttg    4740
atttgggtga tggttcacgt agtgggccat cgccctgata cacggttttt cgccctttga    4800
cgttggagtc cacgttcttt aatagtggac tcttgttcca aactggaaca acactcaacc    4860
ctatctcggg ctattctttt gatttataag ggattttgcc gatttcggaa ccaccatcaa    4920
acaggatttt cgcctgctgg ggcaaaccag cgtggaccgc ttgctgcaac tctctcaggg    4980
ccaggcggtg aagggcaatc agctgttgcc cgtctcactg gtgaaaagaa aaaccacccc    5040
agtacattaa aaacgtccgc aatgtgttat aagttgtct aagcgtcaat ttgtttacac    5100
cacaatatat cctgccacca gccagccaac agctccccga ccggcagctc ggcacaaaat    5160
caccactcga tacaggcagc ccatcagtcc gggacggcgt cagcgggaga gccgttgtaa    5220
ggcggcagac tttgctcatg ttaccgatgc tattcggaag aacggcaact aagctgccgg    5280
gtttgaaaca cggatgatct cgcggagggt agcatgttga ttgtaacgat gacagagcgt    5340
tgctgcctgt gatcaaatat catctccctc gcagagatcc gaattatcag ccttcttatt    5400
catttctcgc ttaaccgtga caggctgtcg atcttgagaa ctatgccgac ataataggaa    5460
atcgctggat aaagccgctg aggaagctga gtggcgctat ttctttagaa gtgaacgttg    5520
acgatatcaa ctcccctatc cattgctcac cgaatggtac aggtcgggga cccgaagttc    5580
cgactgtcgg cctgatgcat ccccggctga tcgaccccag atctggggct gagaaagccc    5640
agtaaggaaa caactgtagg ttcgagtcgc gagatccccc ggaaccaaag gaagtaggtt    5700
aaacccgctc cgatcaggcc gagccacgcc aggccgagaa cattggttcc tgtaggcatc    5760
gggattggcg gatcaaacac taaagctact ggaacgagca gaagtcctcc ggccgccagt    5820
tgccaggcgg taaaggtgag cagaggcacg ggaggttgcc acttgcgggt cagcacggtt    5880
ccgaacgcca tggaaaccgc ccccgccagg cccgctgcga cgccgacagg atctagcgct    5940
gcgtttggtg tcaacaccaa cagcgccacg cccgcagttc cgcaaatagc ccccaggacc    6000
gccatcaatc gtatcgggct acctagcaga gcggcagaga tgaacacgac catcagcggc    6060
tgcacagcgc ctaccgtcgc gcgaccccg ccggcaggc ggtagaccga ataaacaac    6120
aagctccaga atagcgaaat attaagtgcg ccgaggatga agatgcgcat ccaccagatt    6180
cccgttggaa tctgtcggac gatcatcacg agcaataaac ccgccggcaa cgcccgcagc    6240
agcataccgg cgacccctcg gcctcgctgt tcgggctcca cgaaaacgcc ggacagatgc    6300
gccttgtgag cgtccttggg gccgtcctcc tgtttgaaga ccgacagccc aatgatctcg    6360
ccgtcgatgt aggcgccgaa tgccacggca tctcgcaacc gttcagcgaa cgcctccatg    6420
ggcttttct cctcgtgctc gtaaacggac ccgaacatct ctggagcttt cttcagggcc    6480
gacaatcgga tctcgcggaa atcctgcacg tcggccgctc caagccgtcg aatctgagcc    6540
ttaatcacaa ttgtcaattt taatcctctg tttatcggca gttcgtagag cgcgccgtgc    6600
gtcccgagcg atactgagcg aagcaagtgc gtcgagcagt gcccgcttgt tcctgaaatg    6660
ccagtaaagc gctggctgct gaaccccag ccggaactga cccacaagg ccctagcgtt    6720
tgcaatgcac caggtcatca ttgacccagg cgtgttccac caggccgctg cctcgcaact    6780
cttcgcaggc ttcgccgacc tgctcgcgcc acttcttcac gcgggtggaa tccgatccgc    6840
acatgaggcg gaaggtttcc agcttgagcg ggtacggctc ccggtgcgag ctgaaatagt    6900
```

-continued

```
cgaacatccg tcgggccgtc ggcgacagct tgcggtactt ctcccatatg aatttcgtgt    6960
agtggtcgcc agcaaacagc acgacgattt cctcgtcgat caggacctgg caacgggacg    7020
ttttcttgcc acggtccagg acgcggaagc ggtgcagcag cgacaccgat tccaggtgcc    7080
caacgcggtc ggacgtgaag cccatcgccg tcgcctgtag gcgcgacagg cattcctcgg    7140
ccttcgtgta ataccggcca ttgatcgacc agcccaggtc ctggcaaagc tcgtagaacg    7200
tgaaggtgat cggctcgccg ataggggtgc gcttcgcgta ctccaacacc tgctgccaca    7260
ccagttcgtc atcgtcggcc cgcagctcga cgccggtgta ggtgatcttc acgtccttgt    7320
tgacgtggaa aatgaccttg ttttgcagcg cctcgcgcgg gattttcttg ttgcgcgtgg    7380
tgaacagggc agagcgggcc gtgtcgtttg gcatcgctcg catcgtgtcc ggccacggcg    7440
caatatcgaa caaggaaagc tgcatttcct tgatctgctg cttcgtgtgt ttcagcaacg    7500
cggcctgctt ggcctcgctg acctgttttg ccaggtcctc gccggcggtt tttcgcttct    7560
tggtcgtcat agttcctcgc gtgtcgatgg tcatcgactt cgccaaacct gccgcctcct    7620
gttcgagacg acgcgaacgc tccacggcgg ccgatggcgc gggcagggca ggggagcca    7680 gttgcacgct gtcgcgctcg atcttggccg tagcttgctg gaccatcgag ccgacggact    7740
ggaaggtttc gcgggcgca cgcatgacgg tgcggcttgc gatggtttcg gcatcctcgg    7800
cggaaaaccc cgcgtcgatc agttcttgcc tgtatgcctt ccggtcaaac gtccgattca    7860
ttcaccctcc ttgcgggatt gccccgactc acgccgggc aatgtgccct tattcctgat    7920
ttgacccgcc tggtgccttg gtgtccagat aatccacctt atcggcaatg aagtcggtcc    7980
cgtagaccgt ctggccgtcc ttctcgtact tggtattccg aatcttgccc tgcacgaata    8040
ccagcgaccc cttgcccaaa tacttgccgt gggcctcggc ctgagagcca aaacacttga    8100
tgcggaagaa gtcggtgcgc tcctgcttgt cgccggcatc gttgcgccac atctaggtac    8160
taaaacaatt catccagtaa aatataatat tttattttct cccaatcagg cttgatcccc    8220
agtaagtcaa aaaatagctc gacatactgt tcttccccga tatcctccct gatcgaccgg    8280
acgcagaagg caatgtcata ccacttgtcc gccctgccgc ttctcccaag atcaataaag    8340
ccacttactt tgccatcttt cacaaagatg ttgctgtctc ccaggtcgcc gtgggaaaag    8400
acaagttcct cttcgggctt ttccgtcttt aaaaaatcat acagctcgcg cggatcttta    8460
aatggagtgt cttcttccca gttttcgcaa tccacatcgg ccagatcgtt attcagtaag    8520
taatccaatt cggctaagcg gctgtctaag ctattcgtat agggacaatc cgatatgtcg    8580
atggagtgaa agagcctgat gcactccgca tacagctcga taatcttttc agggctttgt    8640
tcatcttcat actcttccga gcaaaggacg ccatcggcct cactcatgag cagattgctc    8700
cagccatcat gccgttcaaa gtgcaggacc tttggaacag gcagctttcc ttccagccat    8760
agcatcatgt ccttttcccg ttccacatca taggtggtcc ctttataccg gctgtccgtc    8820 attttaaat ataggttttc atttttctccc accagcttat ataccttagc aggagacatt    8880
ccttccgtat cttttacgca gcggtatttt tcgatcagtt ttttcaattc cggtgatatt    8940
ctcattttag ccatttatta tttccttcct cttttctaca gtatttaaag atacccaag    9000 aagctaatta taacaagacg aactccaatt cactgttcct tgcattctaa aaccttaaat    9060
accagaaaac agcttttttca aagttgtttt caaagttggc gtataacata gtatcgacgg    9120
agccgatttt gaaaccacaa ttatgggtga tgctgccaac ttactgattt agtgtatgat    9180
ggtgtttttg aggtgctcca gtggcttctg tgtctatcag ctgtccctcc tgttcagcta    9240
```

```
ctgacggggt ggtgcgtaac ggcaaaagca ccgccggaca tcagcgctat ctctgctctc    9300
actgccgtaa aacatggcaa ctgcagttca cttacaccgc ttctcaaccc ggtacgcacc    9360
agaaaatcat tgatatggcc atgaatggcg ttggatgccg ggcaacagcc cgcattatgg    9420
gcgttggcct caacacgatt ttacgtcact taaaaaactc aggccgcagt cggtaacctc    9480
gcgcatacag ccgggcagtg acgtcatcgt ctgcgcggaa atggacgaac agtggggcta    9540
tgtcggggct aaatcgcgcc agcgctggct gttttacgcg tatgacagtc tccgaaagac    9600
ggttgttgcg cacgtattcg gtgaacgcac tatggcgacg ctgggcgtc ttatgagcct    9660 gctgtcaccc tttgacgtgg tgatatggat acggatggc tggccgctgt atgaatcccg    9720
cctgaaggga agctgcacg taatcagcaa gcgatatacg cagcgaattg agcggcataa    9780
cctgaatctg aggcagcacc tggcacggct gggacggaag tcgctgtcgt tctcaaaatc    9840
ggtggagctg catgacaaag tcatcgggca ttatctgaac ataaaacact atcaataagt    9900
tggagtcatt acccaattat gatagaattt acaagctata aggttattgt cctgggtttc    9960
aagcattagt ccatgcaagt ttttatgctt tgcccattct atagatatat tgataagcgc   10020
gctgcctatg ccttgccccc tgaaatcctt acatacggcg atatcttcta tataaaagat   10080
atattatctt atcagtattg tcaatatatt caaggcaatc tgcctcctca tcctcttcat   10140
cctcttcgtc ttggtagctt tttaaatatg gcgcttcata gagtaattct gtaaaggtcc   10200
aattctcgtt ttcatacctc ggtataatct tacctatcac ctcaaatggt tcgctggggtt   10260 tatcgcaccc ccgaacacga gcacggcacc cgcgaccact atgccaagaa tgcccaaggt   10320
aaaaattgcc ggccccgcca tgaagtccgt gaatgccccg acggccgaag tgaagggcag   10380
gccgccaccc aggccgccgc cctcactgcc cggcacctgg tcgctgaatg tcgatgccag   10440
cacctgcgga acgtcaatgc ttccgggcgt gcgctcggg ctgatcgccc atcccgttac   10500
tgccccgatc ccggcaatgg caaggactgc cagcgctgcc atttttgggg tgaggccgtt   10560
cgcggccgag gggcgcagcc cctgggggga tgggaggccc gcgttagcgg gccggggaggg   10620 ttcgagaagg gggggcaccc cccttcggcg tgcgcggtca cgcgcacagg gcgcagccct   10680
ggttaaaaac aaggtttata aatattggtt taaaagcagg ttaaaagaca ggttagcggt   10740
ggccgaaaaa cgggcggaaa cccttgcaaa tgctggattt tctgcctgtg acagcccct    10800 caaatgtcaa taggtgcgcc cctcatctgt cagcactctg cccctcaagt gtcaaggatc   10860 gcgccccctca tctgtcagta gtcgcgcccc tcaagtgtca ataccgcagg gcacttatcc   10920
ccaggcttgt ccacatcatc tgtgggaaac tcgcgtaaaa tcaggcgttt tcgccgattt   10980
gcgaggctgg ccagctccac gtcgccggcc gaaatcgagc ctgcccctca tctgtcaacg   11040
ccgcgccggg tgagtcggcc cctcaagtgt caacgtccgc ccctcatctg tcagtgaggg   11100
ccaagttttc cgcgaggtat ccacaacgcc ggcggccgcg gtgtctcgca cacggcttcg   11160
acggcgtttc tggcgcgttt gcagggccat agacggccgc cagcccagcg gcgagggcaa   11220
ccagcccggt gagcgtcgca aaggcgctcg gtcttgcctt gctcgtcggt gatgtacttc   11280
accagctccg cgaagtcgct cttcttgatg gagcgcatgg ggacgtgctt ggcaatcacg   11340 cgcaccccc ggccgtttta gcggctaaaa aagtcatggc tctgcccctcg gcggaccac    11400 gcccatcatg accttgccaa gctcgtcctg cttctcttcg atcttcgcca gcagggcgag   11460
gatcgtggca tcaccgaacc gcgccgtgcg cgggtcgtcg gtgagccaga gtttcagcag   11520
gccgcccagc ggcccaggt cgccattgat gcggggcagc tcgcggacgt gctccatagtc   11580 cacgacgccc gtgattttgt agccctggcc gacgcccagc aggtaggccg acaggctcat   11640
```

```
gccggccgcc gccgccttttt cctcaatcgc tcttcgttcg tctggaaggc agtacacctt    11700
gataggtggg ctgcccttcc tggttggctt ggtttcatca gccatccgct tgccctcatc    11760
tgttacgccg gcggtagccg gccagcctcg cagagcagga ttcccgttga gcaccgccag    11820
gtgcgaataa gggacagtga agaaggaaca cccgctcgcg ggtgggccta cttcacctat    11880
cctgcccggc tgacgccgtt ggatacacca aggaaagtct acacgaaccc tttggcaaaa    11940
tcctgtatat cgtgcgaaaa aggatggata taccgaaaaa atcgctataa tgaccccgaa    12000
gcagggttat gcagcggaaa agcgccacgc ttcccgaagg gagaaaggcg gacaggtatc    12060
cggtaagcgg cagggtcgga acaggagagc gcacgaggga gcttccaggg ggaaacgcct    12120
ggtatcttta tagtcctgtc gggtttcgcc acctctgact tgagcgtcga tttttgtgat    12180
gctcgtcagg ggggcggagc ctatggaaaa acgccagcaa cgcggccttt ttacggttcc    12240
tggccttttg ctggccttt gctcacatgt tctttcctgc gttatcccct gattctgtgg    12300
ataaccgtat taccgccttt gagtgagctg ataccgctcg ccgcagccga acgaccgagc    12360
gcagcgagtc agtgagcgag gaagcggaag agcgccagaa ggccgccaga gaggccgagc    12420
gcggccgtga ggcttggacg ctagggcagg gcatgaaaaa gcccgtagcg ggctgctacg    12480
ggcgtctgac gcggtggaaa ggggggagggg atgttgtcta catggctctg ctgtagtgag    12540
tgggttgcgc tccggcagcg gtcctgatca atcgtcaccc tttctcggtc cttcaacgtt    12600
cctgacaacg agcctccttt tcgccaatcc atcgacaatc accgcgagtc cctgctcgaa    12660
cgctgcgtcc ggaccggctt cgtcgaaggc gtctatcgcg gcccgcaaca gcggcgagag    12720
cggagcctgt tcaacggtgc cgccgcgctc gccggcatcg ctgtcgccgg cctgctcctc    12780
aagcacggcc ccaacagtga agtagctgat tgtcatcagc gcattgacgg cgtccccggc    12840
cgaaaaaccc gcctcgcaga ggaagcgaag ctgcgcgtcg gccgtttcca tctgcggtgc    12900
gcccggtcgc gtgccggcat ggatgcgcgc gccatcgcgg taggcgagca gcgcctgcct    12960
gaagctgcgg gcattcccga tcagaaatga gcgccagtcg tcgtcggctc tcggcaccga    13020
atgcgtatga ttctccgcca gcatggcttc ggccagtgcg tcgagcagcg cccgcttgtt    13080
cctgaagtgc cagtaaagcg ccggctgctg aaccccaac cgttccgcca gtttgcgtgt    13140
cgtcagaccg tctacgccga cctcgttcaa caggtccagg gcggcacgga tcactgtatt    13200
cggctgcaac tttgtcatgc ttgacacttt atcactgata acataatat gtccaccaac    13260
ttatcagtga taaagaatcc gcgcgttcaa tcggaccagc ggaggctggt ccggaggcca    13320
gacgtgaaac ccaacatacc cctgatcgta attctgagca ctgtcgcgct cgacgctgtc    13380
ggcatcggcc tgattatgcc ggtgctgccg ggcctcctgc gcgatctggt tcactcgaac    13440
gacgtcaccc cccactatgg cattctgctg gcgctgtatg cgttggtgca atttgcctgc    13500
gcacctgtgc tgggcgcgct gtcggatcgt ttcgggcggc ggccaatctt gctcgtctcg    13560
ctggccggcg ccagatctgg ggaaccctgt ggttggcatg cacatacaaa tggacgaacg    13620
gataaacctt ttcacgccct tttaaatatc cgattattct aataaacgct cttttctctt    13680
aggtttaccc gccaatatat cctgtcaaac actgatagtt taaactgaag gcgggaaacg    13740
acaatctgat catgagcgga gaattaaggg agtcacgtta tgacccccgc cgatgacgcg    13800
ggacaagccg ttttacgttt ggaactgaca gaaccgcaac gttgaaggag ccactcagcc    13860
gcgggttttct ggagtttaat gagctaagca catacgtcag aaaccattat tgcgcgttca    13920
aaagtcgcct aaggtcacta tcagctagca aatatttctt gtcaaaaatg ctccactgac    13980
```

```
gttccataaa ttcccctcgg tatccaatta gagtctcata ttcactctca atccaaataa    14040
tctgcaccgg atctggatcg tttcgcatga ttgaacaaga tggattgcac gcaggttctc    14100
cggccgcttg ggtggagagg ctattcggct atgactgggc acaacagaca atcggctgct    14160
ctgatgccgc cgtgttccgg ctgtcagcgc aggggcgccc ggttcttttt gtcaagaccg    14220
acctgtccgg tgccctgaat gaactgcagg acgaggcagc gcggctatcg tggctggcca    14280
cgacgggcgt tccttgcgca gctgtgctcg acgttgtcac tgaagcggga agggactggc    14340
tgctattggg cgaagtgccg gggcaggatc tcctgtcatc tcaccttgct cctgccgaga    14400
aagtatccat catggctgat gcaatgcggc ggctgcatac gcttgatccg gctacctgcc    14460
cattcgacca ccaagcgaaa catcgcatcg agcgagcacg tactcggatg aagccggtc    14520
ttgtcgatca ggatgatctg gacgaagagc atcaggggct cgcgccagcc gaactgttcg    14580
ccaggctcaa ggcgcgcatg cccgacggcg atgatctcgt cgtgacccat ggcgatgcct    14640
gcttgccgaa tatcatggtg gaaaatggcc gcttttctgg attcatcgac tgtggccggc    14700
tgggtgtggc ggaccgctat caggacatag cgttggctac ccgtgatatt gctgaagagc    14760
ttggcggcga atgggctgac cgcttcctcg tgctttacgg tatcgccgct cccgattcgc    14820
agcgcatcgc cttctatcgc cttcttgacg agttcttctg agcgggactc tggggttcga    14880
aatgaccgac caagcgacgc ccaacctgcc atcacgagat ttcgattcca ccgccgcctt    14940
ctatgaaagg ttgggcttcg gaatcgtttt ccggacgcc ggctgatga tcctccagcg    15000
cggggatctc atgctggagt tcttcgccca cgggatctct gcggaacagg cggtcgaagg    15060
tgccgatatc attacgacag caacggccga caagcacaac gccacgatcc tgagcgacaa    15120
tatgatcggg cccggcgtcc acatcaacgg cgtcggcggc gactgcccag gcaagaccga    15180
gatgcaccgc gatatcttgc tgcgttcgga tattttcgtg gagttcccgc cacagacccg    15240
gatgatcccc gatcgttcaa acatttggca ataaagtttc ttaagattga atcctgttgc    15300
cggtcttgcg atgattatca tataatttct gttgaattac gttaagcatg taataattaa    15360
catgtaatgc atgacgttat ttatgagatg gttttttatg attagagtcc gcaattata    15420
catttaatac gcgatagaaa acaaaatata gcgcgcaaac taggataaat tatcgcgcgc    15480
ggtgtcatct atgttactag atcgggcctc ctgtcaatgc tggcggcggc tctggtggtg    15540
gttctggtgg cggctctgag ggtggtggct ctgagggtgg cggttctgag ggtggcggct    15600
ctgagggagg cggttccggt ggtggctctg gttccggtga ttttgattat gaaaagatgg    15660
caaacgctaa taaggggct atgaccgaaa atgccgatga aaacgcgcta cagtctgacg    15720
ctaaaggcaa acttgattct gtcgctactg attacggtgc tgctatcgat ggtttcattg    15780
gtgacgtttc cggccttgct aatggtaatg gtgctactgg tgattttgct ggctctaatt    15840
cccaaatggc tcaagtcggt gacggtgata attcaccttt aatgaataat ttccgtcaat    15900
atttaccttc cctccctcaa tcggttgaat gtcgcccttt tgtctttggc ccaatacgca    15960
aaccgcctct ccccgcgcgt tggccgattc attaatgcag ctggcacgac aggtttcccg    16020
actggaaagc gggcagtgag cgcaacgcaa ttaatgtgag ttagctcact cattaggcac    16080
cccaggcttt acactttatg cttccggctc gtatgttgtg tggaattgtg agcggataac    16140
aatttcacac aggaaacagc tatgaccatg attacgcc                           16178
```

<210> SEQ ID NO 30
<211> LENGTH: 508
<212> TYPE: DNA
<213> ORGANISM: Artificial Sequence
<220> FEATURE:
<223> OTHER INFORMATION: Human cytomegalovirus immediate early enhancer and promoter sequence. This is used to drive transcription of RNAi herbicide components in eukaryotic platforms

<400> SEQUENCE: 30

```
cgttacataa cttacggtaa atggcccgcc tggctgaccg cccaacgacc cccgcccatt     60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta tgggactttc ctacttggca gtacatctac gtattagtca tcgctattac    300
catggtgatg cggttttggc agtacatcaa tgggcgtgga tagcggtttg actcacgggg    360
atttccaagt ctccacccca ttgacgtcaa tgggagtttg ttttggcacc aaaatcaacg    420
ggactttcca aaatgtcgta acaactccgc cccattgacg caaatgggcg gtaggcgtgt    480
acggtgggag gtctatataa gcagagct                                       508
```

<210> SEQ ID NO 31
<211> LENGTH: 615
<212> TYPE: RNA
<213> ORGANISM: Artificial Sequence
<220> FEATURE:
<223> OTHER INFORMATION: Synthetic TRV coat protein CDS DNA from pTRV2 sequence

<400> SEQUENCE: 31

```
augggagaua uguacgauga aucauuugac aagucgggcg guccugcuga cuugauggac     60
gauucuuggg uggaaucagu uucguggaaa gaucuguuga agaaguuaca cagcauaaaa    120
uuugcacuac agucugguag agaugagauc acuggguuac uagcggcacu gaauagacag    180
uguccuuauu caccauauga gcaguuucca gauaagaagg uguauuuccu uuuagacuca    240
cgggcuaaca gugcucuugg ugugauucag aacgcuucag cguucaagag acgagcugau    300
gagaagaaug caguggcggg uguuacaaau auuccugcga auccaaacac aacgguuacg    360
acgaaccaag ggaguacuac uacuaccaag gcgaacacug gcucgacuuu ggaagaagac    420
uuguacacuu auuacaaauu cgaugaugcc ucuacagcuu uccacaaauc ucuaacuucg    480
uuagagaaca uggaguugaa gaguuauuac cgaaggaacu uugagaaagu auucgggauu    540
aaguuuggug gagcagcugc uaguucaucu gcaccgccuc cagcgagugg agguccgaua    600
cguccuaauc ccuag                                                     615
```

<210> SEQ ID NO 32
<211> LENGTH: 615
<212> TYPE: RNA
<213> ORGANISM: Artificial Sequence
<220> FEATURE:
<223> OTHER INFORMATION: Sythetic Tobacco Rattle Virus codon-optimized coat protein mRNA sequence

<400> SEQUENCE: 32

```
augggugaca uguacgacga gucguucgau aaguccggug gcccggccga cuugauggac     60
gacagcuggg uggaauccgu cagcuggaaa gauuugcuga aaaagcucca uucuaucaag    120
uuugcguuac aauccggucg ugaugagauu accggccugc uggcggcccu gaaccgccag    180
ugcccguaca gcccguauga gcaauuccca gacaaaaaag ucuauuuccu gcuggauagc    240
cgugcuaaua gcgcccuggg cguuauucag aaugcgucug cguuuaagcg ccgcgcggac    300
```

```
gagaagaacg cgguggcggg cguuaccaau aucccggcua acccgaacac cacgguuacg    360
accaaucaag guagcacuac caccaccaag gcuaacaccg gcucgacccu ggaagaggac    420
uuguacacuu acuauaaauu ugacgacgcg ucgaccgcau uccacaaauc gcugaccucc    480
uuggaaaaua uggaacugaa gucuuauuac cgccguaacu ucgagaaagu guuugguauu    540
aaauuuggug gcgcagccgc auccagcucg gcgccgccac cggcgagcgg uggcccgauu    600
cguccgaauc cuuaa                                                    615
```

<210> SEQ ID NO 33
<211> LENGTH: 519
<212> TYPE: RNA
<213> ORGANISM: Artificial Sequence
<220> FEATURE:
<223> OTHER INFORMATION: Tomato bushy stunt virus P19 supperssor protein
      CDS DNA

<400> SEQUENCE: 33

```
auggaacgag cuauacaagg aaacgacgcu agggaacaag cuaacaguga acguugggau    60
ggaggaucag gagguaccac uucucccuuc aaacuuccug acgaaagucc gaguuggacu   120
gaguggcggc uacauaacga ugagacgaau ucgaacaag auaauccccu ugguuucaag    180
gaaagcuggg guuucgggaa aguuguauuu aagagauauc ucagauacga caggacggaa   240
gcuucacugc acagaguccu uggaucuugg acggagauu cgguuaacua ugcagcaucu    300
cgauuuuucg guuucgacca gaucggaugu accuauagua uucgguuucg aggaguuagu   360
aucaccguuu cuggagggu cgcgaacucu u cagcaucu cu gugagauggc aauucggucu    420
aagcaagaac ugcuacagcu ugccccaauc gaaguggaaa guauguauc aagaggaugc    480 ccugaaggua cugagaccuu cgaaaaagaa agcgaguaa                          519
```

<210> SEQ ID NO 34
<211> LENGTH: 1371
<212> TYPE: RNA
<213> ORGANISM: Artificial Sequence
<220> FEATURE:
<223> OTHER INFORMATION: Papaya ringspot virus strain P isolate pFT3-NP
      Hcpro peptide CDS sequence

<400> SEQUENCE: 34

```
aaugauguug cugaaaaauu cuggcucggu uucaacaggg cuuucuuacg acacagaaaa    60
ccaacggauc augugugac aucugauaua gaugguuacga uguguggugua aguagcggcu   120 uuggcaaccca uaaucuuguu uccguguau aagaucacuu gcaacacuug caugaacaaa   180 guaagggga gaguaauuga cgaaguuggu gaggacuuga uugugagcu ugaacguuua    240 cgugaaacuc ucucgucaua uggaggcuca uucggucaug uaucaacauu acucgaccaa   300
cugaacagaa uuuugaaugc acguaacaug aacgacggag cuuuuaaaga aguugcaaag   360
aagauugaug caaagaaaga aaguccuugg acccaccuaa cagccaucaa uaacacgcuu   420
auuaaagguu cguuagcaac uggcaaugaa uuugaaaaag caucugauag ccugcgggaa   480
guugugaggu ggcaucucaa aagaacagag ucaauaaaag cuggcagugu ugagagcuuu   540
agaaacaagc guucugggaa agcucacuuu aacccagcuc uuacguguga caucaauug    600 gacagaaaug gcaauuucuu auggggugaa agacaauauc acgccaaaag auucuuugcu   660
aacuacuuuu aaaagauuga ucacaguaag gguuaugagu acauauagca acgccagaac   720
ccaaauggca cucgaaaggu ugccauuggu aauuaaauau ucuccacaaa uuggagagg   780 uuucggcagc agaugguucga acaucacau ugaccaggga ccaaucacucg ugaguguauc   840
```

| | |
|---|---|
| gcacugcgca acaacaauua ugcucaugua uguagcugcg ugaccuugga ugauggaacu | 900 |
| ccagcaacga gugaauugaa aacucccacc aagaaucaca ucguucuugg uaauucuggu | 960 |
| gauccuaagu auguugacuu gccgacucuu gagucugauu caauguacau agccaagaaa | 1020 |
| gguuauugcu acaugaacau cuuuuggcg augcucauaa acauaccuga gaugaggcg | 1080 |
| aaggacuuua cgaagagagu ucgcgaucuu guugguucaa agcugggga guggccaacg | 1140 |
| augcuagaug uugcaacaug cgcuaaucaa uugauuaucu ccaucccga ugcagccaau | 1200 |
| gcagaauugc cgcgaauuuu ggugggaucac cgacagaaga caaugcacgu aauugauucg | 1260 |
| uuuggaucug uugauucugg auaucauaua cugaaggcua acacagucaa ucaguugauc | 1320 |
| caauucgcca gagagccacu cgauagugaa augaaacacu acauugucgg u | 1371 |

<210> SEQ ID NO 35
<211> LENGTH: 807
<212> TYPE: RNA
<213> ORGANISM: Artificial Sequence
<220> FEATURE:
<223> OTHER INFORMATION: Tobacco mosaic virus TMV 30kDa movement protein
    CDS sequence

<400> SEQUENCE: 35

| | |
|---|---|
| auggcucuag uuguuaaagg aaaagugaau aucaaugagu uuaucgaccu gacaaaaaug | 60 |
| gagaagaucu accgucgau guuuaccccu guaagagug uuaugguuc caaaguugau | 120 |
| aaaauaaugg uucaugagaa ugagucauug ucagagguga accuucuuaa aggaguuaag | 180 |
| cuuauugaua guggauacgu cuguuuagcc gguuuggucg ucacgggcga guggaacuug | 240 |
| ccugacaauu gcagaggagg uguguagcgug ugucgguggu acaaaaggau ggaaagagcc | 300 |
| gacgaggcca cucucggauc uuacuacaca gcagcugcaa agaaaagauu ucaguucaag | 360 |
| gucguuccca auuaugcuau aaccacccag gacgcgauga aaaacgucug caaguuuua | 420 |
| guuaauauua gaaaugugaa gaugucacgc gguuucuguc cgcuuucucu ggaguuugug | 480 |
| ucggugugua uuguuuauag aaauaauaua aaauuagguu ugagagagaa gauuacaaac | 540 |
| gugagagacg gagggcccau ggaacuuaca gaagaagucg uugaugaguu cauggaagau | 600 |
| gucccuaugu cgaucaggcu ugcaaaguuu cgaucucgaa ccggaaaaaa gagugaugcc | 660 |
| cgcaaaggga aaaauaguag uaaugaucgg ucagugccga acaagaacua agaaauguu | 720 |
| aaggauuuug gaggaaugag uuuuaaaaag aauaauuuaa ucgaugauga uucggaggcu | 780 |
| acugucgccg aaucggauuc guuuuaa | 807 |

<210> SEQ ID NO 36
<211> LENGTH: 7445
<212> TYPE: RNA
<213> ORGANISM: Arabidopsis thaliana

<400> SEQUENCE: 36

| | |
|---|---|
| augucuaccu cgucgcaauc uuuuguggcu ggacggccug cauccauggc uuccccuucg | 60 |
| caaucgcacc gcuuuugugg ucccucagcc accgcuucug guggcggaag cuuugacacu | 120 |
| uugaaucgug ucaucgcuga ccuuugcagc cgugguaauc cuaaggaggg agucccuuua | 180 |
| gcguuuagga aacacguaga ggaagcaguu cgugaucuua guggugaagc uuccucuagg | 240 |
| uucauggagc aauuauauga caggauugcu aauuuaauug agagcacuga uggcggaa | 300 |
| aacaugggug cacucagagc cauugaugag uugacggaga uggauuugg ugagaaugcu | 360 |
| acuaagguuu cuagauuugc ggguuacaug aggacugugu ucgaguugaa gcugauccu | 420 |

```
gaaaucuugg ugcuugcuag uagaguuuug gggcaccuug cucgggcagg uggagcaaug    480
acuucugaug aaguggaguu ucagaugaaa acagcuuuug auuggcuucg cguagacagg    540
guggaauauc gucguuucgc cgccguuuua auauuaaagg agauggccga aaaugcuucu    600
acugucuuua acguucaugu cccugaauuu uggaugcua ucugggugc acuuagggac      660 ccccaguugc aagugcgaga acgagcuguu gaagcuuugc gugcaugccu ucguguuauu    720
gagaaaaggg agacucgaug gcgagugcag ugguacuauc gaauguuuga agcuacacag    780
gauggguugg gcagaaaugc uccgguucac aguauucaug guucuuuacu ugccgugggg    840
gagcuguuga ggaauacagg ugaguucaug augucuaggu auagagaagu ugccgaaauu    900
guccucagau accuugaaca ucgugaucgc cuuguucgcc uuagcaucac cucguuacug    960
ccucgcauug ucacuuucu ccgugaccgg uuugugacaa acuauuuaac gauaugcaug    1020
aaucauauuc uuacugucuu aagaauaccg gcugaaagag ccaguggguu caucgcccuu    1080
ggggaaaugg cuggugcuuu ggauggagag cuuauccauu auuugccgac aauuaugucu    1140
caucugcggg augcgauugc uccacguaaa ggcagaccuu ugcuugaagc uguggcuugu    1200
guugguaaca ucgcaaaggc aaugggaucc acaguggaaa ucauguucg agaucuuuua    1260 gauguuaugu uucaucuag ucucucuucc acacuguug acgcucuuga ccagauaacc     1320
aucagcauuc cuucuuugcu gccaacagua caagaucggc uucuagauug cauuucguug    1380
guucuuucaa aaucccauua uucucaagca aagccuccug uuaccauugu ccgagguagu    1440 acaguggggca uggcaccaca gucuucugac ccuaguuguu cagcucaagu ucaacuagcc    1500
cugcagacuc uugcucguuu caauuucaag ggacaugauc uucuugaauu ugcucgggag    1560
ucaguuguug uuuauuugga ugaugaggau gcagccacaa gaaagaagc ugccuuugugu    1620 uguugcagac uaauugcaaa uucucuuucu ggcaucacac aauuggcuc gagcagguca    1680 acacgagcag gggggagacg caggcgccuu uggaagaga uugugaaaa gcuucucagg     1740 acagccguug cagaugcuga guaacuguu cgcaaaucua uauucguugc uuuauuuggc    1800
aaccaauguu ucgaugauua ucagcacag gcugauaguu ugacugccau uuuugcuucc     1860
uuaaaugaug aggaccuuga guucgagaa uaugccaucu caguugcugg aagguuaucg    1920
gaaaaaaauc cagcauacgu acuuccagca cuucgucgcc aucuauaca guuguugacc     1980 uaucuugagc ugagugcaga uaacaagugc agggaagaga gugcaaagcu ccuugguugu    2040
uuaguucgaa auugugaacg gcucauucuu ccauacuag ccccuguca aaaggcacuu     2100 guugcgagac uuagugaagg aacuggaugu aaugcuaaca auaauauugu cacuggagu     2160 cucguaacug uuggggaucu ugcaagagug gguggcuugg caaugagaca auauauuccg    2220
gagcugaugc cuuuaaugu ugaagcuuua auggauggag cugcuagc aaaacgugag       2280 guggcuguu cuacucuugg ucaaguuguu caaaguacag gguauguugu gacuccauac     2340
aaggaauacc cauuguugcu ugggsuuacuc uugaaauugc ugaaggguga cuuagugugg    2400
ucuaccagac gagaagugcu caagguucuu ggaauuaugg gcgcuuugga uccucaugug    2460
cauaaacgua accaacaaag uuuaucagga ucacaugug aaguccucg cggcacuggu      2520 gauucugguc aaccuauucc aucaauugau gaguuaccug cgaacuccg gccgucauuu    2580 gcuacaucug aggauuauua cucaacgguu gcaucaacu cgcuuaugcg aauucuuaga    2640
gaugcaucac uucuuaguua ccacaaaagg guuguuagau cucugaugau cauuuucaag    2700 ucaauggau ugggaugcgu gccuuacuug ccgaagguuu uaccgagcu uuuucacacu     2760
```

-continued

```
guucgaacau cugaugagaa ccugaaggac uucauuacgu ggggucuugg gacucuuguu    2820
uccauuguuc gccagcacau acgcaaguau cugccagagc ugcuuucauu agucucugaa    2880
cuauggucau ccuucaccuu gcccggaccc uaacgcccau cacguggucu uccgguucug    2940
caucuacugg aacaucuuug cuuggcacuu aaugaugaau ucagaacuua ucuuccaguc    3000
auccuuccau guuucaucca aguauuaggu gacgccgagc gguuuaauga uuacaccuau    3060
guuccugaua uucuccacac acucgaagug uuuggcggaa cucuugauga gcacaugcau    3120
uuacuccuuc cggcacuuau ucgauuguuu aaguagaug cuccuguagc uauaagacgc    3180
gaugccauca aaacuuugac aagaguaauc ccgugguuc agguuacugg ucauaucucc    3240
gcucucgugc aucacuugaa gcuaguauua gaugggaaga augaugaguu gcggaaagau    3300
gcugucgaug cacuaugcug uuuggcucau gcacuggag aggacuucac cauauucauu    3360
gaaucaauuc acaagcuuuu auugaagcau cgauugcggc auaagaauu ugaggaaauu    3420
caugcucgcu ggcggagacg ugaaccauug auuguagcua caacugcaac ccaacaauua    3480
aguaggcgac ugccaguuga gguuaucagg gauccuguaa uugagaauga gaucgauccu    3540
uucgaagaag gaacugacag aaaccaucag guuaauaug guagacuacg gacagcugga    3600
gaagcuucuc aacgcagcac caaagaagau ugggaggaau ggaugagaca uuuuaguauu    3660
gaauuacuua aggagucucc cucuccagca uuaagaacuu ugcaaaacu ugcucaguug    3720
cagccauuug ucgggagaga guuguuugcu gcuggcuuug ucagugcug ggcacagcua    3780
aacgagucua gccaaaagca guuaguuagg agcuuggaaa uggccuuuc aucuccaaau    3840
aucccuccag aaauuuuagc uacacuacuc aauuuggcag aguuuaugga acaugaugag    3900
aagccucuuc ccauugauau cgucuucug ggggcucuug cugaaaagug ccguguuuuu    3960
gccaaagcuc ugcauuauaa agagauggaa uuugaaggc cacgauccaa gaggauggau    4020
gccaacccag uugcuguugu cgaggcucuu auacacauaa auaacaguu acaccagcau    4080
gaggcugcug ucgguauacu aaccuaugcu caacaacauc uugaugugca auuaaaagaa    4140
ucaugguaug agaagcugca gcgcugggac gaugcacuca aggcguacac uuugaaagca    4200
ucucaaacaa caaauccuca ucuuguauua gaagccacau uaggacaaau gagaugucuu    4260
gcugcacuug cacgauggga agagcucaac aaucucugca aagaguacug gaguccugcu    4320
gagccaucug cgcucggga aauggcacca auggcugcac aagcugcaug gaacaugga    4380
gaguggggauc aaauggccga auaugugucu cggcuagaug augugauga acaaagcuu    4440
cggguuuag caagcccggu uucuagggc gauggagca guaauggcac auucuucagg    4500
gcguucugu uaguucgaag ggcaaaguac gacgaggcac gcgauauugu ggaaagagcu    4560
agaaaaugc uugccacaga acuucagcg cugguuuug agagcuauga gcugcguac    4620
agcaauaugg uucguguuca gcagcuguca gaacuagagg agguaauuga auauuuacg    4680
cugccugugg gaaauacuau ugccgaagaa cggagagcuc uaauucguaa uauggacuu    4740
cagcggauuc agggaucuaa gcguaaugug gaggugugcc aagcacuuuu ggcuguccgg    4800
gcacuugugc uaccuccuac agaagaugug gaaacuuggc ucaaguugc cucgcuuugu    4860
cgaaagagug ggaggaucag ucaggcgaaa ucuacucuac ucaagcucuu accguuugau    4920
ccagaaguau caccagaaaa caugcaauau cacggaccuc cacaagugau gcuuggauac    4980
uuaaaauacc aauggucacu uggagaggaa cguaagcgca aagaggcauu uaccaagcug    5040
cagauucuaa cgagagagcu cucaagugug ccacauucuc aaucgacau acuggcuagc    5100
augguaucua gcaagggcgc aaauguucca cuucuugcac guguaaaucu caaacuggga    5160
```

-continued

```
acguggcagu gggcacuuuc uuccgguuug aaugaugggu cuauucaaga aauucgugau    5220
gcguuugaca aaucuacuug cuaugcuccu aaaugggcua aagcauggca cacaugggca    5280
uuauucaaua cagcagugau gucgcauuac auuucaagag gucaaauugc uucccaguac    5340
guuguuucug cagucacugg auauuuuuau ucuauagcau gugcagcaaa ugccaaagga    5400
guugaugaua guuuacagga cauacugcgu cuucugacau uggguucaa ccauggagcu     5460 acagcugaug uccaaaccgc auugaagaca ggauucaguc augucaacau uaacacaugg    5520
cuuguugugc uaccucaaau cauugcuagg auacauucua auaaucgugc ugucagggaa    5580
cugauucagu cucuucucau ccgcauaggc gaaaaccacc cacaggcucu gauguauccc    5640
cuucucguug cauguaaauc aauaagcaau cuucggagag cugcggcuca agaggugguu    5700
gauaaaguuc gccagcacag uggugcacuc guggaucagg cgcaacuugu aucacaugaa    5760
cuuaucaggg uugccauacu uuggcaugaa auggcaug aagcacuaga agaagcuagu      5820
cgcuuguauu uggugaaca uaacauugaa ggcaugcuga aaguacuuga acccuuacau     5880
gacaugcucg acgaaggugu aaaaaaggac aguacgacca uacaggaaag agcauuuaua    5940
gaggcauacc gucacgaacu aaaagaggca caugaaugcu guugcaauua caagauaacu    6000
gggaaagaug cugaacuuac acaggcuugg gaucuuuacu aucacguuuu caaacggauu    6060
gacaaacagc uagccagucu cacgacauug gauuuggaau cuguuucucc ugaguugcug    6120
cugugccgug acuuggagcu agcaguuccu ggaacauauc gugcagaugc ccccgucgug    6180
acuauaucau cuuuuucacg ccaacuuguu guuauaaccu cuaaacaaag accaaggaaa    6240 uugcuauuc acggaaauga cggugaggac uacgccuucu guugaaggg acaugaagau     6300 uuaaggcaag augagcgugu uaugcagcuu uuugguuugg ugaacacuuu gcuugagaau    6360
uccagaaaaa cagccgaaaa agaucuuucc auucaacgcu auucuguaau accacuaucu    6420
cccaauagug gacucaucgg augggruccg aacgcgauua cccuucacca ucuuauucga    6480
gagcacagag augcaagaaa gaucauucuu aaucaagaaa auaagcauau guugaguuuu    6540
gcuccagacu augacaaucu accgcuuaua gcaaagguug aaguauuuga guaugcucua    6600
gaaaacacag agggaaauga ucuauccagg guucucuggu uaaaaagucg cucgucagaa    6660
guuuggcuag aaagaagaac aaacuauacu agaaguuuag caguuaugag uauguuggu    6720 uauauucuug gguuaggga ucgacaccca aguaaccuua ugcuucauag auacaguga     6780 aagaucuugc auauugauuu uggagauugu uugaggcuu cuaugaauag agagaaguuu    6840
ccugaaaagg uuccauuccg ccugacaaga augcuuguca aagcauggaa agucaguggc    6900
auugaaggaa acuuccgcuc aaccugcgaa aacguuaugc aaguucucag aaccaauaaa    6960
gauaguguaa uggcaaugau ggaagcguuu guacaugauc cuuaaucaa uuggcgucuu    7020 uucaauuuca augaagucc ccaauuagca cugcucggua caacaaccc caaugcuccu     7080 gcugauguug agccugacga agaagaugaa gauccccug auauagaucu ucccagccu     7140 caaaggagua cucgagagaa ggagauuuuc aggcuguaaa uagcuugga gaugcuaaug    7200 aaguuuaaa ugagcgugcc guaguuguua uggcacguau gagucauaag cuuuacgggc     7260
gugauuuuuc uucgucugca auccgagca auccccauugc ugaucauaau aacuugcucg    7320
gaggagauuc ucaugaaguc gaacauggu ugucugugaa aguucagguu caaaaacuaa     7380
ucaaucaagc cacuucccau gagaaucucu gucaaaacua uguuggggug ugcccuuucu    7440
gguga                                                                7445
```

<210> SEQ ID NO 37
<211> LENGTH: 1014
<212> TYPE: RNA
<213> ORGANISM: Arabidopsis thaliana

<400> SEQUENCE: 37

| | | | | | |
|---|---|---|---|---|---|
| auggcgaagg | aagcggucaa | guauguaugg | gaaggagcaa | uuccucugca | gauucaucuc | 60 |
| cacaaauccg | acgucgcuuc | ucacccugcu | ccuccuccug | cucuugaguu | agcaccaaga | 120 |
| auaggauauu | ugccucuguu | gauccucuu | auaaagccuu | auucaagga | ucacuuccu | 180 |
| ccuggugaag | auucaauuug | guugauuac | aaaggauuuc | cucuaaaaug | guauauacca | 240 |
| acaguguuc | uuuucgaucu | ccuuugugca | gaacccgaaa | gaccauggaa | ucucacgaua | 300 |
| cacuuuagag | gauauccuug | caacauacug | auaccaugug | aaggagaaga | uucuguaaaa | 360 |
| uggaacuuug | uuaauucuuu | gaagaggca | caauauauca | ucaauggaaa | uugcaagaau | 420 |
| guuaugaaca | ugucucagag | ugaucaagag | gaucuaugga | ccucugucau | gaacggugau | 480 |
| cuugaugccu | auacaagauu | auccccaag | cuuaaaaugg | gaacagucga | agaugaguuu | 540 |
| ucaaggaaaa | caaguuuguc | aucuccacaa | ucucaacaag | uugugccuga | gacggaggug | 600 |
| gcuggacaag | uuaagacagc | aagaauuccu | guucgguugu | auguucgaag | cuaaauaaa | 660 |
| gauuucgaga | aucuugaaga | guaccggag | aucgauaccu | gggaugacau | cucguaccuu | 720 |
| aaucgcccug | uugaguuccu | caagaagaa | gggaaaugcu | uuacguucg | ugacgccauu | 780 |
| aaaagucucc | ucccugaguu | auggggagac | agagcgcaaa | cgaguggugu | agaaagaagc | 840 |
| auagaugaua | cagaagaagc | agaugggucg | agggagaugg | ugaaaucaa | auugguaagg | 900 |
| auacaaggga | uagaaaugaa | gcuagagaua | ccguuucgu | gggugguaaa | uaacuugaug | 960 |
| aacccagaau | ucuaucucca | uaucucuguc | cuugugaaag | ucccucaaag | guga | 1014 |

<210> SEQ ID NO 38
<211> LENGTH: 1554
<212> TYPE: RNA
<213> ORGANISM: Arabidopsis thaliana

<400> SEQUENCE: 38

| | | | | | |
|---|---|---|---|---|---|
| augaggaaag | aggagauucc | agauaaaagu | cggacuauc | cgaucgaucc | gaaucugccg | 60 |
| aaaugggucu | gccaaaacug | ucaccacucc | cuuaccaucg | ucggcgucga | uuccuacgcc | 120 |
| ggcaaguucu | ucaacgaucc | cccuccgucc | gcuacgcagg | gcuaucuau | ccauggagcu | 180 |
| aacaguguuc | uugguucaac | acgcauggac | aacucuuuug | uuguuuuacc | ucgacauaag | 240 |
| ccuccucaau | cucagggcau | uccuccacgu | ccucgcgggg | cguccucacc | ucagccugau | 300 |
| gcuacucaau | cuggaaaggc | gauggaggaa | ucguuuguag | uugucuauaa | gucugagccu | 360 |
| guuucugauu | cuggugguuc | ucacaaucug | ucucuugaag | ugggccaaaa | cggucccuua | 420 |
| cauucaaaua | cuucuggcuu | uaaugcgacu | aucaaugucu | uaacucgugc | uuugauauu | 480 |
| gcuagaacuc | agacacaggu | ugaacagcca | uugugcuuag | aaugcaugag | gguauugucu | 540 |
| gauaaacuug | aaaagaagu | cgaggaugug | acgagggacg | uggaagcaua | cgaagcaugc | 600 |
| guucagaggu | uagaaggaga | gacgcaagau | guucuuagug | aagcugauuu | ucucaaggaa | 660 |
| aagaagaaga | uugaggaaga | agaaagaaaa | cuuguugcag | cuauagaaga | aacagagaaa | 720 |
| caaaaugcug | aaguaaacca | ucaacugaag | gagcuagaau | ucaagggaaa | ucguuuaac | 780 |
| gaacuugaag | aucgguauug | gcaagaguuc | aauaauuuc | aguucaauu | aauugccau | 840 |
| caggaagaga | gagaugcaau | cuuggcaaag | auugaaguuu | cacaagcaca | uuuagaguua | 900 |

```
uuaaauaaga caaauguacu uauugaugcc uuccccauac ggaaugaugg ggaauuuggu      960
acaauuaaca auuuucgacu uggaagacuc ccugccauaa aaguugagug ggaugagauc     1020
aaugcugcuu ggggccaagc cugucuucuc cuccauacga uguguaacua uuuccggcca     1080
aaguuucaau gucaaguuaa aauacagccg auggggaguu auccuagaau guagacagc     1140 aacaacgaaa cuuaugagcu guuuggnccu guuaacuugu uuggagcac ucgguacgau     1200 aaagccauga cacuguauuu gaugugucuu aaagacuuug cugauuuugc aaauucaaag     1260
gaccaagaga acaauauucc accagauaau ugccucaacc uuccauacaa gaucgaaaag     1320
gacaaaguau uggggauuc aauaacacag agcuucaaca agcaagagag uuggaccaaa     1380
gcacuaaagu auacucucug caaccucaaa ugggcucucu acugguucgu uggaaacacu     1440
aauuuccaac cucucucugc gacgucucu cugccuucua auauaucagc ggcugguucc     1500
uuguacgcca agcgaggucc ugacucuagu aagccuucau guaaaaaaac uuag          1554

<210> SEQ ID NO 39
<211> LENGTH: 1024
<212> TYPE: RNA
<213> ORGANISM: Artificial Sequence
<220> FEATURE:
<223> OTHER INFORMATION: Nicotiana attentuata ZIM domain protein hmRNA
      sequence used for building targeting constructs

<400> SEQUENCE: 39 auuucuugu gauuuuaaa acaugucaaa uucgcaaaau ucuuugacg gcggcagaag       60 ggccggaaaa gcgccggaga gaucgaauuu cgugcagacu uguaauuuau ugagucaguu    120
uauuaaagga aaagcuacua uuagagaucu gaaucucgga auugcuggaa aaucugaaau    180
cucagguaaa agugauguua cagaagcugc aacuauggau uuauugacaa uuauggaaaa    240
ccccucaauu gaaacuaaag aacaagaaca aaaauccaua gaucccguuc gucagagugc    300
uguaacagaa ucuucuagag auauggaggu ggccguaaau gagcccagca cgagcaaaga    360
ggcaccaaaa gagccuaagg cagcacaauu gacuauguuc uauggaugguu aagugauagu    420 auuugaugau uuuccagcug acaaagcuag agcaguaaug uuauuggcua guaaggaug     480 cccucagagu ucauuuggca cuuuucauac uacaaccauc gacaaaauua acacaucugc    540
uacugcugcu gccacagcuu cuuugacaug uaauaaaacu aaucagcuua accaaguac    600 aguuucuauu gcaccaccac aacaaaagca gcagcaaauu caguuucuu auaguaaaag    660 ugaccaacuc aagccagggu auaauucugc uacgccgcaa guacgcagc agcagcuagu    720 ccauguuucu aguacuagua aaacugauca gcuuaagcca guucaacuu cuucugcguc    780 gcaaaaacag caggagcaac aucagcaaac gcagucacag acaccuggaa cuagcagcuc    840
ugagcuaccu auugcaagaa gaucaucacu acauagguuu cuugagaaga ggaaagauag    900
ggcaacggcu agagcgccau accaaguugu acauaauaau ccguuaccau caucuucaaa    960
uaauaauggg gaaucaucuu ccaaggauug cgaagaucaa cucgaucuca auuucaaguu    1020
auag                                                                1024

<210> SEQ ID NO 40
<211> LENGTH: 750
<212> TYPE: RNA
<213> ORGANISM: Nicotiana benthamiana

<400> SEQUENCE: 40
auggagucuu gcacaucguu cuucaauucg cagucggcgu cgucucgcaa ucgcuggagu      60
```

```
uacgauucuc uuaagaacuu ccgccagauc ucucccuuug uucaaacuca ucucaaaaag    120
gucuaccuuu cauuaugcug ugcuuuaauu gcuucggcug cuggagcuua ccuucacauu    180
cuuuggaaca ucggugguuu acuuacgacg cugggaugcg ugggaagcau aguauggcug    240
auggcgacuc cucuguauga agagcaaaag aggauagcac uucugauggc agcugcacug    300
uuuaaaggag caucuguugg uccacugauu gaacuggcua ugacuuuga cccaagcauc     360 guguuaggug cuuuuguugg ugugcugug gcuuuuggu gcuucucagc ugcugccaug      420
guggcaaagc gcagagagua cuuguaucuu ggaggucuuc uuucaucugg ucucucuauc    480
cuuuucuggu ugcacuuugc guccuccauu uuuggugguu cuauggcccu auucaaguuu    540
gagguuuacu uugggcucuu ggugugugu ggcuauauca uuuugacac ccaagauaua      600 auugagaagg cacaccuugg ggauuuggac uacgugaagc augcucugac ccucuuuaca    660
gauuuuauug cuguuuugu gcgaauuuua aucauaaugu gaagaaugc auccgacaag      720 gaagagaaga agaagaagag gagaaacuaa                                     750
```

<210> SEQ ID NO 41
<211> LENGTH: 959
<212> TYPE: RNA
<213> ORGANISM: Artificial Sequence
<220> FEATURE:
<223> OTHER INFORMATION: Nicotiana sylvestris Acd2 partial transcript
      sequence dervied from N. sylvestris transcriptome

<400> SEQUENCE: 41

```
guucauccuc aaaauacaug gaacagcaga augaaaacaa gucgaaauug aaggaauuuc    60 cuuacgliguc ggucccacau agggaguuga ugguugaacu auaucgacu guggagaauc    120 ggcuuggaac agcucuucug ccuuguacuc ugccuucuaa cgugcaguac uuugagaauu    180
cgacugcuac ugcucaugcu ucucucuaug ucagaucugg ccacuccucu ucccagguug    240
auuucauacu ggguaguugg guucacugcg acugcccac agguggagcc uugaacauua     300
caagccucuc cgccuauuug agaccuucaa cugaugcacc aaacuucuua aucgaaguca    360
uccgcagcag uccaacaucu cucauccuca uucuugaucu accuccacga aaggaccucg    420
uccaacaucc ugauuaccuu aaaaccuuuu acgaggaaac acaauuagac gaacagagac    480
aacuucucga gaagcuaccu gaggugaagc cuuacuucuc uucaucucua uauauccgag    540
cuguugucuc uccgucagcu aucuugguuu ccauagaaac cgaagcuucu caggccguuc    600
gcauugauga gauuauucag gaccacauaa guccuguugc uaagguaaug uuggagacau    660
gguuggaucu gugugcuugu gcugagagaa aauugacaga ggaugaaagu acagcuuugg    720
caaagaggga uaaauaauu aagaauaaga caauugagau agaucuugaa ucaagcuucc    780
cuaggcuuuu uggucaagaa guagcaaaca agguuuuagu aguacuaagg gaaaucuaca    840
augcuugaau ucuuuacuua ugcagcuguu gauuaauaca gaaaggugau uauuguaugu    900
aaucuuguua auucuucaaa uaucagaaaa ggcaaauuga aguaauuau aaaaguugc     959
```

<210> SEQ ID NO 42
<211> LENGTH: 1717
<212> TYPE: RNA
<213> ORGANISM: Lycopersicon esculentum

<400> SEQUENCE: 42

```
cuucuuuacu ugaacauaug uguauuagua acacaaaaca uugauuaacu caauaauggu    60
uucuucucug uuacuaccaa cuccucaaau ucuuucaauu ucaucuuccu uacagucuuc    120
```

```
acuaccuuuc aaaccucaua auuuucuuca aauuacaagg aaaaaaaaua cgcuaauuuc      180
aucuccucuu agaguagcug caccuccaac aacaacaaca gcuacugaag aagaagagaa      240
gcuagauuca aaaucuagug auauugaaga uacagaaaau gaugaacaag auucgucguc      300
gaaauucucu uggagagauc auugguaccc aguucauua guggagauc ucgacccgag        360 uuuacccaca ccguuucagc uacugaaucg ugauauaguu aucgguuug auaaaucugg       420 aucucagugg guugcuuugg augacaaaug cccucaucgu cuugcuccuu uaucugaagg      480
gagauuagau gaaaaugguig auuugcagug uucauaucau ggauggucau uuaauggaug    540
ugguucuugu acaaggauac cucaagcugc aucucaagga ccugaagcua aagcuuuuca     600
gucuccaaga gcuugugcua cuagauuucc uacuaugguu ucucaaggau uacucuuugu     660
uuggccugau gaaaauggau gggagagagc ucaggcaaca aagccgccca uguugccuga     720
agauuuugau aagccugagu uugcaacugu gacaauucag cgugauuugu uuuauggcua    780
ugacacucuc auggagaacg ucucugaucc uucucacauu gauuuugcac accacaaggu    840
uacuggaagg cgagacagag caaagcccuu gccauucaag auggaggcau cuggaccuug     900 ggguuugcu ggugcgaaca augauaaacc aaaaauuacu gcaaaauuug ucgcaccuug      960
uuacucaaug aauaaaauag agaucgacac aaagcuucca aucgugggug aucagaagug    1020
ggugauaugg auuuguuccu uuaauguacc uauggcacca ggaaagacca ggucaauugu    1080
uuguagugcu cgaaacuucu cccaguuuac agugccuggc ccugcuuggu ggcagguuuu    1140
uccaagaugg caagaacacu ggacuucaaa uaagguguau gacggggaua ugauuguucu    1200
ucaaggucaa gaaaaagucu uucuuucaaa gucgaaagaa aauggaucug augucaacaa    1260
agaguauaca aaacucacau uuacaccuac ucaagcugau cguuucgucu uggcauuccg    1320
aaauuggcuu agacggcaug gcauagauca accugaaugg uuugguagca cagacaacca    1380
accacugcca ucuacugucu uauccaaacg ccagaugaug gacagauucg aacaacauac    1440
acucaaaugu ucaucuugca aaaaggcuua cuacacauuc gagaaguuac aaaaguuacu    1500
gauuggcuca guagugguau gcugugcauc ugcaggcauc ccugcagaug uuaaccuacg    1560
aauuauauug gguucauuag caauuauaag ugcuggauua gcauacauuc uacacgaauu    1620
acagaaaaau uucaucuuug uugauuaugu acaugcugaa auugacuaaa cauacaucu    1680 aagaacuuuc ucuauaaaua gcagauauuu gauuugu                             1717

<210> SEQ ID NO 43
<211> LENGTH: 1532
<212> TYPE: RNA
<213> ORGANISM: Nicotiana tabacum

<400> SEQUENCE: 43
agaaaggcaa cuaauggauc cauacaagua ccguccguca agugccuuca auucuccauu      60
cugcaccacu aauucggug ucccuguuuu aacaacaau ucaucucuua cguuggugc        120 aagaggucca guauugcuug aggauuacca uuuggugagg aaacuugcca auuuugacag     180
ggaacguguc ccugaacgug uuguucaugc ccgaggugcu agugccaaag gguuuucga      240 aguuacccau gacaucacuc accuuaccg ugcuugauuc cuucgagcuc ccgguguca       300 gacuccuguc auugugagau ucuccacugu uauacaugag aggguaguc cugaaacucu      360 gagggacccu cguggguuug cugucaaguu cuacaccaga gagggaaacu uugaucuggu    420
agggaacaac uucccccgucu ucuucauccg ugauggaaug aaguucccug acauggucca    480
```

-continued

| | |
|---|---|
| cgcgcugaag ccaaauccua aaucccauau ccaggagaau uggagggucc uugauuuuuu | 540 |
| cucucauguu ccugaaagcc ugcacauguu cacuuccuc uucgacgaua uugguauucc | 600 |
| acaagauuac aggcauaugg acgguucugg uguccacaca uucacauuga ucaacaaggc | 660 |
| ugggaaauca accuauguga aguuccacug gaagcccaca uguggguguca aguccuuguu | 720 |
| ggaagaagaa gcagcccgua ucggaggagc aaaucacagc cacgcuacuc aagaccucua | 780 |
| ugacucuauu gccgcuggaa auuauccuga auggaagcuc uucauucaga cuauggaucc | 840 |
| agaucaugaa gacagauuug auuuugaucc acuugauguu acaaaaacuu ggccagagga | 900 |
| uaucuugccg uugcagccgg ugggaagauu aguucgaac aagaacauug auaacuucuu | 960 |
| uaaugagaau gagcaacucg cuuucugccc uucuauugug guuccaggug uuuauuacuc | 1020 |
| agaugacaag augcuucaaa cucguauuuu cccuacucu gauacccaga gguaucgacu | 1080 |
| uggaccaaac uauuugcaac uuccugcuaa ugccaaag ugcucauc acaacaauca | 1140 |
| cuaugauggc ucuaugaauu uuaugcacag ggacgaggag aucgacuacu ucccuucaag | 1200 |
| guaugauccu guucgccaug cugagaagua uccaauccu ucuacaaugu gcacuggcaa | 1260 |
| acgagagaag ugugucauuc agaaagagaa caauuuaag caaccaggag auagguaccg | 1320 |
| cucauucaca ccagacaggc aagaacgcuu auucgucgg uggguggagg ccuugucuga | 1380 |
| uccucguauc acuuaugaga uccgcagcau uggaucuca uacggucuc aggcugacaa | 1440 |
| aucucugggu caaaagcuug cuucuaggcu aaugugaga ccaagcauau gaagaugaag | 1500 |
| cuuuuaaugg uuucggagga ggugauguca au | 1532 |

<210> SEQ ID NO 44
<211> LENGTH: 1257
<212> TYPE: RNA
<213> ORGANISM: Arabidopsis thaliana

<400> SEQUENCE: 44

| | |
|---|---|
| auguuguugc uggugacug cuccagcugu cguacgccgc ucaccuucc ucccggagcc | 60 |
| acccgaauc gcugcgccau uugucacgcc uucacucuca ucgcccccga gccccgucuc | 120 |
| caaucucacg cgucggcgag cccuuuuccu ucccaacu caucuccggc uccauccacu | 180 |
| uucaucuacc cgccgccaac accuucuccg uacacucacg cgccgcaugc accgucucca | 240 |
| uucaaccacg cgcccuccaga uucuuacccg uucacucacg cgccuccagc aucgucucca | 300 |
| uucaaccacg cgccgccggg uccuccaccg ccgguacaug gacagaagcg agcggugaua | 360 |
| gucggguuu cuuacaagaa cacaaaggac gaacucaaag gauguaucaa ugacgcaaac | 420 |
| ugcaugaagu ucauguugau gaagcguuuc caaucccug aaucuugcau ucuuaugcuc | 480 |
| accgaagaag aagcggaccc aaugagaugg ccaacgaaga acaacauaac aauggcgaug | 540 |
| cauuggcuug uucuuagcug caaaccggga gauucccucg ucuuucacuu ucccggucac | 600 |
| ggcaacaacc agauggacga caacggcgac gagguugacg gcuucgauga gacucuucuc | 660 |
| ccgguggacc acaggacuuc aggugucauc guggacgaug agaucaaugc acaaucgua | 720 |
| cggccgcucc cuuauggagu aagcuccau gccaucgucg acgcuuguca uaguguacc | 780 |
| gucauggacu uaccuuaucu uuguagaaug gacaggcucg gaaacuauga augggaagac | 840 |
| caucggccua aaacaggaau guggaaaggu acgaguggcg gugaagucuu cuccuucaca | 900 |
| ggcugcgaug augaccagac cucggcugac acuccgcaau ugucaggag cgcauggacg | 960 |
| ggggcaauga cuuaugcauu cauucaggcc auagaacgug gccacgggau gacuauggg | 1020 |
| agcuugcuga augcaaugag aucaacgguu caugagaucu ucgacaaaaa caaaggugaga | 1080 |

```
gagcuugugg aagugggagg ugcugauuuu cucucuacuc uucuugguuu gcucaucuua    1140
ggcgcuucuc cuccugauga ggaagaggaa guaaaccaag ccccucaaaa aacucaggaa    1200
ccacaguuga gcgcuaacga ggcauuugcu guauaugaga agcccuucuc uuuauaa       1257
```

<210> SEQ ID NO 45
<211> LENGTH: 507
<212> TYPE: RNA
<213> ORGANISM: Nicotiana benthamiana

<400> SEQUENCE: 45

```
auguugguuu accaggaucu uaucuccggu gaugagcucc ucucagauuc auuucccuac     60
aaagaacuug agaauggaug ucuuugggag guucaaggga aguggguugu ucaaggugcu    120
cuugauguag acauuggggc gaauccuucu gcgagggug cagaugaaga ugaaggugug    180
gaugaucaag cugucaaggu ugucgauauu guugacacuu ucagacuuca ggagcaacca    240
ucuuuugaca agaaacaauu uguuacauac augaagagau acaucaagaa ccugaccccc    300
aagcuagaag gagaagccca agaagcauuu aaaaagaaca uugaaucagc aacuaaguuc    360
cucaugucaa agcucaagga ccuucaguuc uuuguuggcg agagcaugca ugacgauggu    420
gcccuggugu uugcauacua caaggauggu gcaacugauc cuaccuuuuu guaccuugca    480
cauggacuca aggaggucaa guguuaa                                        507
```

<210> SEQ ID NO 46
<211> LENGTH: 633
<212> TYPE: RNA
<213> ORGANISM: Arabidopsis thaliana

<400> SEQUENCE: 46

```
augcaggacc agcuggugug ucauggugu aggaauuuau ugauguaucc uagaggagca      60
ucuaaugugc guugugcguu auguaacacu aucaacaugg uuccuccucc uccuccaccu    120
cacgacaugg cacacauuau augguggu uguagaacaa ugcuuaugua uacgcguggg    180
gcuaguagcg uaagaugcuc uugcugucaa acuacgaacc uugugccaga ucuucuuuc    240 acacuuuugu uugauaacau ucugaaagua cuuaaaacaa agcuuuuaga gguucccggu    300
ggacuagcgc acuccaauca gguugccau gcuccuucca gucagguugc gcagaucaau    360
ugugggcauu gucggacgac ccucauguau ccuuacggug caucauccgu caaaugcgcu    420
guuugucaau ucguaacuaa cguuauaug agcaauggaa ggguaccucu cccaacuaac    480
cggccaaaug gaacagcuug uccccccucu acaucaacuu caacaccacc cucucagacc    540
caaaccguug uuguagaaaa ccccaugucc guugaugaaa gcggaaaguu ggugagcaau    600
guuguuguug gagugacaac ugacaaaaag uaa                                633
```

<210> SEQ ID NO 47
<211> LENGTH: 621
<212> TYPE: RNA
<213> ORGANISM: Arabidopsis thaliana

<400> SEQUENCE: 47

```
auggcggauu cggaagcaga uaagccacug agaaaaaucu cagccgcuuu caaaaaacua     60
gcaaucaucg ugaauucacc gaauccggaa guuccuguaa cgcaauucuc ucacgcuugc    120 ucucugguucu cgcccucucuu ugguugccuu ggaauagcuu uaaguuugc ggaaauggac    180 uauguugcca agguugauga ucuugugagg gcgucgaguu cgauaucgac auuaguggua    240
```

| augauggaca aagauauuga ggcagauugu guaaggaaag cugguaguca uacgagaaac | 300 |
| cuuuugaggg uuaagcgugg ucuugacaug gucaaaguuc ucuuugaaca gaucauagcu | 360 |
| uccgaaggag auaacuccuu gaaggaucca gcaacuaagu cuuaugcuca aguguuugcu | 420 |
| ccccaccaug gaugggcuau acggaaagcu guuucucuug ggauguaugc ucuucccaca | 480 |
| agggcucacc uacuuaauau gcucaaagag gaugaggcgg cggcuaagau acauaugcaa | 540 |
| agcuauguca auucaucggc accauuaauc acguaucuug auaaucuauu ccucuccaag | 600 |
| caacucggua uugauuggug a | 621 |

<210> SEQ ID NO 48
<211> LENGTH: 530
<212> TYPE: DNA
<213> ORGANISM: Artificial Sequence
<220> FEATURE:
<223> OTHER INFORMATION: Nicotiana sylvestris PDS gene targetng construct
<400> SEQUENCE: 48

| ccccaaattg gacttgtttc tgccgttaat ttgagagtcc aagctttgga gctcgaggtc | 60 |
| ttctttggga actgaaagtc aagatggtca cttgcaaagg aagactccat ggggcataag | 120 |
| ttaaggattc gtactcccag tgccatgacc agaagattga caaaggactt taattagaca | 180 |
| atacagttaa ctatttggag gcggcgttat tatcatcatc atttcgtact tcctcacgcc | 240 |
| caagggcaat cttatgttga agctcaagac ggtttaagtg ttaaggactg gatgagaaag | 300 |
| caagctgaga gactttgcat gccgattgtt gaacatattg agtcaaaagg tggccaagtc | 360 |
| agactaaaact cacgaataaa aaagattttg acagaaaact gaagaacaca tctgataatc | 420 |
| tgctcctagc aaagcttttc cctgacgaaa tttcggcaga tcagagcaaa gcaaaaatat | 480 |
| tgaagtatca cgttgtctgt tgcttctgta cactaaattt aagatgaagg | 530 |

<210> SEQ ID NO 49
<211> LENGTH: 3020
<212> TYPE: DNA
<213> ORGANISM: Artificial Sequence
<220> FEATURE:
<223> OTHER INFORMATION: T7 driven RNA2 with NSYL PDS targeting construct in MCS
<400> SEQUENCE: 49

| taatacgact cactatagga taaaacattg cacctatggt gttgccctgg ctgggggtatg | 60 |
| tcagtgatcg cagtagaatg tactaattga caagttggag aatacggtag aacgtcctta | 120 |
| tccaacacag cctttatccc tctccctgac gaggttttg tcagtgtaat atttctttt | 180 |
| gaactatcca gctagtacc gtacgggaaa gtgactggtg tgcttatctt tgaaatgtta | 240 |
| ctttgggttt cggttcttta ggttagtaag aaagcacttg tcttctcata caaaggaaaa | 300 |
| cctgagacgt atcgcttacg aaagtagcaa tgaaagaaag gtggtggttt taatcgctac | 360 |
| cgcaaaaacg atgggggtcgt tttaattaac ttctcctacg caagcgtcta aacgacgtt | 420 |
| ggggttttgc tagtttcttt agagaaaact agctaagtct ttaatgttat cattagagat | 480 |
| ggcataaata taatacttgt gtctgctgat aagatcattt taatttggac gattagactt | 540 |
| gttgaactac aggttactga atcacttgcg ctaatcaaca tgggagatat gtacgatgaa | 600 |
| tcatttgaca agtcgggcgg tcctgctgac ttgatggacg attcttgggt ggaatcagtt | 660 |
| tcgtggaaag atctgttgaa gaagttacac agcataaaat ttgcactaca gtctggtaga | 720 |
| gatgagatca ctgggttact agcggcactg aatagacagt gtccttattc accatatgag | 780 |

| | |
|---|---|
| cagtttccag ataagaaggt gtatttcctt ttagactcac gggctaacag tgctcttggt | 840 |
| gtgattcaga acgcttcagc gttcaagaga cgagctgatg agaagaatgc agtggcgggt | 900 |
| gttacaaata ttcctgcgaa tccaaacaca acggttacga cgaaccaagg gagtactact | 960 |
| actaccaagg cgaacactgg ctcgactttg aagaagact tgtacactta ttacaaattc | 1020 |
| gatgatgcct ctacagcttt ccacaaatct ctaacttcgt tagagaacat ggagttgaag | 1080 |
| agttattacc gaaggaactt tgagaaagta ttcgggatta gtttggtgg agcagctgct | 1140 |
| agttcatctg caccgcctcc agcgagtgga ggtccgatac gtcctaatcc ctagggattt | 1200 |
| aaggacgtga actctgttga gatctctgtg aaattcagag ggtgggtgat accatattca | 1260 |
| ctgatgccat tagcgacatc taaatagggc taattgtgac taatttgagg gaatttcctt | 1320 |
| taccattgac gtcagtgtcg ttggtagcat ttgagtttcg caatgcacga attacttagg | 1380 |
| aagtggcttg acgacactaa tgtgttattg ttagataatg gtttggtggt caaggtacgt | 1440 |
| agtagagtcc cacatattcg cacgtatgaa gtaattggaa agttgtcagt ttttgataat | 1500 |
| tcactgggag atgatacgct gtttgaggga aaagtagaga acgtatttgt ttttatgttc | 1560 |
| aggcggttct tgtgtgtcaa caaagatgga cattgttact caaggaagca cgatgagctt | 1620 |
| tattattacg gacgagtgga cttagattct gtgagtaagg ttaccgaatt ctccccaaat | 1680 |
| tggacttgtt tctgccgtta atttgagagt ccaagctttg gagctcgagg tcttctttgg | 1740 |
| gaactgaaag tcaagatggt cacttgcaaa ggaagactcc atggggcata agttaaggat | 1800 |
| tcgtactccc agtgccatga ccagaagatt gacaaaggac tttaattaga caatacagtt | 1860 |
| aactatttgg aggcggcgtt attatcatca tcatttcgta cttcctcacg cccaagggca | 1920 |
| atcttatgtt gaagctcaag acggtttaag tgttaaggac tggatgagaa agcaagctga | 1980 |
| gagactttgc atgccgattg ttgaacatat tgagtcaaaa ggtggccaag tcagactaaa | 2040 |
| ctcacgaata aaaagatttt tgacagaaaa ctgaagaaca catctgataa tctgctccta | 2100 |
| gcaaagcttt tccctgacga aatttcggca gatcagagca aagcaaaaat attgaagtat | 2160 |
| cacgttgtct gttgcttctg tacactaaat ttaagatgaa ggctagaagg cctccatggg | 2220 |
| gatccggtac cgagctcacg cgtctcgagg cccgggcatg tcccgaagac attaaactac | 2280 |
| ggttctttaa gtagatccgt gtctgaagtt ttaggttcaa tttaaaccta cgagattgac | 2340 |
| attctcgact gatcttgatt gatcggtaag tcttttgtaa tttaatttc ttttgattt | 2400 |
| tattttaaat tgttatctgt ttctgtgtat agactgtttg agatcggcgt ttggccgact | 2460 |
| cattgtctta cctagggga acggactttg tttgtgttgt tattttattt gtatttatt | 2520 |
| aaaattctca acgatctgaa aaagcctcgc ggctaagaga ttgttggggg gtgagtaagt | 2580 |
| acttttaaag tgatgatggt tacaaaggca aaaggggtaa aaccccctcgc ctacgtaagc | 2640 |
| gttattacgc ccgtctgtac ttatatcagt acactgacga gtccctaaag gacgaaacgg | 2700 |
| gagaacgcta gccaccacca ccaccaccac gtgtgaatta caggtgacca gctcgaattt | 2760 |
| ccccgatcgt tcaaacattt ggcaataaag tttcttaaga ttgaatcctg ttgccggtct | 2820 |
| tgcgatgatt atcatataat ttctgttgaa ttacgttaag catgtaataa ttaacatgta | 2880 |
| atgcatgacg ttatttatga gatgggtttt tatgattaga gtcccgcaat tatacattta | 2940 |
| atacgcgata gaaaacaaaa tatagcgcgc aaactaggat aaattatcgc gcgcggtgtc | 3000 |
| atctatgtta ctagatcggg | 3020 |

<210> SEQ ID NO 50

<211> LENGTH: 6585
<212> TYPE: DNA
<213> ORGANISM: Artificial Sequence
<220> FEATURE:
<223> OTHER INFORMATION: T7 driven truncated PPK20 RNAI consisting of 5'
    sequence replicase CDS, PUC57 MCS, 3' sequence, ribozyme and NOS
    terminator
<220> FEATURE:
<221> NAME/KEY: misc_feature
<222> LOCATION: (6125)..(6125)
<223> OTHER INFORMATION: n is a, c, g or t

<400> SEQUENCE: 50

| | | | | | |
|---|---|---|---|---|---|
| taatacgact | cactatagga | tggcgaacgg | taacttcaag | ttgtctcaat | tgctcaatgt | 60 |
| ggacgagatg | tctgctgagc | agaggagtca | tttctttgac | ttgatgctga | ctaaacctga | 120 |
| ttgtgagatc | gggcaaatga | tgcaaagagt | tgttgttgat | aaagtcgatg | acatgattag | 180 |
| agaaagaaag | actaaagatc | cagtgattgt | tcatgaagtt | ctttctcaga | aggaacagaa | 240 |
| caagttgatg | gaaatttatc | ctgaattcaa | tatcgtgttt | aaagacgaca | aaaacatggt | 300 |
| tcatgggttt | gcggctgctg | agcgaaaact | acaagcttta | ttgcttttag | atagagttcc | 360 |
| tgctctgcaa | gaggtggatg | acatcggtgg | tcaatggtcg | ttttgggtaa | ctagaggtga | 420 |
| gaaaaggatt | cattcctgtt | gtccaaatct | agatattcgg | gatgatcaga | gagaaatttc | 480 |
| tcgacagata | tttcttactg | ctattggtga | tcaagctaga | agtggtaaga | cagagatgtc | 540 |
| ggagaatgag | ctgtggatgt | atgaccaatt | tcgtgaaaat | attgctgcgc | ctaacgcggt | 600 |
| taggtgcaat | aatacatatc | agggttgtac | atgtaggggt | ttttctgatg | gtaagaagaa | 660 |
| aggcgcgcag | tatgcgatag | ctcttcacag | cctgtatgac | ttcaagttga | aagacttgat | 720 |
| ggctactatg | gttgagaaga | aaactaaagt | ggttcatgct | gctatgcttt | tgctcctga | 780 |
| aagtatgtta | gtgacgaag | gtccattacc | ttctgttgac | ggttactaca | tgaagaagaa | 840 |
| cgggaagatc | tatttcggtt | ttgagaaaga | tccttccttt | tcttacattc | atgactggga | 900 |
| agagtacaag | aagtatctac | tggggaagcc | agtgagttac | caagggaatg | tgttctactt | 960 |
| cgaaccgtgg | caggtgagag | gagacacaat | gcttttttcg | atctacagga | tagctggagt | 1020 |
| tccgaggagg | tctctatcat | cgcaagagta | ctaccgaaga | atatatatca | gtagatggga | 1080 |
| aaacatggtt | gttgtcccaa | ttttcgatct | ggtcgaatca | acgcgagagt | tggtcaagaa | 1140 |
| agacctgttt | gtagagaaac | aattcatgga | caagtgtttg | gattacatag | ctaggttatc | 1200 |
| tgaccagcag | ctgaccataa | gcaatgttaa | atcatacttg | agttcaaata | attgggtctt | 1260 |
| attcataaac | ggggcggccg | tgaagaacaa | gcaaagtgta | gattctcgag | atttacagtt | 1320 |
| gttggctcaa | actttgctag | tgaaggaaca | agtggcgaga | cctgtcatga | gggagttgcg | 1380 |
| tgaagcaatt | ctgactgaga | cgaaaccat | cacgtcattg | actgatgtgc | tgggtttaat | 1440 |
| atcaagaaaa | ctgtggaagc | agtttgctaa | caagatcgca | gtcggcggat | tcgttggcat | 1500 |
| ggttggtact | ctaattggat | tctatccaaa | gaaggtacta | acctgggcga | aggacacacc | 1560 |
| aaatggtcca | gaactatgtt | acgagaactc | gcacaaaacc | aaggtgatag | tatttctgag | 1620 |
| tgttgtgtat | gccattggag | gaatcacgct | tatgcgtcga | gacatccgag | atggactggt | 1680 |
| gaaaaaacta | tgtgatatgt | ttgatatcaa | acggggggcc | catgtcttag | acgttgagaa | 1740 |
| tccgtgccgc | tattatgaaa | tcaacgattt | ctttagcagt | ctgtattcgg | catctgagtc | 1800 |
| cggtgagacc | gttttaccag | atttatccga | ggtaaaagcc | aagtctgata | agctattgca | 1860 |
| gcagaagaaa | gaaatcgctg | acgagtttct | aagtgcaaaa | ttctctaact | attctggcag | 1920 |
| ttcggtgaga | acttctccac | catcggtggt | cggttcatct | cgaagcggac | tgggtctgtt | 1980 |

```
gttggaagac agtaacgtgc tgacccaagc tagagttgga gtttcaagaa aggtagacga    2040
tgaggagatc atggagcagt ttctgagtgg tcttattgac actgaagcag aaattgacga    2100
ggttgttcca gccttttcag ctgaatgtga agagggaa  acaagcggta caaaggtgtt    2160
gtgtaaacct ttaacgccac caggatttga gaacgtgttg ccagctgtca aacctttggt    2220
cagcaaagga aaaacggtca aacgtgtcga ttacttccaa gtgatgggag gtgagagatt    2280
accaaaaagg ccggttgtca gtggagacga ttctgtggac gctagaagag agtttctgta    2340
ctacttagat gcggagagag tcgctcaaaa tgatgaaatt atgtctctgt atcgtgacta    2400
ttcgagagga gttattcgaa ctggaggtca gaattacccg cacgactgg  gagtgtggga    2460 tgtggagatg aagaactggt gcatacgtcc agtggtcact gaacatgctt atgtgttcca    2520
accagacaaa cgtatggatg attggtcggg atacttagaa gtggctgttt gggaacgagg    2580
tatgttggtc aacgacttcg cggtcgaaag gatgagtgat tatgtcatag tttgcgatca    2640
gacgtatctt tgcaataaca ggttgatctt ggacaattta agtgccctgg atctaggacc    2700
agttaactgt tcttttgaat tagttgacgg tgtacctggt tgtggtaagt cgacaatgat    2760
tgtcaactca gctaatcctt gtgtcgatgt ggttctctct actgggagag cagcaaccga    2820
cgacttgatc gagagattcg cgagcaaagg ttttccatgc aaattgaaaa ggagagtgaa    2880
gacggttgat tcttttttga tgcattgtgt tgatggttct ttaaccggag acgtgttgca    2940
tttcgatgaa gctctcatgg cccatgctgg tatggtgtac ttttgcgctc agatagctgg    3000
tgctaaacga tgtatctgtc aaggagatca gaatcaaatt tctttcaagc ctagggtatc    3060
tcaagttgat ttgaggtttt ctagtctggt cggaaagttt gacattgtta cagaaaaaag    3120
agaaacttac agaagtccag cagatgtggc tgccgtattg aacaagtact atactggaga    3180
tgtcagaaca cataacgcga ctgctaattc gatgacggtg aggaagattg tgtctaaaga    3240
acaggtttct ttgaagcctg gtgctcagta cataactttc cttcagtctg agaagaagga    3300
gttggtaaat ttgttggcat tgaggaaagt ggcagctaaa gtgagtacag tacacgagtc    3360
gcaaggagag acattcaaag atgtagtcct agtcaggacg aaacctacgg atgactcaat    3420
cgctagaggt cgggagtact taatcgtggc gttgtcgcgt cacacacaat cacttgtgta    3480
tgaaactgtg aaagaggacg atgtaagcaa agagatcagg gaaagtgccg cgcttacgaa    3540
ggcggctttg gcaagatttt ttgttactga gaccgtctta tgacggtttc ggtctaggtt    3600
tgatgtcttt agacatcatg aagggccttg cgccgttcca gattcaggta cgattacgga    3660
cttggagatg tggtacgacg ctttgtttcc gggaaattcg ttaagagact caagcctaga    3720
cgggtatttg gtggcaacga ctgattgcaa tttgcgatta gacaatgtta cgatcaaaag    3780
tggaaactgg aaagacaagt ttgctgaaaa agaaacgttt ctgaaccgg  ttattcgtac    3840 tgctatgcct gacaaaagga agactactca gttggagagt ttgttagcat gcagaaaag   3900 gaaccaagcg gcacccgatc tacaagaaaa tgtgcacgca acagttctaa tcgaagagac    3960
gatgaagaag ttgaaatctg ttgtctacga tgtgggaaaa attcgggctg atcctattgt    4020
caatagagct caaatggaga gatggtggag aaatcaaagc acagcggtac aggctaaggt    4080
agtagcagat gtgagagagt tacatgaaat agactattcg tcttacatgt atatgatcaa    4140
atctgacgtg aaacctaaga ctgatttaac accgcaattt gaatactcag ctctacagac    4200
tgttgtgtat cacgagaagt tgatcaactc gttgttcggt ccaattttca aagaaattaa    4260
tgaacgcaag ttggatgcta tgcaaccaca ttttgtgttc aacacgagaa tgacatcgag    4320
```

```
tgatttaaac gatcgagtga agttcttaaa tacggaagcg gcttacgact ttgttgagat    4380
agacatgtct aaattcgaca agtcggcaaa tcgcttccat ttacaactgc agctggagat    4440
ttacaggtta tttgggctag atgagtgggc ggccttcctt tgggaggtgt cgcacactca    4500
aactactgtg agagatattc aaaatggtat gatggcgcat atttggtacc aacaaaagag    4560
tggagatgct gatacttata atgcaaattc agatagaaca ctgtgtgcac tcttgtctga    4620
attaccattg gagaaagcag tcatggttac atatggagga gatgactcac tgattgcgtt    4680
tcctagagga acgcagtttg ttgatccgtg tccaaagttg gctactaagt ggaatttcga    4740
gtgcaagatt tttaagtacg atgtcccaat gttttgtggg aagttcttgc ttaagacgtc    4800
atcgtgttac gagttcgtgc cagatccggt aaaagttctg acgaagttgg ggaaaaagag    4860
tataaaggat gtgcaacatt tagccgagat ctacatctcg ctgaatgatt ccaatagagc    4920
tcttgggaac tacatggtgg tatccaaact gtccgagtct gtttcagacc ggtatttgta    4980
caaaggtgat tctgttcatg cgctttgtgc gctatggaag catattaaga gttttacagc    5040
tctgtgtaca ttattccgag acgaaaacga taaggaattg aacccggcta aggttgattg    5100
gaagaaggca cagagagctg tgtcaaactt ttacgactgg taatatggaa gaaagtcatt    5160
ggtcaccttg aagaagaaga cttccgaagt ctcaaaattc tcaaatctag ggccattga    5220
attgtttgtg gacggtagga ggaagagacc gaagtatttt cacagaagaa gagaaactgt    5280
cctaaatcat gttggtggga agaagagtga acacaagtta gacgttttg accaaaggga     5340
ttacaaaatg attaaatctt acgcgtttct aaagatagta ggtgtacaac tagttgtaac    5400
atcacatcta cctgcagata cgcctgggtt cattcaaatc gatctgttgg attcgagact    5460
tactgagaaa agaaagagag gaaagactat tcagagattc aaagctcgag cttgcgataa    5520
ctgttcagtt gcgcagtaca aggttgaata cagtatttcc acacaggaga acgtacttga    5580
tgtctggaag gtgggttgta tttctgaggg cgttccggtc tgtgacggta catacccttt    5640
cagtatcgaa gtgtcgctaa tatgggttgc tactgattcg actaggcgcc tcaatgtgga    5700
agaactgaac agttcggatt acattgaagg cgattttacc gatcaagagg ttttcggtga    5760
gttcatgtct ttgaaacaag tggagatgaa gacgattgag gcgaagtacg atggtcctta    5820
cagaccagct actactagac ctaagtcatt attgtcaagt gaagatgtta agagagcgtc    5880
taataagaaa aactcgtctt aatgcataaa gaaatttatt gtcaatgaat tcgagctcgg    5940
tacctcgcga atgcatctag atatcggatc ccgggcccgt cgactgcaga ggcctgcatg    6000
caagcttttt tattttatat tgttatctgt ttctgtgtat agactgtttg agattggcgc    6060
ttggccgact cattgtctta ccataggga acggactttg tttgtgttgt tattttattt    6120
gtatntatta aaattctcaa tgatctgaaa aggcctcgag gctaagagat tattggggg     6180
tgagtaagta cttttaaagt gatgatggtt acaaaggcaa aaggggtaaa acccctcgcc    6240
tacgtaagcg ttattacgcc cgtctgtact tatatcagta cactgacgag tccctaaagg    6300
acgaaacggg cccctcgaat ttccccgatg ggcgttcaaa catttggcaa taaagtttct    6360
taagattgaa tcctgttgcc ggtcttgcga tgattatcat ataatttctg ttgaattacg    6420
ttaagcatgt aataattaac atgtaatgca tgacgttatt tatgagatgg gttttttatga   6480
ttagagtccc gcaattatac atttaatacg cgatagaaaa caaaatatag cgcgcaaact    6540
aggataaatt atcgcgcgcg gtgtcatcta tgttactaga tcggg                    6585
```

<210> SEQ ID NO 51
<211> LENGTH: 5124

<212> TYPE: DNA
<213> ORGANISM: Artificial Sequence
<220> FEATURE:
<223> OTHER INFORMATION: TRV PPK20 RNAI replicase CDS

<400> SEQUENCE: 51

```
atggcgaacg gtaacttcaa gttgtctcaa ttgctcaatg tggacgagat gtctgctgag      60
cagaggagtc atttctttga cttgatgctg actaaacctg attgtgagat cgggcaaatg     120
atgcaaagag ttgttgttga taaagtcgat gacatgatta gagaaagaaa gactaaagat     180
ccagtgattg ttcatgaagt tctttctcag aaggaacaga acaagttgat ggaaatttat     240
cctgaattca atatcgtgtt taaagacgac aaaaacatgg ttcatgggtt tgcggctgct     300
gagcgaaaac tacaagcttt attgctttta gatagagttc ctgctctgca gaggtggat      360
gacatcggtg gtcaatggtc gttttgggta actagaggtg agaaaaggat tcattcctgt     420
tgtccaaatc tagatattcg ggatgatcag agagaaattt ctcgacagat atttcttact     480
gctattggtg atcaagctag aagtggtaag agacagatgt cggagaatga gctgtggatg     540
tatgaccaat tcgtgaaaaa tattgctgcg cctaacgcgg ttaggtgcaa taatacatat     600
cagggttgta catgtagggg ttttttctgat ggtaagaaga aaggcgcgca gtatgcgata     660
gctcttcaca gcctgtatga cttcaagttg aaagacttga tggctactat ggttgagaag     720
aaaactaaag tggttcatgc tgctatgctt tttgctcctg aaagtatgtt agtggacgaa     780
ggtccattac cttctgttga cggttactac atgaagaaga acgggaagat ctatttcggt     840
tttgagaaag atccttcctt tcttacatt catgactggg aagagtacaa gaagtatcta     900
ctggggaagc cagtgagtta ccaagggaat gtgttctact cgaaccgtg gcaggtgaga      960
ggagacacaa tgcttttttc gatctacagg atagctggag ttccgaggag gtctctatca    1020
tcgcaagagt actaccgaag aatatatatc agtagatggg aaaacatggt tgttgtccca    1080
attttcgatc tggtcgaatc aacgcgagag ttggtcaaga aagacctgtt tgtagagaaa    1140
caattcatgg acaagtgttt ggattacata gctaggttat ctgaccagca gctgaccata    1200
agcaatgtta atcatactt gagttcaaat aattgggtct tattcataaa cggggcggcc     1260
gtgaagaaca agcaaagtgt agattctcga gatttacagt tgttggctca aactttgcta    1320
gtgaaggaac aagtggcgag acctgtcatg agggagttgc gtgaagcaat tctgactgag    1380
acgaaaccta tcacgtcatt gactgatgtg ctgggtttaa tatcaagaaa actgtggaag    1440
cagtttgcta acaagatcgc agtcggcgga ttcgttggca tggttggtac tctaattgga    1500
ttctatccaa agaaggtact aacctgggcg aaggacacac caaatggtcc agaactatgt    1560
tacgagaact cgcacaaaac caaggtgata gtatttctga gtgttgtgta tgccattgga    1620
ggaatcacgc ttatgcgtcg agacatccga gatggactgg tgaaaaaact atgtgatatg    1680
tttgatatca aacgggggc ccatgtctta gacgttgaga atccgtgccg ctattatgaa     1740
atcaacgatt tctttagcag tctgtattcg gcatctgagt ccggtgagac cgttttacca    1800
gatttatccg aggtaaaagc caagtctgat aagctattgc agcagaagaa agaaatcgct    1860
gacgagtttc taagtgcaaa attctctaac tattctggca gttcggtgag aacttctcca    1920
ccatcggtgg tcggttcatc tcgaagcgga ctgggtctgt tgttggaaga cagtaacgtg    1980
ctgacccaag ctagagttgg agtttcaaga aaggtagacg atgaggagat catggagcag    2040
tttctgagtg gtcttattga cactgaagca gaaattgacg aggttgttcc agcctttca     2100
gctgaatgtg aaagagggga acaagcggt acaaaggtgt tgtgtaaacc tttaacgcca    2160
```

```
ccaggatttg agaacgtgtt gccagctgtc aaacctttgg tcagcaaagg aaaaacggtc    2220
aaacgtgtcg attacttcca agtgatggga ggtgagagat taccaaaaag gccggttgtc    2280
agtggagacg attctgtgga cgctagaaga gagtttctgt actacttaga tgcggagaga    2340
gtcgctcaaa atgatgaaat tatgtctctg tatcgtgact attcgagagg agttattcga    2400
actggaggtc agaattaccc gcacggactg ggagtgtggg atgtggagat gaagaactgg    2460
tgcatacgtc cagtggtcac tgaacatgct tatgtgttcc aaccagacaa acgtatggat    2520
gattggtcgg gatacttaga agtggctgtt tgggaacgag gtatgttggt caacgacttc    2580
gcggtcgaaa ggatgagtga ttatgtcata gtttgcgatc agacgtatct ttgcaataac    2640
aggttgatct tggacaattt aagtgccctg gatctaggac cagttaactg ttcttttgaa    2700
ttagttgacg tgtacctgg ttgtggtaag tcgacaatga ttgtcaactc agctaatcct    2760
tgtgtcgatg tggttctctc tactgggaga gcagcaaccg acgacttgat cgagagattc    2820
gcgagcaaag gttttccatg caaattgaaa aggagagtga agacggttga ttcttttttg    2880
atgcattgtg ttgatggttc tttaaccgga gacgtgttgc atttcgatga agctctcatg    2940
gcccatgctg gtatggtgta cttttgcgct cagatagctg gtgctaaacg atgtatctgt    3000
caaggagatc agaatcaaat ttcttttcaag cctagggtat ctcaagttga tttgaggttt    3060
tctagtctgg tcggaaagtt tgacattgtt acagaaaaaa gagaaactta cagaagtcca    3120
gcagatgtgg ctgccgtatt gaacaagtac tatactggag atgtcagaac acataacgcg    3180
actgctaatt cgatgacggt gaggaagatt gtgtctaaag aacaggtttc tttgaagcct    3240
ggtgctcagt acataacttt ccttcagtct gagaagaagg agttggtaaa tttgttggca    3300
ttgaggaaag tggcagctaa agtgagtaca gtacacgagt cgcaaggaga gacattcaaa    3360
gatgtagtcc tagtcaggac gaaacctacg gatgactcaa tcgctagagg tcgggagtac    3420
ttaatcgtgg cgttgtcgcg tcacacacaa tcacttgtgt atgaaactgt gaaagaggac    3480
gatgtaagca aagagatcag ggaaagtgcc gcgcttacga aggcggcttt ggcaagattt    3540
tttgttactg agaccgtctt atgacggttt cggtctaggt ttgatgtctt tagacatcat    3600
gaagggcctt gcgccgttcc agattcaggt acgattacgg acttggagat gtggtacgac    3660
gctttgtttc cggaaaattc gttaagagac tcaagcctag acgggtattt ggtggcaacg    3720
actgattgca atttgcgatt agacaatgtt acgatcaaaa gtggaaactg aaagacaag     3780 tttgctgaaa aagaaacgtt tctgaaaccg gttattcgta ctgctatgcc tgacaaaagg    3840
aagactactc agttggagag tttgttagca ttgcagaaaa ggaaccaagc ggcacccgat    3900
ctacaagaaa atgtgcacgc aacagttcta atcgaagaga cgatgaagaa gttgaaatct    3960
gttgtctacg atgtgggaaa aattcgggct gatcctattg tcaatagagc tcaaatggag    4020
agatggtgga gaaatcaaag cacagcggta caggctaagg tagtagcaga tgtgagagag    4080
ttacatgaaa tagactattc gtcttacatg tatatgatca aatctgacgt gaaacctaag    4140
actgatttaa caccgcaatt tgaatactca gctctacaga ctgttgtgta tcacgagaag    4200
ttgatcaact cgttgttcgg tccaattttc aaagaaatta atgaacgcaa gttggatgct    4260
atgcaaccac atttttgtgtt caacacgaga atgacatcga gtgatttaaa cgatcgagtg    4320
aagttcttaa atacggaagc ggcttacgac tttgttgaga tagacatgtc taaattcgac    4380
aagtcggcaa atcgcttcca tttacaactg cagctggaga tttacaggtt atttgggcta    4440
gatgagtggg cggccttcct ttgggaggtg tcgcacactc aaaactactgt gagagatatt    4500 caaaatggta tgatggcgca tatttggtac caacaaaaga gtggagatgc tgatacttat    4560
```

-continued

```
aatgcaaatt cagatagaac actgtgtgca ctcttgtctg aattaccatt ggagaaagca    4620
gtcatggtta catatggagg agatgactca ctgattgcgt ttcctagagg aacgcagttt    4680
gttgatccgt gtccaaagtt ggctactaag tggaatttcg agtgcaagat ttttaagtac    4740
gatgtcccaa tgttttgtgg gaagttcttg cttaagacgt catcgtgtta cgagttcgtg    4800
ccagatccgg taaaagttct gacgaagttg gggaaaaaga gtataaagga tgtgcaacat    4860
ttagccgaga tctacatctc gctgaatgat tccaatagag ctcttgggaa ctacatggtg    4920
gtatccaaac tgtccgagtc tgtttcagac cggtatttgt acaaaggtga ttctgttcat    4980
gcgctttgtg cgctatggaa gcatattaag agttttacag ctctgtgtac attattccga    5040
gacgaaaacg ataaggaatt gaacccggct aaggttgatt ggaagaaggc acagagagct    5100
gtgtcaaact tttacgactg gtaa                                          5124
```

<210> SEQ ID NO 52
<211> LENGTH: 320
<212> TYPE: DNA
<213> ORGANISM: Artificial Sequence
<220> FEATURE:
<223> OTHER INFORMATION: TRV Ppk20 RNA2 5' replication element
      containing sequence

<400> SEQUENCE: 52

```
ataaaacatt gcacctatgg tgttgccctg gctggggtat gtcagtgatc gcagtagaat     60
gtactaattg acaagttgga gaatacggta gaacgtcctt atccaacaca gcctttatcc    120
ctctccctga cgaggttttt gtcagtgtaa tatttctttt tgaactatcc agcttagtac    180
cgtacgggaa agtgactggt gtgcttatct ttgaaatgtt actttgggtt tcggttctt     240 aggttagtaa gaaagcactt gtcttctcat acaaaggaaa acctgagacg tatcgcttac    300
gaaagtagca atgaaagaaa                                                320
```

<210> SEQ ID NO 53
<211> LENGTH: 394
<212> TYPE: DNA
<213> ORGANISM: Artificial Sequence
<220> FEATURE:
<223> OTHER INFORMATION: TRV Ppk20 RNA2 3' replication element
      containing sequence
<220> FEATURE:
<221> NAME/KEY: misc_feature
<222> LOCATION: (258)..(258)
<223> OTHER INFORMATION: n is a, c, g or t

<400> SEQUENCE: 53

```
atgtcccgaa gacattaaac tacggttctt taagtagatc cgtgtctgaa gttttaggtt     60
caatttaaac ctacgagatt gacattctcg actgatcttg attgatcggt aagtcttttg    120
taatttaatt ttcttttga ttttatttta aattgttatc tgtttctgtg tatagactgt     180
ttgagatcgg cgtttggccg actcattgtc ttaccatagg gaacggact  ttgtttgtgt    240 tgttatttta tttgtatnta ttaaaattct caacgatctg aaaaagcctc gcggctaaga    300
gattgttggg gggtgagtaa gtacttttaa agtgatgatg gttacaaagg caaaggggt     360 aaacccctc gcctacgtaa gcgttattac gccc                                 394
```

<210> SEQ ID NO 54
<211> LENGTH: 1026
<212> TYPE: RNA
<213> ORGANISM: Arabidopsis thaliana

<400> SEQUENCE: 54

```
auggcuccga cuuugcaagg ccagugggauc aaggugggc agaaaggagg aacgggacca        60
ggaccuagaa guucacacgg cauagccgcg gucggagaca agcucuacag uuucggcggc       120
gaguuaacac caaacaaaca caucgacaaa gaccucuacg ucuuugacuu caacacucaa       180
acuuggucaa ucgcucaacc caaggagac gccccaacug uaccugcuu aggcgugcgc        240
augguggccg ugggaacuaa gaucuauauc uuuggaggcc gcgaugagaa ccgcaacuuc       300
gaaaacuuuc gcuccuacga uacggugaca uccgagugga cauuccugac gaagcuugau       360
gagguggag gacccgaggc ucguacuuuc cauucgaugg cuucggauga aaaccaugug        420
uaguauucg guggggugag caaaggcggu acuaugaaua ucccacgcg guucaggaca         480
aucgaggcgu auaacauugc ugaugggaaa ugggcucagc uaccggauc aggagauaac        540
uucgagaaaa gaggaggagc gggauucgcu ugguacaag ggaagauuug gugguuau        600
gguuugcga ccucgauugu gcccggagc aaagaugacu augagcuaa ugcugugcaa         660
uucuaugauc cggcuuccaa aaaguggacc gaaguagaga cuacaggagc gaaaccuucc       720
gcaaggagcg uguuugccca ugcggugagug ggaaaguaua uaauaauauu ugcaggugag      780
guauggccug aucucaaugg gcauuaugguc cccgggacgc uguccaauga gggauaugcg      840
uuggacaccg agacacuggu ugggaaaag uggggagaag aaggugcacc agccauacca       900
cgagguugga cugccauac ugcugccacu gucgauggaa agaauggccu ccucaugcau      960
ggcggaaagc uuccgaccaa cgagcgaacu gaugaucucu acuucaugc ggucaauuca     1020
gcuuaa                                                                1026
```

<210> SEQ ID NO 55
<211> LENGTH: 1041
<212> TYPE: RNA
<213> ORGANISM: Arabidopsis thaliana

<400> SEQUENCE: 55

```
auggcuuuaa aacauaugca aaucuuucuc uucgucgcua uauuucauc auucuguuuc        60
uccaucacuc uuucucgucc acucgacaau gaacucauca ugcaaaagag gcacaucgag       120
uggaugacua aacacggccg ugucuacgcg gaugugaagg aggaaaacaa ucgcuacguu       180
guguucaaaa acaacgucga acgcauugaa cauuuaaaua gcauuccugc cggaagaacu       240
uucaaacuug cgguaaauca guuugcugau uuaaccaaug acgaauuucg uuccauguac       300
acuguuuca aaggugucuc ggcauuaucu agccaaagcc aaacuaaaau gucgccguuu       360
agguaccaaa acguuucuuc uggugcuuug ccgguuucug uugacuggag gaagaaagga       420
gcugugaccc cuaucaagaa ucaaggcagc ugcggaguguu uugggcguuu ucagcgguu      480
gcggcuauug aaggagcaac acaaauaaag aaagggaaac uuauaucuuu gucagaacaa       540
cagcuuguug auuugcgacac aaacgauuuu ggcugcgaag gcgguuaau ggauacugcg       600
uuugagcaua uaaaagcgac uggcggcuug acaacugagu caaauauuucc uuacaaaggc      660
gaagacgcua cuugcaauuc caaaaagacc aauccaaaag caacuucuau uacagguuau       720
gaggauguc cgguuaauga ugagcaagca cugaugaagg caguggcaca ccaaccgguu       780
agcguuggaa uugaaggagg ugguuugau uccaauucu auucgucugg uguguucacu        840
ggagagugca cuacguaucu ugaucaugca guaacugcga uuggauacgg cgaaucuacu       900
aacgaucaa aguauuggau caucaagaau ucauggggaa caaaauggg agaaaguga         960
uauaugagga uucaaaaaga ugucaaggau aaacaaggac uauguggucu ugccaugaaa     1020
```
gcuucuuacc caacuauaug a                                                    1041

<210> SEQ ID NO 56
<211> LENGTH: 1626
<212> TYPE: RNA
<213> ORGANISM: Arabidopsis thaliana

<400> SEQUENCE: 56
auggacgauu gucgauucga gacgagugag uugcaagcuu cgguaaugau aucgacuccu    60
uuauuuaccg auucuuggag uucaugcaac accgcaaauu gcaacgggag uauaaagauc   120
caugacaucg ccgggauuac auacguugcu auaccggcgg uaucgaugau ucaguuaggg   180
aaucuugugg gcuugccagu caccggagau guucuuuucc ccggcuuauc cuccgaugaa   240
ccucuaccua uggucgacgc ugccauacuc aaacucuuuc uucaguuaaa gaucaaggaa   300
ggauuggaau uggaauuguu agguaaaaag cugguggugu uaaccggccca uucaaccggc   360 ggcgcauugg ccgcuuucac cgcacuuugg cuucuaucuc aaucuuuccc gccgucauuc   420
cgcgucuuuu guaucaccuu uggcucuccu cugcucggaa accaaucucu cuccaccuca   480
auuucacgau cacguuuagc acacaacuuc ugccacgugg ucccauccca cgaccucguu   540
ccuagaagca gcaaugaaca auucuggccc uuuggaacuu acuuguucug uuccgacaaa   600
ggaggugucu gucuagacaa cgcugguucu guucgcucga uguuuaauau ccucaacacc   660
acagcaacuc aaaacaccga ggaacaucag agguacggac acuaugeugu cacacuuuca   720 cacauguuuc uuuaaaucuag aagcuuucuu gguggagua uccccgacaa uagcuaccaa   780 gcuggguguug cguuagccgu ugaagcucua gguuucucua acgaugacac aaguggcguu   840
uuagucaaag aauguauaga aacagcuaca agaauuguuc gggcuccuau ucugaggucca   900 gcugaguuag ccaaugagcu ugcuaguguc uugccagcaa gacucgagau caauggcuac   960
aaagaucguu gcgaugcauc agaagagcag cuagguuacu acgauuucuu caaacgauau  1020
ucguugaaga gagacuuuaa agugaacaug agucgcauaa gacuagcuaa guuuuggac   1080 acagugauua aaauggugga gacgaaugag uuaccuuuug auuuucauuu aggaaagaaa   1140
uggauuuacg caucucaauu uuaucaacuc uuagccgagc cacucgacau ugcgaauuuc   1200
uacaaaaaca gagauauaaa gacuggcggg cauuacuugg aggggaauag accuaaaagg   1260
uaugagguga uugauaaaug gcagaaagga guuaaagugc cugaggagug ugugagagc   1320 agauacgcga gcacaacgca agauacuugc uuuggggcuaa gcuugagca agcaaaagag   1380 ugguggaug aggcgagaaa agagaguagu gaucccagga ggagaucuuu guuacgggaa   1440
aagauuguuc cauucgagag uuaugcgaau acauugguga cgaagaagga gguucuuug   1500 gauguuaaag cgaagaacuc gaguuauagu guguggggagg cgaacugaa agaguucaag   1560 ugcaaaaugg guuaugaaaa ugaaauugag augguuguug augagaguga cgcaauggag   1620
acuuag                                                            1626

<210> SEQ ID NO 57
<211> LENGTH: 2420
<212> TYPE: RNA
<213> ORGANISM: Arabidopsis thaliana

<400> SEQUENCE: 57
auggaagccc uccuccuccc uccuucgccg gaaccccaaa aucaaaucac caauccggcg    60
aauucaaagc caaaucauca aucggugac guacauaaag augagacgau gaugaugaag   120

```
aagaagaagg auacgaaucc aucgaauuug gaaaagagaa aacucaaggg aaagaagaaa    180
gagauuaugg acaacgacga agcuucuucg uccuauuguu cuacaucuuc uaccucuaau    240
ucaaauucua cuaaaagggu uacgagagug guucauagau uacgaaaccc uaugcgguua    300
gguauggcuc gacgaagcgu uggugaacga caagcugaaa aauuggcgaa gccucugggc    360
uuuucacuug ccgcuuuugc uaauaugguu auugcgagaa agaaugccgc aggucagaau    420
guuuauguuu augaucuugu ugagaucuuu gcuacucuug ucgaagaauc auuagccaau    480
guuuauggua auaagcuugg uuccuuugcg accaacuuug agcaaacauu cagcaguacu    540
cuaaagaucc uuaaauugac caaugaaugu gcaaauccac aucagucaaa caauaaugau    600
ggugggaguu guauuuaga ucgcucuacc auagacggau gcucagacac cgagcuauuu    660
gagagggaga cuucaucugc uacgucugcu augaaguga ugcaaggcag ugcaacagca    720
accucuuuga ugaaugagcu ugcccuuuuc gaagagacuc uacaacucuc uugugucccu    780
ccuagaaguu cagcaauggc uuugaccaca gacgaaaggu uuuaaaaga gcaaacacga    840 gcaaacgacc uaagaccgu ggagauuggu cuucaaauaa gagaguuaag gugcaaagag    900
acggcgcuag gauuaaaauu ugaaucaaac aaccggggga agcggcgcu agaguuggau    960 guuucgaaag cugcauucag agcggagaaa uucaaaaccg aauuagaaga uacaaggcaa   1020
gagauguccu aggugaaag guagcugcau ggaaagauga ugauggagau ugguaugaga   1080 cugggguugca cauauucuuu ggggcuuacc caaauaugca gaaccuguuu ggagaacuag   1140
ggauaaauga ucgguugcag uggaaggaac auucaaugau auuugcgaug ccuaacaagc   1200
caggggaguu cagccgcuuu gauuuuccug aagcucuucc ugcgccauua aauggaauuu   1260
uggccauacu aaagaacaac gaaaugcuua cguggcccga aaaagucaaa uuugcuauug   1320
gacucuugcc agcaaugcuu ggagggcaau cuuaauguga agcuaagac gguuuaagug   1380 uuaaggacug gaugagaaag caaggugugc cugauagggu gacagaugag uguucauug    1440 ccaugucaaa ggcacuuaac uucauaaacc cugacgagcu uucgaugcag ugcauuuuga   1500
uugcuuugaa cagauucuu caggagaaac augguucaaa aauggccuuu uuagauggua   1560
acccuccuga gagacuuugc augccgauug uugaacauau ugagucaaaa gguggccaag   1620
ucagacuaaa cucacgaaua aaaagauug agcugaauga ggauggaagu gucaaauguu   1680
uuauacugaa uaauggcagu acaauuaaag gagaugcuuu uguguuugcc acuccagugg   1740
auaucuucaa gcuucuuuug ccugaagagu ggaaagagau cccauauuuc caaaaguugg   1800
agaagcuagu gggagguucu gugauaaaug uccauauaug guugacaga aaacugaaga    1860 acacaucuga uaaucugcuc uucagcagaa gcccaugcu cagugugau gcugacaugu    1920 cuguuacaug uaaggaauau uacaacccca aucagucuau guggaauug guauuugcac   1980 cugcagaaga guggauaaau cguagugacu cagaaauuau ugaugcuaca augaaggaac   2040
uagcaaagcu uuucccugac gaaauuucgg cagaucagag caaagcaaaa uauugaagu    2100 aucacguugu caaaacucca aggucuguuu auaaaacugu gccagguugu gaacccuguc   2160
ggcccuugca aagaucuccu auugaggggu uuuauuagc uggugacuac acaaaacaga   2220 aauacuggc uucaauggaa ggucugucu aucaggaaa gcuuugugcc caagcuauug    2280
uacaggauua cgaguuacuu cuuggccgga gccagaagaa guuggcagaa gcaagcguag   2340
uuuagcaugg ugaacuaaaa uguugcuucu guacacuaaa uuuaagauga aggcggccac   2400
acugaauuag cguuguacac                                              2420
```

```
<210> SEQ ID NO 58
<211> LENGTH: 1614
<212> TYPE: RNA
<213> ORGANISM: Arabidopsis thaliana

<400> SEQUENCE: 58
augucaguag uuuuacucuc uucuacuucu gcaacaauca ccaaauccca auccaaaaag      60
auucccuuuu uaucucccac cacaaaauuc ccauuaaagg ucucaauuuc uccaucaaga    120
ucgaaacuuu uccacaaccc uuuacgcgug gcggcgccgc cgucuguacc cacuucggau    180
ucgacggagg agaagcggau cgaagaagaa uacggcggag auaaggaaga agaagggucu    240
gaguuuaagu ggagagauca uugguaucca guuucuuugg uugaggauuu ggauccgaau    300
gugccaaccc cguccagcu cuugggucga gaccuuguac ucugguuuga ucggaaugau    360
cagaaauggg cagccuuuga ugaucucugc ccucaccggc ucgcuccuuu aucugaagga    420
agguuggaug agaauggaca cuugcaaugu ucguaucaug gauggucauu ugguggugu     480 ggaucuugca cuaggauucc ucaggcugcu acuucagguc cugaagcucg ugcuguuaaa    540
uccccgagag cuugugcuau uaaguucccg acaauggugu cucaaggucu cucuuugug     600 uggccugaug aaaaugguug ggauagagcc aauucaauug aaccccuag guugccggau     660 gauuucgaua aaccggaauu uucgacggug acaauucaaa gggaucuuuu cuauggauau    720
gauacucuca uggaaaaugu aucugauccu ucccauauag auuuugcuca ucacaagguu    780
acaggaagaa gagacagagc caaaccauug ccguucaagg uggagucaag ugggccuugg    840
gguuuccaag gucgaauga ugacaguccá aggauaaccg caaaauuugu ugcuccgugc      900
uauucuauga acaaaauuga guuagaugcg aaacuaccaa ucgucgguaa ucaaaaaugg    960
gucauuugga uuugcucauu caauauacca auggcuccag aaagacccg uuccaucguu    1020 ugcagcgccc guaacuucuu ucaguucucu guaccaggac cagcuuggug gcagguugua   1080
ccaagauggu augaacacug gacuucgaac uuagucuaug acggagacau gaucguacuu   1140
caaggacaag agaaaguauu ccgcuaaa ucaauggagu caccagacua cgacugaac      1200 aaacaguaca caaagcucac auucacucca acccaggcag accguuuugu ucuagcauuc    1260
agaaacuggc ucagacggca ugguaagagu cagccugaau gguucggcuc caccccgucu    1320
aaccaaccuc ucccuuccac ugucuuaacc aagcgucaga ugcuagauag auuugaucag    1380
cauacacaag uaugcucuuc cugcaaagga gcuuacaaca guuccaaauu ccucaagaag    1440
uuucucguug gcgcgacggu uuucugggcc gccacggcug uguuccuuc ugauguucag      1500 auucgacugg uucuugcgg uuuaucacug auaucagcug cuucugcaua ugcuuuacau     1560
gaacaagaga agaacuuugu guuuagagau uauguacauu cugaaaucga guag          1614

<210> SEQ ID NO 59
<211> LENGTH: 2880
<212> TYPE: RNA
<213> ORGANISM: Arabidopsis thaliana

<400> SEQUENCE: 59
augaugaaga agggaaagg aaagaacagu ggcuuguuac cgaauuccuu uaagauuaua      60
ucuucuugcc uuaaaacugu aucggcuaac gccaccaacg uugcgucguc uguucguucc    120
gcuggugccu ccguugcugc uucaauuucc gcugcugaag augauaagga ucaggugacc    180
ugggcuggau uuggcauucu ugaacugggu caacaugauca ccagacaugu ucucuuacuc    240
gguuaucaga auggcuuuca agucuuugau guugaggaug cccucuaauuu uaaugaacug    300
```

-continued

```
gucucuaaac gaggugqucc aguuucauuc uuacagaugc agccauuacc ugcaaggucu    360
ggugaucaug agqquuuuug gaacucacau ccucuuuugc ugguuguugc uqqqgaugaa    420 acaaauggca cugquuuggg ucacaguuuu cccagaaug guucauuagc aagagauggu    480
aguucagacu cuaaagccgg ggaugccauc aauuauccua ccacuguucg cuucuacucc    540
cuuaggnccc acaguuaugu auaugccug agauucggu caucuguug caugauuaga      600 ugcagcuccc gaguagucgc uguuggccuu gcgaaucaaa uauauugugu ugacgcacuu    660
acucuggaaa auaaguucag guucucacu uauccuguc cccagccagu gagacaaggg     720
acaaccagag uuaauguugg cuauggnccg auggcguag guccaaggug gcuugcauau    780
gcguccaaaa guuccaugac caugaaaaca gggcgccuaa gcccacagac guuuacuucu    840
ucacccaguc ucagcccaag uucaucauca gguggaagca guuuauggc ccguuaugcc    900 auggagucua gcaagcaguu agccaaugga uuaaucaacc uggggacau gggauacaaa    960 acauugucaa aauacuguca agauaugcuc ccgauggau cuacuuccc agcaucacca    1020 aaugcaaucu ggaaaguugg uggqguuucu ggaucagaug cagagaaugc cggaaugguu   1080
gcuguuaaag aucuuguuuc uggagcuuua uaucacagu ucaaggcuca uacgagaccu   1140
aucucagcac uuuguuuuga uccuaggga acucuauugg uuacgcuuc aguauguggg    1200 aacaauauca augucuuuca gaucaugcca ucucguucac auaagcacc uggugaccua    1260 aguuaugagu gggaaucuuc ucaugugcau cuccucaaac ugcauagagg gaucacuuca    1320
gcuauugucc aggacauuug cuuuagucag cagagucagu ggguugcuau uauuucaucc    1380
aagggvacuu gccauauauu uguuuaaac ucuucggua gcgacgcugc guucaaccu     1440 ugcgagggug aggagccuac ccgacuacca gcuucauccu ugccauggug guuuacucaa    1500
ucguugucaa guaucagca gucuuuaucg ccaccaacag cuguugcccu uucguugua    1560 agcagaauaa aguauagcag uuugggugg cuuaacacag uaagcaaugc uacuacugcu    1620
gcuacuggaa aaguuuugu accaucaggu gccguggcug cuguuuucua aaaucuguc    1680 acucaugacc uucagcugaa cucccggacu aacgcguugg agcauaucuu agucuauacu    1740
ccaucaggcc augguggnca gcaugaacuu cugccaucag uuugcacaga aucaccugaa    1800
aaugguuuga gagugcaaaa aacaucacau guucaaguuc aggaggauga uuugaggguc    1860
aaaguugagc cuauucagug gugggaugua uguagaaggu cugacuggcu agagacugag    1920
gaacgacuuc ccaaaaguau cacugaaaag caauaugauu uagagacagu gucgaaucac    1980
uugacaagcc augaggaugc augucuuuc cuugacauga acagccauuu uagugaagau    2040
aaguauuuga aaagcuguuc ugagaagccc ccugaaagau cacauugcua ucuuucuaac    2100
uuugagguaa agquuaccuc ggggaugcua ccaguggge aaaauucaaa gauuucuuuu    2160
caugunaugg auucuccaag agauaguagu uccacuggug gagaguuuga gauagaaaag    2220
guuccggccc augaacuuga aauaaaacag aaaaagcugc ugccaguuuu ugaccauuuc    2280
cacagcacca aagcaacguu ggaagacagg uuuucaauga aaugcuauca cacauccgca    2340
acgggaucuc aucaaguuaa uggaaaaaua ugccaagaua uuaucaacug ucacucuaag    2400
ccaggaucaa uugagccgc cgaaaguucu gaagaggguu caacaaaaca gauggagaau    2460
cuccaugauu cggaucauau gagcaacuca aucaagucuu cuuuaccccu uuacccaaca    2520 guaaaugga cuacaagga aauagagaag aacaacgcaa auggguggau ggagaaaccc    2580
guaacagcca aacucucuac acucaaagaa acccggauca caaaugguuu uaccacacca    2640
ccuauacuca ccgauagugu caacgaacag augcucucua caggaaaacc uccuauggyc    2700
```

```
uuugguuuug cuuugcauga ggagcacugu aaagcaguag cagauccaaa agaagaacac    2760
cugaaaaaga aguuagauga aguuacuaau guucaucacu uaaacgucaa caacaacaac    2820
acagagaaac uacaaggaga caaaauggua caugguaugg uuccuuugu aggugauuaa     2880
```

<210> SEQ ID NO 60
<211> LENGTH: 21
<212> TYPE: RNA
<213> ORGANISM: Artificial Sequence
<220> FEATURE:
<223> OTHER INFORMATION: Actin 2 siRNA-A antisense strand

<400> SEQUENCE: 60
ggcaucacac uuucuacaau u                                              21

<210> SEQ ID NO 61
<211> LENGTH: 21
<212> TYPE: RNA
<213> ORGANISM: Artificial Sequence
<220> FEATURE:
<223> OTHER INFORMATION: Actin 2 siRNA-B antisense strand

<400> SEQUENCE: 61
cgagaagaac uaugaauuau u                                              21

<210> SEQ ID NO 62
<211> LENGTH: 21
<212> TYPE: RNA
<213> ORGANISM: Artificial Sequence
<220> FEATURE:
<223> OTHER INFORMATION: CHI1 siRNA-A antisense strand

<400> SEQUENCE: 62
ggagauagag gaacuggaau u                                              21

<210> SEQ ID NO 63
<211> LENGTH: 21
<212> TYPE: RNA
<213> ORGANISM: Artificial Sequence
<220> FEATURE:
<223> OTHER INFORMATION: CHI1 siRNA-B antisense strand

<400> SEQUENCE: 63
ggaacaucuu cuucugcaau u                                              21

<210> SEQ ID NO 64
<211> LENGTH: 21
<212> TYPE: RNA
<213> ORGANISM: Artificial Sequence
<220> FEATURE:
<223> OTHER INFORMATION: 18S siRNA-A antisense strand

<400> SEQUENCE: 64
gggagguagu gacaauaaau u                                              21

<210> SEQ ID NO 65
<211> LENGTH: 21
<212> TYPE: RNA
<213> ORGANISM: Artificial Sequence
<220> FEATURE:
<223> OTHER INFORMATION: 18S siRNA-B antisense strand

<400> SEQUENCE: 65
ggacgcauuu auuagauaau u                                              21

```
<210> SEQ ID NO 66
<211> LENGTH: 23
<212> TYPE: DNA
<213> ORGANISM: Artificial Sequence
<220> FEATURE:
<223> OTHER INFORMATION: Actin 2 DNA encoding siRNA-A antisense strand

<400> SEQUENCE: 66
aaggcatcac actttctaca att                                              23

<210> SEQ ID NO 67
<211> LENGTH: 23
<212> TYPE: DNA
<213> ORGANISM: Artificial Sequence
<220> FEATURE:
<223> OTHER INFORMATION: Actin 2 DNA encoding siRNA-B antisense strand

<400> SEQUENCE: 67
aacgagaaga actatgaatt att                                              23

<210> SEQ ID NO 68
<211> LENGTH: 23
<212> TYPE: DNA
<213> ORGANISM: Artificial Sequence
<220> FEATURE:
<223> OTHER INFORMATION: CHI1 DNA encoding siRNA-A antisense strand

<400> SEQUENCE: 68
aaggagatag aggaactgga att                                              23

<210> SEQ ID NO 69
<211> LENGTH: 21
<212> TYPE: DNA
<213> ORGANISM: Artificial Sequence
<220> FEATURE:
<223> OTHER INFORMATION: CHI1 DNA encoding siRNA-B antisense strand

<400> SEQUENCE: 69
aaggaacatc ttcttctgca a                                                21

<210> SEQ ID NO 70
<211> LENGTH: 23
<212> TYPE: DNA
<213> ORGANISM: Artificial Sequence
<220> FEATURE:
<223> OTHER INFORMATION: 18S DNA encoding miRNA-A antisense strand

<400> SEQUENCE: 70
aagggaggta gtgacaataa att                                              23

<210> SEQ ID NO 71
<211> LENGTH: 23
<212> TYPE: DNA
<213> ORGANISM: Artificial Sequence
<220> FEATURE:
<223> OTHER INFORMATION: 18S DNA encoding siRNA-B antisense strand

<400> SEQUENCE: 71
aaggacgcat ttattagata att                                              23
```

FORMULATIONS AND METHODS FOR CONTROL OF WEEDY SPECIES

BACKGROUND OF THE INVENTION

The present technology is directed to a formulation and a method for controlling growth of plant species. More specifically, it is a formulation comprising a targeting construct and RNAi inducer to produce small interfering RNAs for use in non-stable expression in weedy plant species. Targeting constructs are designed to target endogenous genes in the weedy species while having no effect in off-target species.

DESCRIPTION OF THE RELATED ART

The impact of invasive and pest plant species has been called an "invisible tax" on our environment and economy. With ever increasing global transportation and travel has come an unprecedented spread of invasive and noxious plant species throughout the world. These weeds adapt quickly to new environments and go largely unchallenged by local flora and fauna. Many are unreachable by or have developed resistance to conventional control techniques. Invasive species cause direct economic losses in sectors such as forestry, ranching, and agriculture.

The current strategies for invasive species management consist of the application of different combinations of chemical herbicides and physical removal, coupled with bio-control techniques as available. The available chemicals are often toxic to a wide array of native plants, animals and insects and can have negative consequences for human health. Many cannot be used in riparian or aquatic environments as the compounds would quickly spread. In addition, they have a limited half-life and efficacy and must be reapplied year after year. Bio-control and physical removal are costly and labour intensive requiring large investments and again, often resulting in collateral damage to other organisms. Some invasive pest plants are now so well established that they are widely considered impossible to remove by any available technique, for example, Eurasian Milfoil. Others, having been subjected to years of treatment with chemicals, have developed resistance to them.

In an attempt to target the species of interest and reduce the damage done by spraying with broad spectrum herbicides, U.S. Pat. No. 7,805,884 discloses an injector system for injecting a dose of weed-killing fluid into the stem of a Japanese knotweed, including a fluid dispenser system with a fluid passage, a collared needle with a fluid delivery aperture in communication with the fluid dispenser system, and an actuator connected to the fluid dispenser system for actuating the transmission of fluid from the fluid dispenser system to the fluid delivery aperture. This employs chemical herbicides.

Control of insect pests is largely through the use of chemical insecticides. Some biological control methods also exist, for example, the use of pheromones in insect traps. These are relatively labour intensive as the traps have to be baited, set and removed.

Another example of biological control is the use of *Bacillus thuringiensis* toxin. It can be provided as a spray or produced in transgenic plants. In transgenic plants, the gene or genes are expressed in the plant, the plant produces the toxin, the foraging insect ingests the plant material and is killed. One could argue that these are quasi-chemical control methods, as toxic chemicals are still being produced and used to kill the insect pests.

Rather than using toxins, U.S. Pat. No. 7,943,819 provides methods for genetic control of insect infestations in plants and compositions thereof by inhibiting one or more biological functions by feeding one or more recombinant double stranded RNA molecules to the insect pest. This reportedly results in a reduction in pest infestation through suppression of gene expression.

U.S. Pat. No. 8,148,604 discloses methods and materials for conferring insect pest resistance to plants and controlling parasitic plant pests. Plants are stably transformed with a silencing construct homologous to a gene of a plant pest that is essential for the survival, development, or pathogenicity of the pest. This results in the plant producing RNA interference (RNAi), specifically short interfering RNA (siRNA) to the selected gene, which, when ingested by the insect pest results in silencing of the gene and a subsequent reduction of the pest's ability to harm the plant. In other embodiments, the pest's reduced ability to harm the plant is passed on to pest progeny. It is also suggested that parasitic plants pests, for example striga, dodder and mistletoe can also be controlled by stably transforming plants with a silencing construct homologous to a gene of the parasitic plant that is essential for survival or development.

Without being bound by theory, RNA interference (RNAi) is considered to be an ancient defense mechanism wherein the host organism recognizes as foreign a double-stranded RNA molecule and hydrolyzes it. The resulting hydrolysis products are small RNA fragments of 21-30 nucleotides in length, called siRNAs. The siRNAs then diffuse or are carried throughout the host, where they hybridize to the complementary Viral RNA or complementary endogenous polynucleotide sequences where they act as guides for RISC mediated hydrolysis and thus knock-down or dysregulation.

For example, the different Dicer-Like proteins (DCL) of *Arabidopsis* cleave dsRNA molecules into different sized (21-25 nt) small dsRNA products depending on which DCL is processing them. *Arabidopsis* encodes 10 Argonaute proteins (AGOI-10) which bind these small RNAs and, as a part of RISC, elicit different effects depending on which AGO the small RNA has been recruited into and the size of the recruited small RNA. AGOI is largely responsible for the miRNA pathway and also post transcriptional gene silencing. The pathway it is involved in has been shown to result in both targeted degradation of mRNAs and transitivity (RNA-dependent RNA polymerase (RdRP) dependent generation of 2° siRNA products and amplification of the initial signal). It has previously been found that AGOI prefers to recruit small dsRNAs that are 21 nt in length with a 2 nt, 3' overhang on each end and will prefer sequences with a 5' terminal U as the guide strand (the strand that is responsible for guiding complementary base pairing to a target mRNA sequence) (Mi et al. 2008. Sorting of small RNAs into *Arabidopsis* Argonaute Complexes Is Directed by the 5' Terminal Nucleotide. DOI 10.1016/j.cell.2008.02.034.)

A species-specific herbicide that can be used to kill, weaken or impair growth of a weed species is needed. This is accomplished through miRNA, siRNA, DNA, or single- or double-stranded RNA designed to elicit an RNAi response that spreads systemically once inside a plant cell (RNAi Payload). The RNAi inducer elements cause the payload to be processed producing siRNAs. A region of the RNAi payload contains sequence complementary to endogenous target genes (Targeting construct). siRNAs produced from this region direct the knock-down of those genes leading to cell death. This knock-down is strengthened by RdRP mediated transitivity, phasing, and systemic spread. The result is a herbicide that can be tuned to affect any number of plant species.

SUMMARY OF THE INVENTION

The present technology provides a non-chemical herbicide that can be used to kill, weaken or impair growth of weedy species. In general, the formulation is for application to a host plant to reduce, inhibit or impair one or more of growth and development of the host plant. The formulation comprises an interfering Ribonucleic Acid (RNAi) payload, and at least one of a liquid carrier, a surfactant, a binder and tackifier, a thickener, a colourant, a spreader, an antifreezing agent, a sticker, an anticaking agent, a stabilizer, a disintegrator, an emulsifier, a synergistic compound, an abrasive, an emulsifier, a penetrating agent and a preservative.

In the formulation, the RNAi payload may comprise an at least one sequence specific to the host plant.

The RNAi payload comprises at least 20 contiguous nucleotides of at least one sequence selected from the group consisting of SEQ ID NOs 1 to 66.

The formulation may comprise an RNAi payload, the liquid carrier and the surfactant. It may further comprise the abrasive and still further comprise a synergistic compound.

The formulation is in an exemplary embodiment, for stem injection, and comprises the liquid carrier and the penetrating agent.

A method of inhibiting or impairing plant growth and development is also provided. The method comprises delivering a formulation to a host plant, by spraying, imbibing, irrigating, or injecting the formulation, the formulation comprising an interfering Ribonucleic Acid (RNAi) payload, an at least one of a liquid carrier, a surfactant, a binder and tackifier, a thickener, a colourant, a spreader, an antifreezing agent, a sticker, an anticaking agent, a stabilizer, a disintegrator, an emulsifier, a synergistic compound, an abrasive, an emulsifier, a penetrating agent and a preservative, thereby inhibiting or impairing growth and development. The method comprises delivering the formulation to at least one of a leaf, a root, a stem, a petiole, a seed and a cotyledon. The RNAi payload may comprise a sequence selected from the group consisting of SEQ ID NOs 1 to 66.

The method comprises injecting the stem or petiole or spraying the host plant.

The method further comprises inducing expression of any of SEQ ID NOs 7, 8, 9, 10, 11 and 12 thereby producing any of SEQ ID NOs 1, 2, 3, 4, 5, and 6.

A method of weed control is also provided, the method comprising:
selecting a weed plant species to be controlled;
synthesizing or obtaining at least one RNAi or RNAi encoding sequence;
formulating a species-specific RNAi payload; and
delivering the species-specific RNAi payload to the weed plant species while minimally impacting an at least one other plant species.

The RNAi payload comprises at least 20 contiguous nucleotides from or complementary to one or more of SEQ ID NOs 1 to 66.

The method may involve spraying the weed plant species or injecting the weed plant species A method of designing a species-specific construct for RNAi suppression of growth of a target plant species is also provided, the method comprising the steps of:

selecting a suitable gene for growth suppression;
identifying an at least one target site accessible to base pairing in the suitable gene; identifying an at least one divergent site in the at least one target site;
designing a construct complementary to the at least one divergent site; and
adding an at least one RNAi inducer element to the construct, thereby designing a species-specific gene construct for siRNA suppression of growth of the target plant species.

The method may further comprise adding an at least one helper sequence to the species specific gene construct.

The method may further comprise sequencing an at least one gene from the target plant to select the suitable gene.

In the method, the construct may include any one of SEQ. ID No. 1 to 66 or their complement.

A method of inhibiting or impairing plant growth and development of a target plant is also provided, the method comprising:

selecting a suitable gene for growth suppression;
identifying an at least one target site accessible to base pairing in the suitable gene; identifying an at least one divergent site in the at least one target site;
designing a construct complementary to the at least one divergent site;
adding an at least one RNAi inducer element to the construct; and
delivering the construct to the target plant.

The method may further comprise adding an at least one helper sequence to the species specific gene construct.

The method may further comprise sequencing an at least one gene from the target plant to select the suitable gene.

In the method, the construct may include any one of SEQ ID No. 1 to 66 or their complement.

Figure 1:
FIG. 1 shows a DPC targeting construct for photobleaching-based death in multiple species in accordance with an embodiment of the technology. Ath=*Arabidopsis thaliana*, Nto=*Nicotiana tobacum*, Bra=*Brassica napus*, Zma=*Zea mays*, Mtr=*Medicago truncatula*.

SEQ ID No. 46: *Arabidopsis thaliana* Lsdl sequence.

SEQ ID No. 47: *Arabidopsis thaliana* Acdll sequence.

SEQ ID No. 48: *Nicotiana sylvestris* PDS gene target construct.

SEQ ID No. 49: T7 driven RNA2 with NSYL PDS target construct in MCS.

SEQ ID No. 50: T7 driven truncated PPK20 RNA1 consisting of 5' sequence, replicase CDS, PUC57 MCS, 3' sequence, ribozyme and NOS terminator.

SEQ ID No. 51: TRV PPK20 RNA1 replicase CDS.

SEQ ID No. 52: TRV PPK20 RNA2 5' replication element containing sequence

SEQ ID No. 53: TRV Ppk20 RNA2 3' replication element containing sequence

SEQ ID No. 54: *Arabidopsis thaliana* ESR gene CDS.

SEQ ID No. 55: *Arabidopsis thaliana* SAG12 (senescence associated gene 12) CDS.

SEQ ID No. 56: *Arabidopsis thaliana* PAD4 (phytoalexin deficient 4) gene CDS.

SEQ ID No. 57: *Arabidopsis thaliana* CPR5 (constitutive expression of PR genes 5) gene CDS.

SEQ ID No. 58: *Arabidopsis thaliana* ACD1 (accelerated cell death 1) gene CDS.

SEQ ID No. 59: *Arabidopsis thaliana* ATG18 (homolog of yeast autophagy gene 18 G) gene CDS.

Additional sequences included in this application are from *Arabidopsis*. Each line provides the gene symbol, genes name and *Arabidopsis* accession number.

Starvation:

SEQ ID No. 60: HDH (HISTIDINOL DEHYDROGENASE) AT5G63890

SEQ ID No. 61: ATHMEE2 (MATERNAL EFFECT EMBRYO ARREST 2/=SHI KIMATE DEHYDROGENASE) AT3G06350

SEQ ID No. 62: ICDH (ISOCITRATE DEHYDROGENASE) AT1G54340

Early Senescence:

SEQ ID No. 63: APG 9 (AUTOPHAGY 9) AT2G31260

SEQ ID No. 64: ATG 2 (AUTOPHAGY 2) AT3G19190

SEQ ID No. 65: SRI (SIGNAL RESPONSIVE 1) AT2G22300

SEQ ID No. 66: APG7 (AUTOPHAGY 7) AT5G45900

Definitions

RNAi Payload means a payload consisting of at least one specific nucleic acid sequence or analogue sequence that, when introduced into the body of a plant, will trigger or initiate an RNAi cascade.

Cell (or host plant cell) means a cell or protoplast of a plant cell and includes isolated cells and cells in a whole plant, plant organ, or fragment of a plant. It also includes non-isolated cells.

Double stranded region means a region of a polynucleotide wherein the nucleotides or analogues are capable of hydrogen bonding to each other. Such hydrogen bonding can be intramolecular or intermolecular (e.g. single transcription unit forming a double stranded region with the so-called hairpin or two transcription units that align appropriately for complementary sequences to hydrogen bond). To be a double stranded region, according to the present invention, it is not necessary for 100% of the nucleotides to be complementary and hydrogen bonded within a region. It is merely necessary for sufficient base pairing to occur to give the RNA a substantial double stranded character (e.g. an indicative melting point).

RNAi Inducer means at least one specific nucleic acid sequence or analogue sequence that, when introduced into the body of a plant, will trigger or initiate an RNAi cascade. This can be, for example, but is not limited to DNA, dsRNA, ssRNA, siRNA, and miRNA sequences. RNAi inducers are usually capable of activating RNAi in a number of species.

Targeting constructs are added to the RNAi inducer sequence to direct the RNAi response against specific endogenous polynucleotides.

Targeting construct means a region of nucleic acid sequence that is complementary to one or more endogenous or exogenous polynucleotides. siRNAs released from the processing of a targeting construct direct RNAi machinery to knock-down endogenous polynucleotides.

RdRP means a RNA-dependent RNA polymerase. An RdRP creates a complementary strand of RNA using RNA as a template. Endogenous RdRPs include components of RISC machinery, and DNA-dependent RNA polymerases when recruited by special RNA sequences/structures. Exogenous RdRPs come from virus, retrotransposons, or are harvested from another organism.

Exogenous gene means a gene that is not normally present in a given host genome in the present form. In this respect, the gene itself may be native to the host genome, however the exogenous gene will comprise the native gene altered by the addition or deletion of one or more different regulatory elements or additional genes.

Gene or genes means nucleic acid sequences (including both RNA or DNA) that encode genetic information for the synthesis of a whole RNA, a whole protein, or any functional portion of such whole RNA or whole protein sufficient to possess a desired characteristic.

Marker gene means a gene that, when its activity is altered, imparts a distinct phenotype.

Essential gene means a gene that, when inhibited, results in a negative effect on at least one of plant growth and development. They are required for normal plant growth and reproduction.

Heterologous polynucleotide means any polynucleotide that is introduced (transiently or stably) into a non-transformed host plant. A polynucleotide is not excluded from being a heterologous polynucleotide by the presence of matching endogenous polynucleotide sequences.

Homologous means having sequence similarity sufficient to allow hybridization in vivo, in vitro, and/or ex vivo under low stringency conditions between the antisense sequence and the sense gene mRNA.

Inhibition of gene expression means a decrease in the level of protein and/or RNA product from a target gene. The consequences of inhibition can be confirmed by examination of the outward properties of the cell or organism (as presented below in the examples) or by biochemical techniques such as RNA solution hybridization, nuclease protection, Northern hybridization, polymerase chain reaction (PCR), reverse transcription (RT) reverse transcription PCR(RT/PCR), gene expression monitoring with a microarray, antibody binding, enzyme linked immunosorbent assay (ELISA), Western blotting, radioimmunoassay (RIA), other immunoassays, and fluorescence assisted cell sorting (FACS).

Substantially complementary, with respect to the sense and antisense sequences means sufficiently complementary to allow for formation of a double stranded molecule.

Transcript means RNA encoded by DNA. In the context of sense and antisense transcripts of the present invention, such sense and antisense transcripts can be part of the same polynucleotide or they can be 2 separate polynucleotides (i.e., each having its own 5' and 3' end).

Treating a weed plant means a method to cause a deleterious effect on the weed, for example, but not limited to, interfering with development, reducing growth, triggering programmed cell death such as apoptosis, senescence, or autophagy, reducing vigour, interfering with reproductive viability, or result in death.

hpRNA is hairpin RNA, produced through inverted repeats with or without a single stranded loop region.

RISC is an RNA-induced silencing complex.

dsRNA is double stranded RNA. siRNA is short interfering RNA.

miRNA is microRNA and is a small non-coding RNA molecule (ca. 22 nucleotides) found in plants and animals. They function in transcriptional and post-transcriptional regulation of gene expression.

pTRV1 and pTRV2 are well proven RNAi inducers. One skilled in the art can use other virus based sequences to create an inducer by placing the virus sequence between a suitable promoter and terminator and incorporating an MCS into it.

Weeds mean members of the Amaranthaceae family, such as green pigweed and redroot pigweed, members of the Anacardiaceae family, such as western poison-oak, central poison-ivy, eastern poison-ivy, rydberg's poison-ivy, and poison sumac, members of the Asclepiadaceae family, such as common milkweed, black dog-strangling vine, and dog-strangling vine, members of the Balsaminaceae family such as spotted jewelweed, members of the Berberidaceae family such as common barberry, members of the Boraginaceae family such as blueweed, and stickseed, members of the Caryophyllaceae family such as purple cockle, mouse-eared chickweed, bouncingbet, night-flowering catchfly, white cockle, bladder campion, corn spurry, chickweed, grass-leaved stichwort, and cow cockle, members of the Chenopodiaceae family such as Russian pigweed, lamb's quarters, *Kochia*, and Russian thistle, members of the Compositae family (Asteraceae) such as common yarrow, Russian knapweed, common ragweed, perennial ragweed, giant ragweed, stinking mayweed, common burdock, woolly burdock, absinth, biennial wormwood, mugwort, New England aster, nodding beggarticks, tall beggarticks, plumeless thistle, nodding thistle, diffuse knapweed, brown knapweed, spotted knapweed, black knapweed, chicory, Canada thistle, bull thistle, Canada fleabane, smooth hawk's-beard, narrow-leaved hawk's-beard, Philadelphia fleabane, rough fleabane, spotted Joe-Pye weed, hairy galinsoga, orange hawkweed, mouse-eared hawkweed, king devil hawkweed, spotted cat's-ear, elecampane, poverty weed, false ragweed, prickly lettuce, blue lettuce, nipplewort, fall hawkbit, ox-eye daisy, pineapple weed, scentless chamomile, black-eyed Susan, tansy ragwort, Canada goldenrod, perennial sow-thistle, spiny annual sow-thistle, annual sow-thistle, tansy, dandelion, goat's-beard, meadow goat's-beard, colt's-foot, and cocklebur, members of the Convolvulaceae family such as field bindweed, and field dodder, members of the Crassulaceae family such as mossy stonecrop, members of the Cruciferae family (Brassicaceae) such as garlic mustard, yellow rocket, hoary alyssum, Indian mustard, bird rape, small-seeded false flax, shepherd's purse, lens-podded hoary cress, hare's-ear mustard, flixweed, wood whitlow-grass, dog mustard, wormseed mustard, tall wormseed mustard, dame's-rocket, field pepper-grass, common pepper-grass, poor-man's pepper-grass, ball mustard, wild radish, creeping yellow cress, wild mustard, tumble mustard, tall hedge mustard, and stinkweed, members of the Cucurbitaceae family such as wild cucumber, members of the Cyperaceae family such as yellow nut sedge, members of the Equisetaceae family such as field horsetail, members of the Euphorbiaceae family such as three-seeded mercury, cypress spurge, leafy spurge, and hairy-stemmed spurge, members of Gramineae family (Poaceae) such as wild oats, smooth brome, downy brome, smooth crab grass, large crab grass, barnyard grass, quack grass, foxtail barley, Persian darnel, witch grass, common reed, annual blue grass, Kentucky blue grass, green foxtail, and yellow foxtail, members of the Guttiferae family such as St. John's-wort, member of the Haloragaceae family such as Eurasian water-milfoil, members of the Hydrocharitaceae family such as European frogbit, members of the Labiatae family such as ajuga, American dragonhead, hemp-nettle, ground-ivy, motherwort, catnip, heal-all, andnnarsh hedge-nettle, members of the Leguminosae family (Fabaceae) such as hog-peanut, bird's-foot trefoil, black medick, white sweet-clover, yellow sweet-clover, crown vetch, white clover, and tufted vetch, members of the Liliaceae family such as false hellebore, showy false hellebore, smooth camas, and meadow camas, members of the Lythraceae family such as purple loosestrife, members of the Malvaceae family such as velvetleaf, round-leaved mallow, and common mallow, members of the Onagraceae family such as fireweed, and yellow evening-primrose, members of the Oxalidaceae family such as European wood-sorrel, members of the Plantaginaceae family including narrow-leaved plantain, broad-leaved plantain, hoary plantain, and Rugel's plantain, members of the Polygonaceae family such as Tartary buckwheat, striate knotweed, prostrate knotweed, wild buckwheat, pale smartweed, lady's-thumb, green smartweed, sheep sorrel, curled dock, long-leaved dock, field dock, serrate-valved dock, and broad-leaved dock, members of the Pteridaceae family such as bracken, members of the Portulacaceae family such as purslane, members of the Ranunculaceae family such as tall buttercup, and creeping buttercup, members of the Rhamnaceae family such as European buckthorn, members of the Rosaceae such as silvery cinquefoil, rough cinquefoil, sulfur cinquefoil, narrow-leaved meadowsweet, and hardhack, members of the Rubiaceae family such as smooth bedstraw, members of the Scrophulariaceae family such as dwarf snapdragon, yellow toadflax, Dalmation toadflax, moth mullein, common mullein, and thyme-leaved speedwell, members of the Solanaceae family such as climbing nightshade, and eastern black nightshade, members of the Typhaceae family such as narrow-leaved cattail, and cattail, members of the Umbelliferae (Apiaceae) family such as goutweed, caraway, western water-hemlock, spotted water-hemlock, poison-hemlock, wild carrot, giant hogweed, wild parsnip, and water-parsnip, and members of the Urticaceae family such as stinging nettle.

In addition, the following weeds will be controlled, if not already listed above:

*Abutilon theophrasti* (Velvetleaf), *Acroptilon repens* (Russian Knapweed), *Aegilops cylindrica* (Jointed Goatgrass), *Agropyron repens* (Quackgrass), Alyssum, Hoary (*Berteroa incana*), *Amaranthus retroflexus* (Redroot Pigweed), *Anchusa officinalis* (Common Bugloss), Annual Bluegrass (*Poa annua*), Annual Sow-thistle (*Sonchus oleraceus*), Annual Sow-thistle, Spiny (*Sonchus asper*), *Anthriscus sylvestris* (Wild Chervil), *Arctium* spp. (Burdock), *Asclepias speciosa* (Showy Milkweed), *Avena fatua* (Wild Oats), Baby's-Breath (*Gypsophila paniculata*), Barley, Foxtail (*Hordeum jubatum*), Barnyardgrass (*Echinochloa crusgalli*), Beggar-Ticks, Nodding (*Bidens cernua*), *Berteroa incana* (Hoary Alyssum), *Bidens cernua* (Nodding Beggar-Ticks), Bindweed, Field (*Convolvulus arvensis*), Bladder Campion (*Silene cucubalus*), Bluegrass, Annual (*Poa annua*), Blueweed (*Echium vulgare*), Bog Rush (*Juncus effusus*), Broad-Leaved Plantain (*Plantago major*), Buckwheat, Tartary (*Fagopyrum tataricum*), Buckwheat, Wild (*Polygonum convolvulus*), Bugloss, Common (*Anchusa officinalis*), Bull Thistle (*Cirsium vulgare*), Burdock (*Arctium* spp.), Buttercup, Creeping (*Ranunculus repens*), Canada Thistle (*Cirsium arvense*), *Capsella bursa-pastoris* (Shepherd's-Purse), *Cardaria* spp. (Hoary Cress), *Carduus nutans* (Nodding Thistle, a.k.a. Musk Thistle), *Carduus acanthoides* (Plumeless Thistle), *Centaurea diffusa* (Diffuse Knapweed), *Centaurea pratensis* (Meadow Knapweed), *Centaurea solstitialis* (Yellow Starthistle), *Centaurea maculosa* (Spotted Knapweed), Chamomile, Scentless (*Matricaria maritima*), *Chenopodium album* (Lamb's-Quarters), *Cichorium intybus* (Chicory), *Cirsium palustre* (Marsh Plume Thistle), Chervil, Wild (*Anthriscus sylvestris*), Chicory (*Cichorium intybus*), *Chondrilla juncea* (Rush Skeletonweed), *Chrysanthemum leucanthemum* (Oxeye Daisy), *Cicuta douglasii* (Water Hemlock), Cinquefoil, Sulphur (*Potentilla recta*), *Cirsium arvense* (Canada Thistle), *Cirsium vulgare* (Bull Thistle), Cleavers (*Galium aparine*), Cluster Tarweed (*Madia glomerata*), Common Bugloss (*Anchusa officinalis*), Common Tansy (*Tanacetum vulgare*), Common Mallow (*Malva neglecta*), Common Chickweed (*Stellaria media*), *Convolvulus arvensis* (Field Bindweed), Corn Spurry (*Spergula arvensis*), Creeping Buttercup (*Ranunculus repens*), *Crupina vulgaris* (Crupina), Cudweed (*Gnaphalium uliginosunn*), Curled Dock (*Rumex crispus*), *Cytisus scoparius* (Scotch Broom), Dalmatian Toadflax (*Linaria dalmatica*), Diffuse Knapweed (*Centaurea diffusa*), Dodder, (*Cuscuta* spp.), Field Bindweed (*Convolvulus arvensis*), Field Scabious (*Knautia arvensis*), Foxtail Barley (*Hordeum jubatum*), Giant Hogweed (*Heracleum mantegazzianum*), Gorse (*Tragopogon dubius*), Green Foxtail (*Setaria viridis*), Groundsel (*Senecio vulgaris*), *Gypsophila paniculata* (Baby's-Breath), Hemp-Nettle (*Galeopsis tetrahit*), Henbit (*Lamium amplexicaule*), *Heracleum mantegazzianum* (Giant Hogweed), Himalayan Balsam (*Impatiens glandulifera*), Hoary Alyssum (*Berteroa incana*), Hoary Cress (*Cardaria* spp.), *Hordeum jubatum* (Foxtail Barley), Horsetail, Field (*Equisetum arvense*), Hound's-tongue (*Cynoglossum officinale*), *Hypericum perforatum* (St. John's-Wort), *Impatiens glandulifera* (Himalayan Balsam), Japanese Knotweed (*Polygonum cuspidatum*), Jointed Goatgrass (*Aegilops cylindrica*), *Juncus effusus* (Bog Rush), Knapweed, Meadow (*Centaurea pratensis*), Knapweed, Spotted (*Centaurea maculosa*), Knapweed, Russian (*Acroptilon repens*), Knapweed, Diffuse (*Centaurea diffusa*), *Knautia arvensis* (Field Scabious), *Kochia scoparia* (Kochia), Lady's-Thumb (*Polygonum persicaria*), Lamb's-Quarters (*Chenopodium album*), *Lamium amplexicaule* (Henbit), Leafy Spurge (*Euphorbia esula*), *Lepidium latifolium* (Perennial Pepperweed), *Linaria dalmatica* (Dalmatian Toadflax), *Linaria vulgaris* (Yellow Toadflax), *Lychnis alba* (White Cockle), *Lythrum salicaria* (Purple Loosestrife), *Madia glomerata* (Cluster Tarweed) *Malva neglecta* (Common Mallow), Marsh Plume Thistle (*Cirsium palustre*), *Matricaria maritima* (Scentless Chamomile), *Matricaria matricariodes* (Pineappleweed), Meadow Knapweed (*Centaurea pratensis*), Meadow Hawkweed (*Hieracium pilosella*), Milkweed, Showy (*Asclepias speciosa*), Mullein (*Verbascum thapsus*), Mustard, Wild (*Sinapsis arvensis*), Narrow-Leaved Plantain (*Plantago lanceolata*), Night-Flowering Catchfly (*Silene noctiflora*), Nightshade (*Solanum* spp.), Nodding Thistle, a.k.a. Musk Thistle (*Carduus nutans*), Nodding Beggar-Ticks (*Bidens cernua*), Nutsedge, Purple (*Cyperus rotundus*), Nutsedge, Yellow (*Cyperus esculentus*), *Onopordum acanthium* (Scotch Thistle), Orange Hawkweed (*Hieracium aurantiacum*), Oxeye Daisy (*Chrysanthemum leucanthemum*), *Panicum capillare* (Witchgrass), Perennial Pepperweed (*Lepidium latifolium*), Perennial Sowthistle (*Sonchus arvensis*), Pigweed, Red root (*Amaranthus retroflexus*), Pinea ppleweed (*Matricaria matricariodes*), *Plantago lanceolata* (Narrow-Leaved Plantain), *Plantago major* (Broad-Leaved Plantain), Plumeless Thistle (*Carduus acanthoides*), *Poa annua* (Annual Bluegrass), *Polygonum convolvulus* (Wild Buckwheat), *Polygonum cuspidatum* (Japanese Knotweed), *Polygonum persicaria* (Lady's-Thumb), *Potentilla recta* (Sulphur Cinquefoil), Puncture vine (*Tribulus terrestris*), Purple Nutsedge (*Cyperus rotundus*), Purple Loosestrife (*Lythrum salicaria*), Quackgrass (*Agropyron repens*), *Ranunculus repens* (Creeping Buttercup), *Rumex acetosella* (Sheep Sorrel), *Rumex crispus* (Curled Dock), Rush Skeletonweed (*Chondrilla juncea*), Russian Knapweed (*Acroptilon repens*), Russian Thistle (*Salsola kali*), Scentless Chamomile (*Matricaria maritima*), Scotch Broom (*Cytisus scoparius*), Scotch Thistle (*Onopordum acanthium*), *Senecio jacobaea* (Tansy Ragwort), Sheep Sorrel (*Rumex acetosella*), Shepherd's-Purse (*Capsella bursa-pastoris*), Sulphur Cinquefoil (*Potentilla recta*), Spotted Knapweed (*Centaurea maculosa*), St. John's-Wort (*Hypericum perforatum*), Stinkweed (*Thlapsi arvense*), Tansy Ragwort (*Senecio jacobaea*), Tartary Buckwheat (*Fagopyrum tataricum*), Tarweed, Cluster (*Madia glomerata*), Thistle, Bull (*Cirsium vulgare*), Thistle, Canada (*Cirsium arvense*), Nodding Thistle a.k.a. Musk Thistle (*Carduus nutans*), Plumeless Thistle (*Carduus acanthoides*), Russian Thistle (*Salsola kali*), Scotch Thistle (*Onopordum acanthium*), *Thlapsi arvense* (Stinkweed), Dalmatian Toadflax (*Linaria dalmatica*), Yellow Toadflax (*Linaria vulgaris*), *Tragopogon dubius* (Western Goat's-Beard), *Tribulus terrestris* (Puncture vine), *Ulex europaeus* (Gorse), Velvetleaf (*Abutilon theophrasti*), *Verbascum thapsus* (Mullein), Water Hemlock (*Cicuta douglasii*), Western Goat's-Beard (*Tragopogon dubius*), White Cockle (*Lychnis alba*), Wild Chervil (*Anthriscus sylvestris*), Wild Mustard (*Sinapsis arvensis*), Wild Buckwheat (*Polygonum convolvulus*), Wild Oats (*Avena fatua*), Witchgrass (*Panicum capillare*), Yellow Hawkweed (*Hieracium pratense*), Yellow Starthistle (*Centaurea solstitialis*), Kudzu (*Pueraria lobata*), Japanese dodder (*Cuscuta japonica*), water hyacinth (*Eichhornia* spp.) and Yellow Nutsedge (*Cyperus esculentus*).

Underlying the various embodiments of the present invention is treating a weed by introducing a heterologous polynucleotide or analogue into the weed plant, the heterologous polynucleotide comprising: 1) an RNAi inducer capable of recruiting RISC machinery to the sequence and 2) a targeting construct comprising (a) an antisense sequence having homology to an essential gene, or a marker gene, or (b) a sense sequence substantially complementary to said antisense sequence; wherein said sense and antisense sequences are capable of hybridizing to each other to form a double-stranded region.

Description:

Except as otherwise expressly provided, the following rules of interpretation apply to this specification (written description, claims and drawings): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting. Further, The terms "comprising," "having," "including," and "containing" are to be construed as open-ended terms (i.e., meaning "including, but not limited to,") unless otherwise noted.

To the extent necessary to provide descriptive support, the subject matter and/or text of the appended claims is incorporated herein by reference in their entirety.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

Overview: An RNAi payload is introduced into a host plant, for example, a weed by application of a formulation comprising the payload. Application methods include spraying, irrigating, injecting (extracellular as opposed to microinjection), abrading or otherwise causing entry of the formulation into, for example, but not limited to, a seed, a seedling, a sapling, a mature plant, a reproducing plant or a senescing plant. Application methods do not include stable transformation methods. The RNAi payload comprises one or more RNAi inducer elements encouraging its processing by dicer. The RNAi payload also contains a targeting region complementary to corresponding essential genes, or marker genes or both. When the RNAi payload is processed it releases siRNAs against those genes. The siRNAs direct RISC machinery to knock down those genes.

A list of genes used to build targeting constructs is provided. For each gene, one or more of double stranded RNA fragments and the DNA coding sequences or analogues that generate them are provided. These fragments have sequences that allow them to initiate the RNAi cascade, hence the DNA sequences will have, in addition, suitable promoters, for example, but not limited to, constitutive promoters that result in a high level of expression, and a suitable transcriptional stop element. The DNA sequences may be provided as crude viral or bacterial extracts, plasmid or viral DNA with the sequence and regulatory regions inserted therein, or may be synthesized. Each target in the targeting construct comprises at least about 19 nucleotides or at least about 50 nucleotides, or at least about 100 nucleotides, or at least about 150 nucleotides, and all sub ranges therebetween. During the knock-down process RdRPs 'transcribe' the target mRNAs. These transcripts are processed into more siRNAs targeting the whole mRNA. These are transported through the plant where they spread the cascade.

In the context of the present invention, there are three important steps to an effective RNAi herbicide. Firstly, the RNAi payload (DNA, RNA, or synthetic oligos) is delivered to the plant or part of the plant. Application methods affect delivery, with stem injection, spray, and vector-aided delivery (without stable transformation) being common techniques. Once applied, the inducer is introduced to the cytoplasm of the target cells. This may be mediated by, for example, but not limited to, additives, chemical modification of the inducer, or vectors such as viral coat protein, or nano-cages.

Secondly, a build-up of RNA occurs that can spread from cell to cell. This can happen prior to the RNAi response if exogenous RNA polymerases (such as viral RdRPs) are included as RNAi inducer elements, or if endogenous RNA polymerases (including DNA dependant RNA polymerases) are recruited to replicate the payload. It can also happen during the RNAi response if the inducer triggers RNAi-associated RdRPs. The entire inducer can be replicated, or only specific regions (using internal RNA promoters such as viral subgenomic promoters). Inducers can use one or both of these pathways for replication. Viral RNAi suppressor proteins can be included to increase the amount of RNA present before RNAi is triggered. Cell-to-cell spread can be accelerated using viral movement proteins and by targeting key plant genes.

Finally, the RNAi inducer elements elicit an RNAi response that targets RISC machinery to degrade critical endogenous RNAs. This is accomplished by complementarity between regions of the inducer and the target RNAs. Once the inducer is processed into siRNAs they are used by RISC to target further RNA. siRNAs produced from the targeting construct are complementary to endogenous target genes. These are knocked down as "Collateral damage" while the plant clears the payload.

In addition to the sequences for essential genes, the payload will include RNA fragments that will silence genes that modulate the RNAi cascade. These will be synthetic or virally derived RNA fragments targeting components of the RNAi pathway. Without being bound by theory, it is believed that the RNA payload used in the present technology will target and silence, knock-down, or dysregulate genes that are necessary for the proper growth and development and optimally, the survival of the weed.

Elements

Target genes: Apoptosis; Autophagy; Senescence; Starvation; Accessory (RISC components)

RNAi inducers: Replicase/promoter pairs; (Viral replicase and promoter/subgenomic promoter pairs; Recruitment and co-option of endogenous RNA polymerases; and Action of endogenous rdRPs [siRNA asymmetries, single base mismatches]); Recruitment of DNA ligases for RNA ligation; and that recruit dicer for RNAi processing (dsRNA regions [Inverted repeats; Hairpins; and Direct repeats])

Functional elements: Promoters; Terminators; Ribosome binding sites; Internal ribosome entry sites; Hammerhead ribozymes; Recruitment and co-option of endogenous DNA ligase to ligate RNA; and Cap stealing or RNA capping sequences.

Exogenous helper genes: Coat proteins; Movement Proteins; and RNAi suppressor proteins.

Without being bound to theory, there are three primary ways to kill plants using an RNAi cascade. The first way knocks down production of essential cellular components. This causes cells to starve, or to structurally degrade. Target genes include EPSP synthese, chalcone synthase, starch synthase, cellulose synthase, acetyl-COA reductase, transaminase, 18S rRNA, eEF-IB gamma, SAP130b, TRPT, PAI1, PDS, DGL The second way is to induce apoptotic programmed cell death by knocking out key repressors in the pathway. This results in Hypersensitive response like (HR) and necrotic lesions. It is quicker than starvation but may in some situations be too quick, killing cells before the RNAi cascade can spread. Runaway hypersensitive response can also be elicited in this manner. Target genes include BECLIN1 PI3K/VPS30 ATG3 ATG7 CAT1 ACD2, NbTCTP, LLS1.

The final way is by inducing senescence, again by knocking out key repressors of that pathway. Once senescence is triggered cells undergo a slower, more regulated cell death. Target genes to induce senescence include: APG 9 (Autophagy 9), ATG 2 (Autophagy 2), SRI (Signal responsive 1, APG7 (Autophagy 7)

Autophagy can be triggered along with any of these responses. During autophagy plant cells engulf and digest their organelles.

Helper genes include the following:

Protein coding sequences for:

- Viral movement proteins that interact with coat protein (VIGS based inducer)
- Viral movement proteins that do not require coat protein
- Viral coat proteins Production of RNA is achieved through transcription of a DNA template, either in a cell such as *E. coli* or in vitro. DNA is produced in cells, or through PCR. Promoter-polymerase combinations such at the T7 system can be used for tight control of transcription and high yield. Eukaryotic expression systems such as yeast are also viable production factories. Viral coat proteins or other protective structures may be produced in the same cells or added later to purified RNA.

The simplest RNAi inducers are siRNAs. They are recognised by RISC machinery and used directly to guide knockdown of endogenous polynucleotides. If properly formatted they also encourage endogenous RdRPs to amplify the silencing signal and cause transitivity. The siRNA sequence is also the simplest targeting construct. Longer targeting constructs can be grouped together on an RNA. Using secondary structure such as hairpins, or by transcribing both DNA strands into RNA, large dsRNA regions are created. These are recognised and processed by RISC machinery. The dsRNA replication intermediate of many virus is a trigger for RNAi, allowing many virus to act as RNAi inducers. Incorporating a targeting construct into such a virus results in a functional RNAi herbicide. Finally, single stranded RNA or DNA transcribed in plant cells can trigger RNAi if the RNA is replicated. This is achieved by including coding sequences for exogenous RdRPs, or through RNA sequences that recruit endogenous RdRPs.

Examples of the RNAi payloads used in the present technology follow and were designed to target the sequences as shown:

```
                                                SEQ ID NO: 1
Actin 2 siRNA-A (target sequence: 5'-GCATCACACTTTC
GTACAA-3');

SEQ ID NO: 2
Actin 2 siRNA-B (target sequence: 5'-CGAGAAGAACTAT
GAATTA-3');

SEQ ID NO: 3
CHLI siRNA-A (target sequence: 5'-GGAGATAGAGGAACT
GGAA-3');

SEQ ID NO: 4
CHLI siRNA-B (target sequence: 5'-GGAACATCTTCTTCT
GCAA-3');

SEQ ID NO: 5
18S siRNA-A (target sequence: 5'-GGGAGGTAGTGACAATA
AA-3');
and

SEQ ID NO: 6
18S siRNA-B (target sequence: 5'-GGACGCATTTATTAGAT
AA-3').
```

The RNAi payloads used in the present technology were designed to target the sequences as shown:

```
                                                SEQ ID NO: 7
Actin 2 siRNA-A (target sequence: 5'-GGCATCACACTTT
CTACAA-3');

SEQ ID NO: 8
Actin 2 siRNA-B (target sequence: 5'-CGAGAAGAACTAT
GAATTA-3');

SEQ ID NO: 9
CHLI siRNA-A (target sequence: 5'-GGAGATAGAGGAACTG
GAA-3');

SEQ ID NO: 10
CHLI siRNA-B (target sequence: 5'-GGAACATCTTCTTCTG
CAA-3');

SEQ ID NO: 11
18S siRNA-A (target sequence: 5'-GGGAGGTAGTGACAATA
AA-3');
and
                                                SEQ ID NO: 12
18S siRNA-B (target sequence: 5'-GGACGCATTTATTAGAT
AA-3').
```

Design: For the target genes, siRNAs were designed with reference to the literature, the target site accessibility web tool, RNAxs (http://rna.tbi,unjvie.ac.at/cgi-bin/RNAxs?hakim-1) and BLAST searches.

The genes chosen were essential genes or marker genes, which, when knocked down would be expected to provide an easily identifiable phenotype.

The first siRNAs were designed to be incorporated into Argonaute protein (AGOI). They were 21 nt in length with a UU, 3' overhang on each end and a 5' terminal U. A 5' phosphate was added to the guide strand of the siRNA.

Other designs include one or more of targeting different AGO complexes, using a different 5' nucleotide, using chemically modified siRNA to increase stability, using different 3' overhang nucleotides, and including a 5' phosphate on both strands.

As the mRNA target site should be accessible, the RNAxs webserver was used to search through a given mRNA sequence and identify those sites based on the 2° structure of the mRNA and thermodynamic asymmetry and folding energies associated with the siRNAs themselves.

siRNA means "small interfering RNA" which are also commonly referred to as "short interfering RNA" or alternatively as "silencing RNA".

Details of the process used to produce targeting constructs in *Nicotiana sylvestris* were as follows (this process applies to designing targeting constructs for any plant): Target gene mRNAs were run through the RNAxs program using standard settings.

- The top 20-25 hits (lowest "worst rank") were mapped to the original mRNA sequence
  - When available, homologous mRNA sequences from other *N. sylvetris* (or *Solanacea* spp. or *Arabidopsis thaliana*) were also run through RNAxs and have their highest 20-25 hits mapped.
  - The homologues were then aligned to compare the regions of highest effective siRNA target concentration.
  - For the present technology, regions with numerous "good" targets that also have perfect (or at most 2 mismatches in a stretch of 21 nt) sequence identity to the *N. sylvetris* sequence were sought.
  - *N. sylvetris* was used as the reference sequence for all targets, therefore the whole construct had perfect sequence identity to *N. sylvestris*.
- Regions of effective targets were cut from the original mRNA sequence to make smaller target regions of various lengths (21-120 nt). The 18-24 nt regions can be used directly as siRNA constructs (which have both RNAi inducer and targeting construct activity). Otherwise, the process to build longer, multi-gene targeting constructs is as follows:
  - Sequences complementary to the most accessible mRNA regions were pulled out were trimmed to remove intervening sequences where no effective siRNAs are predicted.
  - Multiple trimmed segments were joined together to make an approx. 120 nt targeting cluster that consist of 10s of predicted high-effectiveness siRNAs targeting a gene of interest.

Other considerations included that the target sites should not cover splice junctions or start or stop codons and should avoid sites of single nucleotide polymorphisms between sequenced transcript variants.

Longer RNAi payloads require RNAi inducer elements to induce the processing of the payload into siRNAs. These mostly involve the production of a dsRNA region in the RNAi payload.

Synthesis: For using siRNAs directly as RNAi payloads the selected siRNAs were synthesized chemically. A 5' phosphate was added to the guide strand of the siRNA.

Longer RNAi payloads are transcribed from DNA, either in vitro, in plantae, or in another organism such as *Escherichia coli*. The DNA sequences encoding longer RNAi payloads may also be synthesized or produced using standard cloning techniques and PCR, or a combination of both.

DNA production: The selected DNA encoding the RNAi payloads were cloned using standard cloning techniques, in, for example, but not limited to a replication system in *E. coli*, using vectors that comprise, for example, but are not limited to, pBR322, pUC series, M13 mp series, pACYC184, etc., and pCAMBIA 1201. The DNA sequence was inserted into the vector at a suitable restriction site. The resulting plasmid was used for transformation into *E. coli*. The *E. coli* cells were cultivated in a suitable nutrient medium, then harvested, lysed and optionally lyophilize and used directly, or the plasmid was recovered and used as such, or the specific sequence and the promoter and the transcription stop were recovered and used.

There are a wide number of promoters that can be employed, including constitutive inducible, and tissue or temporally specific promoters. Plant promoters include but are not limited to ribulose-l,6-bisphosphate (RUBP) carboxylase small subunit (ssu), beta-conglycinin promoter, beta-phaseolin promoter, ADH promoter, heat-shock promoters, the enhanced Ca MV 35S promoter and tissue specific promoters.

Transcription stops include but are not limited to nopaline synthase (NOS) gene transcription stop, the Cauliflower mosaic virus (CaMV) 35S gene transcription stop, and the Rubisco small subunit (SSU) gene transcription stop.

Those skilled in the art will be aware of additional promoter sequences and terminator sequences suitable for use in performing the invention. Such sequences may readily be used without any undue experimentation.

Embodiments of the present invention are taught herein where it is desirable to have more than one terminator. Examples of such are embodiments are where the sense and antisense sequences are to be contained on separate transcripts (i.e. each having its own 3' and 5' end).

Delivery: The RNAi payloads are delivered to the weed as a formulation by spraying, irrigating, injecting, or abrading a seedling, a sapling, a mature plant, a reproducing plant or a senescing plant. Both the stem and the petiole will be injected. Leaves will be specifically targeted in addition to delivering the formulation to the entire plant. Seeds will also treated by dipping or imbibition. Roots will be treated by irrigation.

In addition to the RNAi payload, accessory targeting constructs, and helper genes, the formulations include any or all of a liquid carrier, a surfactant, a binder and tackifier, a thickener, a colourant, a spreader, an antifreezing agent, a sticker, an anticaking agent, a stabilizer, a disintegrator, an emulsifier, a synergistic compound, an abrasive, an emulsifier, a penetrating agent and a preservative.

The liquid carrier includes, for example, alcohols including monohydric alcohols such as methanol, ethanol, propanol, isopropanol, butanol and the like and polyhydric alcohols such as ethylene glycol, diethylene glycol, propylene glycol, hexylene glycol, poly(ethylene glycol), poly(propylene glycol), glycerol and the like; polyhydric alcohol-based compounds such as propylene glycol ether and the like; ketones such as acetone, methyl ethyl ketone, methyl isobutyl ketone, diisobutyl ketone, cyclohexanone and the like; ethers such as ethyl ether, dioxane, ethyleneglycol monoethyl ether, dipropyl ether, tetrahydrofuran and the like; aliphatic hydrocarbons such as normal paraffins, naphthenes, isoparaffins, kerosenes, minerals oil and the like; aromatic hydrocarbons such as benzene, toluene, xylene, solvent naphtha, alkylnaphthalenes and the like; halogenated hydrocarbons such as dichloroethane, chloroform, carbon tetrachloride and the like; esters such as ethyl acetate, diisopropyl phthalate, dibutyl phthalate, dioctyl phthalate, dimethyl adipate and the like; lactones such as gamma-butyrolactone and the like; amides such as dimethylformamide, diethylformamide, dimethylacetamide, N-alkylpyrrolidinone and the like; nitriles such as acetonitrile and the like; sulfur compounds such as dimethyl sulfoxide and the like; vegetable oils such as soybean oil, rapeseed oil, cottonseed oil, castor oil and the like; water; and so on. These can be used singly or can be used as a combination of two kinds or more.

The penetrating agents include dimethyl sulphoxide (DMSO), Azone (1-dodecylazacycloheptan-2-one or laurocapran), N-methyl-2-pyrolidone, glycols (diethylene glycol and tetraethyleneglycol), fatty acids (lauric acid, myristic acid, oleic acid and capric acid), terpenes such as the essential oils of eucalyptus, *chenopodium* and ylang-ylang, sesquiterpenes, polyethylene glycol (PEG) and L-menthol.

The surfactant includes, for example, nonionic surfactants such as sorbitan fatty acid esters, polyoxyethylene sorbitan fatty acid esters, sucrose fatty acid esters, polyoxyethylene fatty acid esters, polyoxyethylene resinate esters, polyoxyethylene fatty acid diesters, polyoxyethylene alkyl ethers, polyoxyethylene alkylphenyl ethers, polyoxyethylene dialkyl phenyl ethers, polyoxyethylene alkyl phenyl ether-formalin condensate products, polyoxyethylene-polyoxypropylene block copolymers, alkyl polyoxyethylene-polypropylene block polymer ethers, polyoxyethylenealkylamines, polyoxyethylene fatty acid amides, polyoxyethylene fatty acid bisphenyl ethers, polyalkylene benzyl phenyl ethers, polyoxyalkylene styrylphenyl ethers, acetylene diols, polyoxyalkylene-added acetylene diols, polyoxyethylene ether-type silicones, ester-type silicones, fluorine surfactants, polyoxyethylene castor oils, hydrogenated polyoxyethylene castor oils and the like; anionic surfactants such as alkyl sulfate salts, polyoxyethylene alkyl ether sulfate salts, polyoxyethylene alkyl phenyl ether sulfate salts, polyoxyethylene styryl phenyl ether sulfate salts, alkylbenzenesulfonate salts, lignin sulfonate salts, alkylsulfosuccinate salts, naphthalenesulfonate salts, alkylnaphthalene sulfonate salts, salts of formalin condensate products of naphthalene sulfonic acid, salts of formalin condensate products of alkylnaphthalene sulfonic acid, fatty acid salts, polycarboxylate salts, N-methyl-fatty acid sarcosinate, resinates, polyoxyethylene alkyl ether phosphate salts, polyoxyethylene alkyl phenyl ether phosphate salts and the like; cationic surfactants such as laurylamine hydrochloride salts, stearylamine hydrochloride salts, oleylamine hydrochloride salts, stearylamine acetate salts, stearylaminopropylamine acetate salts, alkylamine salts including alkyltrimethylammonium chloride and alkyldimethylbenzalkonium chloride and the like; ampholytic surfactants such as amino acid type- or betaine type-surfactants and the like; and so on. These surfactants can be used singly or can be used as a combination of two kinds or more.

The binder and tackifier include, for example, carboxymethylcellulose and a salt thereof, dextrin, water-soluble starch, xanthan gum, guar gum, sucrose, poly(vinylpyrrolidone), gum arabic, polyvinyl alcohol), polyvinyl acetate), sodium polyacrylate, poly(ethylene glycol) with an average molecular weight of 6000 to 20000, polyethylene oxide with an average molecular weight of 100000 to 5000000, phospholipid (for example, cephalin, lecithin and the like) and so on.

The thickener includes, for example, water-soluble polymers such as xanthan gum, guar gum, carboxymethylcellulose, poly(vinylpyrrolidone), carboxyvinyl polymers, acrylic polymers, starch-based compounds and polysaccharides; inorganic fine powders such as high-purity bentonite and fumed silica (white carbon); and the like.

The colourant includes, for example, inorganic pigments such as iron oxide, titanium oxide, and Prussian blue; organic dyes such as an alizarin dye, azo dye, and metal phthalocyanine dye; and the like.

The spreader includes, for example, silicone-based surfactants, cellulose powders, dextrin, modified starch, a polyaminocarboxylic acid chelate compound, crosslinked poly(vinylpyrrolidone), a copolymer of maleic acid with a styrene compound, a (meth)acrylic acid copolymer, a half ester of a polymer composed of polyhydric alcohol with dicarboxylic anhydride, a water-soluble salt of polystyrenesulfonic acid and the like.

The sticker includes, for example, paraffin, terpene, a polyamide resin, polyacrylate, polyoxyethylene, wax, polyvinyl alkyl ether, an alkylphenol-formalin condensate product, a synthetic resin emulsion and the like.

The antifreezing agent includes, for example, polyhydric alcohols such as ethylene glycol, diethylene glycol, propylene glycol, glycerol and the like, and so on.

The anticaking agent includes, for example, polysaccharides such as starch, alginic acid, mannose, galactose and the like; poly(vinylpyrrolidone), fumed silica (white carbon), ester gum, a petroleum resin and the like.

The disintegrator includes, for example, sodium tripolyphosphate, sodium hexametaphosphate, metal stearates, a cellulose powder, dextrin, a methacrylate copolymer, poly (vinylpyrrolidone), a polyaminocarboxylic acid chelate compound, a sulfonated styrene-isobutylene-maleic anhydride copolymer, a starch-polyacrylonitrile graft copolymer and the like.

The stabilizer includes, for example, desiccants such as zeolite, calcined lime, magnesium oxide and the like; antioxidants such as phenol compounds, amine compounds, sulfur compounds, phosphoric acid compounds and the like; ultraviolet absorbers such as salicylic acid compounds, benzophenone compounds and the like; and so on.

The preservative includes, for example, potassium sorbate, 1,2-benzthiazolin-3-one and the like.

The abrasives include carborundum, silica, calcium oxalate, microbeads, nanobeads, nanoparticles and the like.

In a number of cases it is advantageous to add emulsifiers to the formulation. A first preferred group of emulsifiers encompasses non-ionic surfactants such as, for example: products of the addition of 2 to 30 mol ethylene oxide and/or 0 to 5 mol propylene oxide onto linear or branched, saturated or unsaturated C. sub.8-22 fatty alcohols, onto C. sub.12-22 fatty acids and onto alkyl phenols containing 8 to 15 carbon atoms in the alkyl group; C. sub.12/18 fatty acid monoesters and diesters of addition products of 1 to 30 mol ethylene oxide onto glycerol; glycerol mono- and diesters and sorbitan mono- and diesters of saturated and unsaturated fatty acids containing 6 to 22 carbon atoms and ethylene oxide addition products thereof; addition products of 15 to 60 mol ethylene oxide onto castor oil and/or hydrogenated castor oil; polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable; addition products of 2 to 15 mol ethylene oxide onto castor oil and/or hydrogenated castor oil and/or other vegetable oils; partial esters based on linear, branched, unsaturated or saturated C. sub.6/22 fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose); mono-, di and trialkyl phosphates and mono-, di- and/or tri-PEG-alkyl phosphates and salts thereof; wool wax alcohols; polysiloxane/polyalkyl polyether copolymers and corresponding derivatives; mixed esters of pentaerythritol, fatty acids, citric acid and fatty alcohol and/or mixed esters of C. sub.6-22 fatty acids, methyl glucose and polyols, preferably glycerol or polyglycerol, polyalkylene glycols and alkyl and glycerol carbonates.

The formulation may be prepared as a mixture with components other than those listed above, such as, for example, another herbicide, a plant growth regulator, a fertilizer and the like. It is proposed that these adjuvants would increase the efficacy of the treatment or would have a synergistic effect.

When the aforementioned additional ingredient is contained in the formulation, a content thereof is selected in the range of, on a mass basis, usually 5 to 95% or, preferably, 20 to 90% as a carrier, usually 0.1 to 30% or, preferably, 0.5 to 10% as a surfactant, and 0.1 to 30% or, preferably, 0.5 to 10% as other additional ingredients.

The formulation can be employed as prepared in any desired formulations including liquid formulations, emulsifiable concentrates, wettable powders, dust formulations, oil solutions, water dispersible granules, flowable, emulsion waters, granules, jumbo formulations, suspended-emulsions, microcapsules and others.

FIG. 1 shows a DPC targeting construct for photobleaching-based death in multiple species in accordance with an embodiment of the technology. Ath=*Arabidopsis thaliana*, Nto=*Nicotiana tobacum*, Bra=*Brassica napus*, Zma=*Zea mays*, Mtr=*Medicago truncatula*.

Figure 2:
FIG. 2 shows an apoptosis targeting construct for *Brassica rapa* in accordance with an embodiment of the technology. Inserted into vector for *E. coli* production or transcribed in vitro. Resultant dsRNA is applied to plants.

FIG. 2 shows an apoptosis targeting construct for *Brassica rapa* in accordance with an embodiment of the technology. Inserted into vector for *E. coli* production or transcribed in vitro. Resultant dsRNA is applied to plants.

Figure 3:
FIG. 3 shows an apoptosis targeting construct 2, for *Nicotiana sylvestris* in accordance with an embodiment of the technology. sgP=subgenomic promoter. Cloned into RNA2-MCS vectors or co-expressed with TRV replicase.

FIG. 3 shows an apoptosis targeting construct 2, for *N. sylvetris* in accordance with an embodiment of the technology. sgP=subgenomic promoter. Cloned into RNA2-MCS vectors or co-expressed with TRV replicase.

Figure 4:
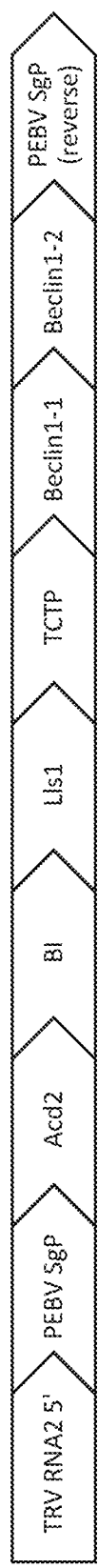
FIG. 4 shows an apoptosis targeting construct 3, for *Nicotiana sylvestris* inside TRV RNA2 in accordance with an embodiment of the technology. RNA applied to plants along with TRV RNA1.

FIG. 4 shows an apoptosis targeting construct 3, for *N. sylvetris* inside TRV RNA2 in accordance with an embodiment of the technology. RNA applied to plants along with TRV RNA1.

Figure 5:
FIG. 5 shows a T7-driven helper construct in accordance with an embodiment of the technology. RNA is added directly to plants, or cloned into RNA2-MCS or RNA1-MCS vectors.

FIG. 5 shows a T7-driven helper construct in accordance with an embodiment of the technology. RNA added directly to plants, or cloned into RNA2-MCS or RNA1-MCS vectors.

Figure 6:
FIG. 6 shows an empty VIGS-based vector to produce coated RNA1 and 2 based RNAi inducers in *E. coli* in accordance with an embodiment of the technology. Targeting constructs such as FIG. 3 are cloned into the MCS contained in RNA2, usually with flanking subgenomic promoters.

FIG. 6 shows an empty VIGS-based vector to produce coated RNA1 and 2 based RNAi inducers in *E. coli* in accordance with an embodiment of the technology. Targeting constructs such as FIG. 3 are cloned into the MCS contained in RNA2, usually with flanking subgenomic promoters.

Figure 7:
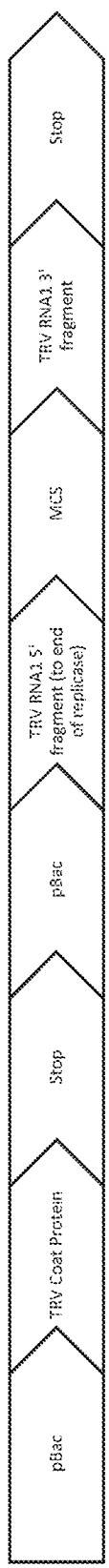
FIG. 7 shows an empty VIGS-based vector to produce coated RNA1 and 2 based RNAi inducers in accordance with an embodiment of the technology. Targeting constructs such as FIG. 3 are cloned into the MCS contained in RNA2, usually with flanking subgenomic promoters.

FIG. 7 shows an empty VIGS-based vector to produce coated RNA1 and 2 based RNAi inducers in accordance with an embodiment of the technology. Targeting constructs such as FIG. 3 are cloned into the MCS contained in RNA2, usually with flanking subgenomic promoters.

Figure 8:
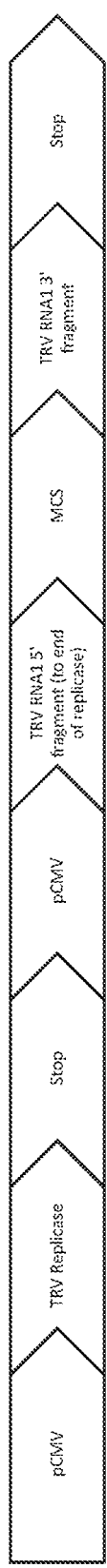
FIG. 8 shows an empty VIGS-based vector to produce coated RNA1 and 2 based RNAi inducers in yeast in accordance with an embodiment of the technology. Targeting construct is cloned into the MCS contained in RNA2, usually with flanking subgenomic promoters.

FIG. 8 shows an empty VIGS-based vector to produce coated RNA1 and 2 based RNAi inducers in yeast in accordance with an embodiment of the technology. A targeting construct is cloned into the MCS contained in RNA2, usually with flanking subgenomic promoters.

Figure 9:
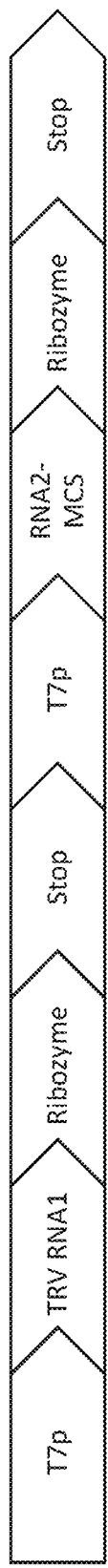
FIG. 9 shows an empty VIGS-based vector to produce naked TRV RNA1 and RNA2 based RNAi inducers in accordance with an embodiment of the technology. Functional in *E. coli* with T7 Polymerase and for in vitro production. Ribozymes cleave the RNA into separate strands.

FIG. 9 shows an empty VIGS-based vector to produce naked TRV RNA1 and RNA2 based RNAi inducers in accordance with an embodiment of the technology. Functional in *E. coli* with T7 Polymerase and for in vitro production. Ribozymes cleave the RNA into separate strands.

Figure 10:
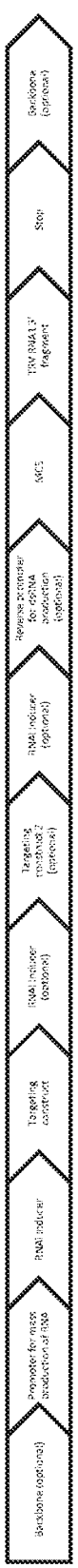
FIG. 10 shows a generic model of a DNA construct for an RNAi herbicide. The core of the herbicide is the targeting construct, tuned to affect one or a few plant species. RNAi inducer elements are either inserted into the targeting sequence (introns to make hairpins, direct or inverted repeats with/without base pairing mismatches), or are inserted around the targeting construct (subgenomic, viral, or endogenous RdRP promoters). This is all driven by either single or flanking promoters for RNA production in the chosen production species, and a circular or linear backbone for maintaining the construct in the production species.

FIG. 10 shows a generic model of a DNA construct for an RNAi herbicide. The core of the herbicide is the targeting construct, tuned to affect one or a few plant species. RNAi inducer elements are either inserted into the targeting sequence (introns to make hairpins, direct or inverted repeats with/without base pairing mismatches), or are inserted around the targeting construct (subgenomic, viral, or endogenous RdRP promoters). This is all driven by either single or flanking promoters for RNA production in the chosen production species, and a circular or linear backbone for maintaining the construct in the production species.

Figure 11:
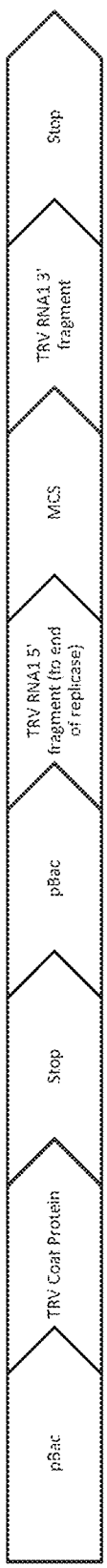
FIG. 11 shows a construct for producing an RNAi herbicide in *E. coli*, without a target construct. In bacteria the TRV coat protein is transcribed and translated. Targeting constructs are inserted into the MCS. The TRV RNA1 fragments facilitate coating of the RNA. In SEQ ID No. 45: *Nicotiana benthamiana* NbTCTP mRNA for translationally controlled tumor protein sequence.

FIG. 11 shows a construct for producing an RNAi herbicide in *E. coli*, without a target construct. In bacteria the TRV coat protein is transcribed and translated. Targeting constructs are inserted into the MCS. The TRV RNA1 fragments facilitate coating of the RNA. In target plants this RNA is transcribed to produce viral replicase, which produces dsRNA from the entire RNA. This induces the RNAi response.

Treatment: By way of example, suitable exemplary treatments are outlined as follows:

Example 1

SEQ ID NO: 3 will be used to treat *Medicago truncatula* seeds by imbibition. This sequence targets the gene for the CHLI subunit of magnesium chelatase (SULFUR gene). Seeds will be imbibed in a solution containing SEQ ID NO: 3 and siRNA targeting AGO6. The results will show that the seedlings, and more specifically, the cotyledons will be chlorotic in comparison to the controls.

Example 2

SEQ ID NO: 1 will be used to treat *Arabidopsis thaliana plants*, by abrading the leaves and delivering a solution of SEQ ID NO: 1, a surfactant, and siRNA targeting AG06. This sequence targets the Actin 2 gene. The results will show that the leaves senesce more rapidly than those of the controls.

Example 3

SEQ ID NO: 1 will be used to treat *Arabidopsis thaliana* plants, by abrading the leaves and applying a solution of SEQ ID NO: 1 and a surfactant. This sequence targets the Actin 2 gene. The results will show that the leaves senesce more rapidly than those of the controls.

Example 4

SEQ ID NO: 2 will be used to treat *Arabidopsis thaliana* plants, by spraying the leaves with a solution of SEQ ID NO: 2, an abrasive and a surfactant. This sequence targets the Actin 2 gene. The results will show that the leaves senesce more rapidly than those of the controls.

Example 5

SEQ ID NO: 4 will be used to treat *Medicago truncatula* plants, by injecting the stem or petiole with a solution of SEQ ID NO: 2, 2,4-Dichlorophenoxyacetic acid (2,4-D) DMSO and siRNA targeting AG06. SEQ ID NO: 4 targets the gene for the CHLI subunit of magnesium chelatase. The results will show that the leaves become chlorotic more rapidly and to a greater extent than those of the controls. Similarly, the leaves will become chlorotic more rapidly and to a greater extent than those treated with the formulation of Example 1. Without being bound to theory, it is expected that there is a synergistic effect caused by the combination of the siRNA and the 2,4-D.

Example 6

SEQ ID NO: 2 will be used to treat *Physcomitrella patens*, by spraying the moss with a solution of SEQ ID NO: 2 and a surfactant. SEQ ID NO: 4 targets the Actin 2 gene. The results will show that the moss senesces more rapidly than those of the controls.

Example 7

SEQ ID NO: 5 will be used to treat *Medicago truncatula* plants by irrigating the roots with a solution of SEQ ID NO: 5. SEQ ID NO: 5 targets the 18S ribosomal RNA gene. The results will show that the plants senesce more rapidly than the controls.

Example 8

SEQ ID NO: 8 will be used to treat *Arabidopsis thaliana* seeds by coating the seeds prior to imbibition. The formulation will include a sticker such as a terpene or wax or a tackifier such as xanthan gum. SEQ ID NO: 8 targets the 18S ribosomal RNA gene. The results will show that the seedlings senesce, whereas the controls do not.

Example 9

Other sequences will be synthesized and tested. The following functions and genes will be targeted:
Regulating water content (Lock stomata open or closed)
Targets: Effectors that open stomata, Regulators of effectors that open/close stomata.
Gene: ABI1 (AT4G26080) (component of negative feedback loop in abscisic acid (ABA) signalling).
Result: Without being bound to theory, stomata stay closed contributing to the overall damage to the plant and forcing it to retain water.

Example 10

Deregulate Starch Breakdown
Targets: Starch synthesis genes and Repressors of starch breakdown genes (repressors of amylases).
Gene: ADP-glucose pyrophosphorylase (At5g48300).
Result: Without being bound to theory, increased concentration of simple sugars which will affect the energy state of the plant, alter the direction and volume of phloem transport, and make it more accessible to saprotrophs and other organisms.

Example 11

Gene targets that will limit the effectiveness of the RNAi cascade.
Targets: DCLs, AGOs, other RISC components etc.
Gene: AGO6 (AT2G32940)
Result: Without being bound to theory, a subset of sRNA processing is ablated altering regulation across the plant and increasing the relative number of available intracellular RISC components.

Example 12

Limit ability of plasmodesmata to close (lock them open via an effector or an element from a component of the blue light response pathway).
Targets: Effectors that close plasmodesmata, or repressors of effectors that open plasmodesmata
Gene: Cadmium-ion induced glycine rich protein cdiG RP homologues, an effector that closes plasmodesmata.

Result: Without being bound to theory, plasmodesmata will tend to be open thus maximizing the ability of the RNAi cascade to spread through the plant.

Example 13

Deregulate Cell Wall Modifying Enzymes

Targets: Repressors of cell wall modifying enzymes—specifically enzymes that break down main, load bearing and protective components of the cell wall (expansins, cellulases, proteases, glycoside hydrolases etc.). Gene: DREB binding factor homologues: an effector that negatively regulates leaf elongation.

Result: Without being bound to theory, in addition to contributing to the overall damage (lethality) to the plant, this will also make the plant matter easier to degrade by saprotrophs and other organisms.

Example 15

SEQ ID No. 13 is cloned into SEQ ID No. 28. DNA is grown in *E. coli* and then purified. *Arabidopsis thaliana, Brassica rapa, Medicago truncatula, Zea mays*, and *Nicotiana* leaves are treated with the resultant DNA. In all plants the result will be death through loss of chlorophyll production and chlorophyll degradation (photobleaching).

Example 16

SEQ ID No. 14 is cloned in between T7 promoters in a standard vector. DNA is grown in *E. coli* expressing T7 polymerase or transcribed in vitro. The resulting dsRNA is purified and applied directly to *Brassica rapa* subsp. *pekinensis*. Treated plants will undergo systemically spreading hypersensitive-response like cell death.

Example 17

SEQ ID No. 15 DNA is cloned into the MCS of the T7-RNA2-MCS inducer as shown in sequence ID No 26. The resultant DNA along with the T7-RNA1 inducer are transcribed in vitro. The resulting naked RNAs are applied directly to *Nicotiana sylvestris*. Viral replicase increases the amount of RNAi inducer and targeting construct present. Viral coat proteins and movement proteins initiate the systemic spread of the targeting construct before the RNAi response begins. Treated plants die from necrotic/HR-like lesions.

Example 18

T7 promoter driven RNA2 containing Seq ID NO 15 flanked by sgPs and T7 promoter driven RNAl are prepared and used on *Nicotiana sylvestris* as above. The subgenomic promoter sequences flanking the targeting construct cause it to be replicated by itself, further increasing the amount of targeting construct present before the RNAi response.

Example 19

A targeting construct flanked with sgPs is cloned into the MCS in FIG. 7. The resulting DNA is then cloned into a standard vector and grown in *E. coli*. Transcription results in production of coat protein mRNA and RNAl containing a targeting construct. Translation of the coat protein in *E. coli* results in monomers that recognise elements of the TRV RNAl sequences, coating the entire RNA. This adds stability and increases ease of transmission to target plants. Once inside the target plant, replicase is produced from the TRV RNA1 fragment, replicating the entire fragment as well as producing dsRNA of the targeting construct.

Example 20

SEQ ID No. 13 is flanked by subgenomic promoters and cloned into the TRV1 RNA1 fragment MCS of an RNAi inducer construct. Treatment of the above plants with the RNA produced will result in photobleaching of chloroplasts and resultant plant death through energy starvation.

Example 21

SEQ ID No. 14 is cloned in original and inverted orientation into an RNAi GG vector. This results in a hairpin with the two sequences separated by an intron. Treatment of plants with this DNA vector produces the hairpin RNA which is processed into siRNAs targeting the 5 endogenous genes. Treated plants die from spreading necrotic lesions as runaway apoptosis is initiated.

Example 22

SEQ ID No. 15 was cloned into the MCS of SEQ ID 18. The resulting DNA is delivered directly to plants along with a helper construct encoding a replicase (SEQ ID No. 17) Endogenous promoters transcribe the initial RNA, replicase is translated, and the construct RNA is replicated. Treated *Nicotiana sylvestris* die from runaway HR-associated apoptotic cell death.

Example 23

SEQ ID No. 16 was cloned into the MCS of SEQ ID 18. The resulting DNA is delivered directly to plants along with a helper construct encoding a replicase (SEQ ID No. 17) Endogenous promoters transcribe the initial RNA, replicase is translated, and the construct RNA is replicated. Treated *Nicotiana sylvestris* die from runaway HR-associated apoptotic cell death.

Example 24

SEQ ID No. 17 is a helper construct. Plants are treated with this helper construct DNA (linear or in a vector) in addition to a RNA2-MCS RNAi inducer containing a targeting construct (SEQ ID No. 13). Treated plants undergo photobleaching and death through energy starvation. SEQ id 17 contains elements such as replicase to produce dsRNA in plant cells.

Example 25

SEQ ID No. 18 is used to clone targeting construct (SEQ ID No. 16) directly. The resulting DNA is delivered directly to plants along with a helper construct encoding a replicase (SEQ ID No. 17) Endogenous promoters transcribe the initial RNA, replicase is translated, and the construct RNA is replicated. Treated *Nicotiana sylvestris* die from runaway HR-associated apoptotic cell death.

Example 26

SEQ ID No. 19 and SEQ ID No. 23 are transcribed in vitro (this DNA is used to produce TRV RNA1 RNA in *E. coli* or in vitro). The resulting RNAs are delivered directly to plants with carborundum abrasive. Treated plants die from runaway HR like apoptotic cell death.

Example 27

SEQ ID No. 20 is co-transformed into *E. coli* containing inducible T7 polymerase along with a plasmid containing a targeting construct flanked with RNA1 or 2 3' and 5' sequences and driven by T7 promoter (SEQ ID No. 21 containing SEQ ID No. 16 in the MCS). Upon induction the coat protein is translated and coats the two RNAs when they are transcribed. The resulting coated RNAs are delivered directly to plants. Treated plants exhibit a runaway HR-like apoptotic cell death phenotype.

Example 28

SEQ ID 16 is cloned into the MCS of SEQ ID No. 21. The product thereof is co-transformed into *E. coli* containing inducible T7 polymerase along with SEQ ID No. 20. Upon induction the coat protein is translated and coats the two RNAs when they are transcribed. The resulting coated RNAs are delivered directly to plants. Treated plants exhibit a runaway HR-like apoptotic cell death phenotype.

Example 29

SEQ ID No. 22 and SEQ ID 20 are transcribed in vitro using the T7 polymerase system. Coat protein from SEQ ID No. 20 isn't produced. The two RNAs that are produced are applied directly to *N. sylvestris*. Treated plants die from runaway HR like necrotic cell death.

Example 30

SEQ ID No. 23 and SEQ ID No. 20 are transcribed in vitro. Coat protein is not produced in vitro. Plants treated with the two RNAs die from runaway HR like necrotic cell death. The addition of the subgenomic promoter increases the amount of RNA produced in plant cells. This strengthens the RNAi signal.

Example 31

SEQ ID No. 15 is cloned into SEQ ID No. 24. The resultant sequence and SEQ ID 20 are transcribed in vitro. Coat protein is not produced in vitro. Plants treated with the two RNAs die from runaway HR like necrotic cell death. The addition of flanking subgenomic promoters results in the production of dsRNA of just the targeting construct region in addition to replication of the entire RNA. This strengthens the RNAi signal.

Example 32

SEQ ID No. 26 along with RNA produced from SEQ ID No. 23 is delivered directly to *N. sylvetris* with carborundum abrasive. Treated plants die from runaway HR like apoptotic cell death.

Example 33

SEQ ID No. 27 is cloned into the MCS of SEQ ID No. 24. The resultant sequence and SEQ ID No. 20 are transcribed in vitro. Coat protein is not produced in vitro. Plants treated with the two RNAs die from runaway HR like necrotic cell death. The addition of flanking subgenomic promoters results in the production of dsRNA of just the targeting construct region in addition to replication of the entire RNA. This strengthens the RNAi signal.

Example 34

SEQ ID No. 15 is cloned into SEQ ID No. 28 using BsaI sites. Plants treated with the resultant DNA transcribe a large hairpin RNA from it. This is processed into siRNAs that induce runaway HR like necrotic cell death.

Example 35

SEQ ID No. 29 is used to treat plants. Plants treated with this DNA transcribe a large hairpin RNA from it. This is processed into siRNAs that induce runaway HR like necrotic cell death.

Example 36

SEQ ID No. 30 will be used to drive transcription of RNAi herbicide components in eukaryotic platforms.

Example 37

SEQ ID No. 31 will be used in conjunction with full length TRV derived RNAs or RNA flanked with TRV RNA 3' and 5' ends. The protein produced coats such RNAs, protecting them and increasing the likelihood of them reaching plant tissues.

Example 38

SEQ ID No. 32 will be used in conjunction with full length TRV derived RNAs or RNA flanked with TRV RNA 3' and 5' ends. The protein produced coats such RNAs, protecting them and increasing the likelihood of them reaching plant tissues. Codon optimization has been used to create a sequence for optimal translation in *E. coli*.

Example 39

SEQ ID No. 33 will be used in helper constructs. The protein produced suppresses RNAi temporarily in planta. This allows initial RNA elements time to replicate and reach a higher concentration before being processed by RNAi machinery.

Example 40

SEQ ID No. 34 will be incorporated in a plant expressible helper construct and DNA or RNA delivered directly to plants. It will lessen and slow the spread of the RNAi cascade.

Example 41

SEQ ID No. 35 will be incorporated into a plant-expressible helper construct and DNA or RNA applied directly to plant. It will aid in the spread of RNAs before RNAi is activated.

Example 42

SEQ ID No. 36 will be used to find homologues in other species. It is also a target gene used to build target constructs. Knockdown of this gene will result in autophagy.

Example 43

SEQ ID No. 37 will be used to find homologues in other species. It is also a target gene used to build target constructs. Knockdown of this gene will cause apoptosis.

Example 44

SEQ ID No. 38 will cause apoptosis. It is a target gene used to build target constructs. It will also be used to find homologues in other species.

Example 45

SEQ ID No. 39 It is a target gene used to build target constructs. It will also be used to find homologues in other species.

Example 46

SEQ ID No. 40 It is a target gene used to build target constructs. It will also be used to find homologues in other species.

Example 47

SEQ ID No. 41 It is a target gene used to build target constructs. It will also be used to find homologues in other species.

Example 48

SEQ ID No. 42 It is a target gene used to build target constructs. It will also be used to find homologues in other species.

Example 49

SEQ ID No. 43 It is a target gene used to build target constructs. It will also be used to find homologues in other species.

Example 50

SEQ ID No. 44 It is a target gene used to build target constructs. It will also be used to find homologues in other species.

Example 51

SEQ ID No. 45 It is a target gene used to build target constructs. It will also be used to find homologues in other species.

Example 52

SEQ ID No. 46 It is a target gene used to build target constructs. It will also be used to find homologues in other species.

Example 53

SEQ ID No. 47 It is a target gene used to build target constructs. It will also be used to find homologues in other species.

Example 54

*Nicotiana sylvestris* was chosen as the target weed. *Medicago truncatula* was chosen as the non-target plant. The sequences for both species are publically available. Genes from the target list that act as negative regulators of apoptosis were selected and the *Nicotiana sylvestris* homologues were run through RNAxs. The most accessible sequence regions were compared to homologous stretches of *Medicago truncatula* genes to confirm divergence. Suitable sequences were incorporated into SEQ ID No. 15. This construct was then cloned into the MCS of SEQ ID No. 21 in an *E. coli* backbone (pUC57). SEQ ID No. 20 was also cloned into the *E. coli* backbone. *E. coli* containing inducible T7 polymerase was transformed with this construct. Transformed *E. coli* were grown up, spun down, lysed, and the lysate rubbed onto plants with carborundum. The lysate contains RNA1 and 2 from TRV, with the targeting construct inside the MCS of RNA2. These RNAs are coated with viral coat protein. Treated plants undergo spreading apoptotic cell death similar to a runaway hypersensitive response. Without being bound to theory, this is because replicase is produced from the TRV RNA1, which replicates both RNAs. This increases RNA concentration. Viral movement proteins aid in the spread of intact RNAs. Eventually the dsRNA replication intermediaries are recognized by RISC machinery and processed into siRNAs. The siRNAs produced from the targeting construct induce the knock-down of Atg5, Catl, Jazh, MC2, and Beclinl. This tips the plant cell's regulatory machinery toward hypersensitive response. siRNAS produced from the targeting construct, as well as phased siRNAs produced from RdRP replication of target mRNAs by RISC machinery, are transported throughout the plant, spreading the phenotype. Treating *Medicago truncatula* did not affect the plant because processing of the targeting construct does not result in siRNAs targeting endogenous genes.

Example 55

SEQ ID No. 13 is a target construct generated as follows: The CHLI1 gene in *Arabidopsis* was used to find homologues in *Brassica rapa, Medicago truncatula, Zea mays,* and *Nicotiana tobacum*. These sequences were searched for regions accessible by RISC machinery using RNAxs. The best regions from each homologue were incorporated into the target construct. This construct was then cloned into the MCS of SEQ ID No. 21 in an *E. coli* backbone (pUC57). SEQ ID No. 20 was also cloned into the *E. coli* backbone. *E. coli* containing inducible T7 polymerase was transformed with this construct. Transformed *E. coli* were grown up, spun down, lysed, and the lysate rubbed onto plants with carborundum. The lysate contains RNA1 and 2 from TRV, with the target construct inside the MCS of RNA2. These RNAs are coated with viral coat protein. Replicase is produced from the TRV RNA1, which replicates both RNAs. Without being bound to theory, this increases RNA concentration. Viral movement proteins aid in the spread of intact RNAs. Eventually the dsRNA replication intermediaries are recognizes by RISC machinery and processed into siRNAs. The siRNAs produced from the targeting construct induce the knock-down of CHLI1. Plant growth is retarded, sometimes fatally, as damaged photosystems are not repaired. Off target plants are unaffected.

Example 56

A helper construct is constructed from SEQ IDs 33, 34 and 35. Sequences are driven by the T7 promoter producing polycistronic RNA. IRES elements are used to ensure translation in plant tissues. This is inserted into the MCS of SEQ ID No. 18. This along with SEQ ID No. 22 is transcribed in vitro. The resulting RNAs are applied directly to plants. Treated plants exhibit runaway HR-like apoptotic cell death. The 30 kda movement protein and the HCpro proteins aid in the movement of the unprocessed RNAs. The P19 protein suppresses the RNAi response until the RNAs have moved further from the application site.

Example 57

A targeting construct was designed to induce senescence in *Nicotiana sylvestris*. Genes from the senescence gene list were used to identify homologues of APG-9, ATG 2, SRI, and APG7 in *N. sylvestris*. These were run through RNAxs to identify RISC accessible regions. Sequences complementary to the most accessible regions were strung together to make the targeting construct RNA. DNA encoding this RNA is cloned into the MCS of SEQ ID No. 18. This and SEQ ID No. 17 are cloned into a binary vector maintained in plants and *E. coli*. The resulting construct is replicated and purified from *E. coli*, and the DNA applied directly to plants. In the plant the DNA is transcribed. The resultant RNAs are directly replicated after replicase is translated from RNA1. Treated plants undergo spreading senescence which eventually overwhelms them. As senescence takes a while to develop after induction, the signal has time to spread through the plant.

Example 58

A targeting construct was designed to starve cells of amino acids. Genes from the starvation list were used to identify homologues of HDH, AthMee2, and ICDH in *N. sylvestris*. These were run through RNAxs to identify RISC accessible regions. Sequences complementary to the most accessible regions were strung together to make the targeting construct RNA. DNA encoding this RNA is cloned into the MCS of SEQ ID No. 18. This and SEQ ID No. 17 are cloned into a binary vector maintained in plants and *E. coli*. The resulting construct is replicated and purified from *E. coli*, and the DNA delivered directly to plants. In the plant the DNA is transcribed. The resultant RNAs are directly replicated after replicase is translated from RNA1. Processing of these RNAs by RISC machinery leads to loss of production of a number of amino acids. Plants die due to being unable to replace degraded or damaged proteins.

Example 59

SEQ ID No. 48 is a target construct generated as follows: The *Arabidopsis* PDS gene was used to find the homologue in *Nicotiana sylvestris*. These sequences were searched for regions accessible by RISC machinery using RNAxs. The best regions containing no perfect matches to *Medicago truncatula* were incorporated into the target construct. DNA encoding this RNA is cloned into the MCS of SEQ ID 18. This and SEQ ID No. 17 are cloned into a binary vector maintained in plants and *E. coli*. The resulting construct is replicated and purified from *E. coli* and the DNA applied directly to plants. In the plant the DNA is transcribed. The resultant RNAs are directly replicated after replicase is translated from RNA1. Processing of the targeting construct results in siRNAs that knock down Phytoene desaturase. Plants turn white and plant growth is retarded, sometimes fatally, as damaged photosystems are not repaired. Off target plants such as *Medicago truncatula, Arabidopsis thaliana* and *Beta vulgaris* are unaffected.

Example 60

SEQ ID No. 49 is DNA containing TRV RNA2 loaded with the *Nicotiana sylvestris* anti-PDS targeting construct. This, along with SEQ ID No. 19 are used to produce RNAs in Vitro with T7 polymerase. The resulting RNAs are applied directly to plants. The RNAs are directly replicated after replicase is translated from RNA1. Processing of the targeting construct results in siRNAs that knock down Phytoene desaturase. Plants turn white and plant growth is retarded, sometimes fatally, as damaged photosystems are not repaired. Off target plants such as *Medicago truncatula, Arabidopsis thaliana* and *Beta vulgaris* are unaffected.

Example 61

SEQ ID No. 32 is used in conjunction with full length TRV derived RNAs or RNA flanked with TRV RNA 3' and 5' ends. The protein produced coats such RNAs, protecting them and increasing the likelihood of them reaching plant tissues. Codon optimization has been used to create a sequence for optimal translation in *E. coli*.

Example 62

The generalized steps for controlling a weed species are as follows:
Selecting a weed plant species to be controlled;
Sequencing genes from the target list in the weed and in non-target neighbor plants;
Designing a targeting construct complementary to accessible regions of target genes that are divergent in off-target plants;
Incorporating the target construct into an effective RNAi inducer;
Adding helper components as required to increase silencing efficiency and spread;
Producing the DNA or RNA to apply to plants;
Formulating the DNA or RNA for optimum penetration into plant tissues; and
Delivering the formulated DNA or RNA to plants.

Example 63

SEQ ID No. 48 was examined and found to have 0 off-target perfect matches in *Medicago truncatula, Brassica napus, Arabidopsis thaliana, Beta vulgaris, Gossypium* spp. and *Oryza sativa.*

Example 64

An accessory targeting construct was built targeting AB1, ADP-glucose pyrophosphorylase, AG06, cdiGRP, and DREB binding factor homologues in *Nicotiana sylvestris*. These were run through RNAxs to identify RISC accessible regions. Sequences complementary to the most accessible regions were strung together to make the targeting construct RNA. DNA encoding this RNA is cloned into the MCS of SEQ ID No. 19 (T7 RNA1) and applied in conjunction with SEQ ID No. 49: (T7 driven RNA2 with Nsyl PDS targeting construct in MCS). RNA from these sequences was produced in vitro using the T7 system. Treated plants turn white and plant growth is retarded, sometimes fatally, as damaged photosystems are not repaired. ABI1 knock-down will cause stomata to stay closed contributing to the overall damage to the plant and forcing it to retain water. ADP-glucose pyrophosphorylase knock-down will cause increased concentration of simple sugars which will affect the energy state of the plant, alter the direction and volume of phloem transport, and make it more accessible to saprotrophs and other organisms. AGO6 knockdown will ablate a subset of small RNA processing, freeing RISC machinery to process endogenous gene targets. cdiGRP knock-down will keep plasmodesmata open even during conditions of stress, increasing the rate of spread of the RNAi cascade. Knock-down of homologues of DREB binding factor caused unregulated leaf elongation, including increasing production of cell-wall degrading enzymes such as expansins. This contributes to the overall damage of the plant.

Example 65

The process for creating a RNAi herbicide against a specific species is as follows.

1. Obtain sequence data for target species
   a. Publically available,
   b. If no sequence data is available use PCR to amplify regions corresponding to genes in target list. Have those PCR fragments sequenced.
2. Select target regions based on RNA accessibility,
3. Obtain sequence data for other plants in area where herbicide will be applied a. Use public data where available, otherwise PCR and sequence as in 1.

4. Search for target region sequences with no more than 18 nt sequential complementarity to non-target plants.
   a. And preferably less than 18 nt complementarity or none.
5. Assemble 2 or more (usually at least 5) target regions into a targeting construct
6. Add an RNAi inducer to the targeting construct
   a. Replicase/promoter pairs
   b. Secondary structure elements (bulges, single base mismatches outside of core region, hairpins and inverted repeats)
7. Chose the most appropriate RNA production method
   a. In planta
      i. Construct flanked with plant expression promoters (CaMV35 for example) DNA added to plants.
   b. In prokaryotes
      i. Add prokaryotic promoters (one or flanking promoters) to produce single or double stranded RNA.
      ii. Add coating elements from virus (such as TRV) and co-express construct with bacterially translated coat protein.
   c. In other eukaryotes
      i. Same as i for prokaryotes
      ii. Express VIGS based RNAs along with viral replicase
         1. Results in production of coated RNAs containing construct
   d. In vitro Certain elements enhance the systemic spread of RNAi. Mismatched base pairs in the stem region of a dsRNA are a powerful way to ensure the derived siRNAs trigger RdRP activity at their targets. Mismatches at the 5" end of the siRNA are not tolerated. Moving from the 5' to the 3' end, mismatches become better tolerated. Using endogenous miRNA generating sequences such as tasi-RNA as backbones also aids in systemic spread.

Without being bound to theory, there are two reasons why the process described in this patent is generalizable to all known plant species. First, due to the degenerate nature of the genetic code there are many sequence level differences between species in genes that code for identical proteins. Because RNAi requires at least 18 nt of sequence complementarity (usually 21 nt) it is relatively easy to find stretches of RNA that are different in the target species and its neighbors. A single mismatch is usually sufficient to prevent knock-down in off-target plants. Sequences with 2 or more mismatches to off-target plants are sought to ensure knock-down does not occur. Plants can develop resistance to a specific targeting construct through mutation. The likelihood of developing enough spontaneous mutations in all the target genes simultaneously however is low. Even if resistance emerges those individuals can be sequenced and used to produce a new targeting construct.

Secondly, the core RISC machinery is highly conserved and RNAi is critical for defense against virus and pathogenic sequence elements. In order to develop resistance to this process a plant would have to shut down this response. Those plants would be highly susceptible to disease preventing them from gaining a foothold in the population.

List of potential genes of interest for use in this technology:

Essential Gene Targets 3-phosphoshikimate 1-carboxyvinyltransferase (EPSP synthase) AT2G45300

Chalcone synthase (CHS) AT5G13930

Starch synthase (SSI) AT5G24300

Starch synthase 3 (SS3) AT1G11720

Cellulose synthase 1 (CESA1) AT4G32410

Cellulose synthase 8 (CESA8) AT4G18780

Histidinol dehydrogenase (HDH) AT5G63890

Maternal effect embryo arrest 2/Shikimate dehydrogenase (AthMEE2) AT3G06350

Isocitrate dehydrogenase (ICDH) AT1G54340

Hydroxyl methylglutaryl coA reductase 1 (HMG1) AT1G76490

Pyruvate dehydrogenase El alpha subunit (PDH-E1 ALPHA) AT1G01090

Branched chain amino acid transaminase 1 (BCAT1) AT1G10060

Branched chain amino acid transaminase 2 (BCAT2) AT1G10070

18s ribosomal RNA (18S rRNA) 1005246134

Eukaryotic elongation factor (eEF-IB beta) AT1G30230

Spliceosome associated protein 130b (SAP130b) AT3G55220

2' tRNA phosphotransferase (TRPT) AT2G45330

Phosphoribosylanthranilate isomerase 1 (PAI1) AT1G07780

Phytoene desaturase (PDS) AT4G14210

Dongle (DGL) AT1G05800

Apoptosis Gene Targets

Beclin 1 (BECLIN1) AT3G61710

Bax inhibitor 1 (BI-l) JX481914

Phosphatidylinositol 3-kinase (PI3K/VPS30) AT1G60490

Lesion simulating disease 1 (LSD1) AT4G20380

Accelerated cell death 1 (ACD1) AT3G44880

Autophagy related protein 3 (ATG3) AT5G61500

Autophagy related protein 7 (ATG7) AT5G45900

Accelerated cell death 11 (ACD11) AT2G34690

Catalase 1 (CAT1) HF564631.1

Accelerated cell death 2/Putative red chlorophyll catabolite reductase (ACD2) EU294213.1

Translationally controlled tumor protein (NbTCTP) AB780363.1

Jasmonate ZIM domain protein h (JazH) JQ172766.1

Lethal leaf spot 1-like (LLS1) AF321984.1

Metacaspase 2 (MCS) AT4G25110

Senescence and Autophagy

Target of rapamycin (TOR) AT1G50030

Autophagy 9 (APG9) AT2G31260

Autophagy 2 (ATG2) AT3G19190

Autophagy 5 (ATG5) AT5G17290

Signal responsive 1 (SRI) AT2G22300

Autophagy 7 (APG7) AT5G45900

Senescence associated gene (SAG12) AT5G45890

Phytoalexin deficient (PAD4) AT3G52430

Constitutive expression of PR genes 5 (CPR5) AT5G64930

Homologue of yeast autophagy gene 18 (ATG18) AT1G03380

Helper Elements

Tobacco mosaic virus 30 kDa movement protein, V01408.1

Papaya Ringspot virus HCpro peptide, JX448373.1

Tomato bushy stunt virus P19 suppressor, AJ288943.1

Inducers pTRV2, AF406991.1 pRNAi-GG, JQ085427.1

TRV Ppk20 RNA1, AF314165.1

All methods described herein can be performed in any suitable order unless otherwise indicated herein or otherwise clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Advantages of the exemplary embodiments described herein may be realized and attained by means of the instrumentalities and combinations particularly pointed out in this written description. It is to be understood that the foregoing general description and the following detailed description are exemplary and explanatory only and are not restrictive of the claims below. While example embodiments have been described in detail, the foregoing description is in all aspects illustrative and not restrictive. It is understood that numerous other modifications and variations can be devised without departing from the scope of the example embodiment. For example, other genes may be targeted, such as chloroplast and mitochondrial nuclear encoded genes, trafficking and translocation signal sequences, energy metabolism genes, high level regulatory sequences, regulators of cellulases and cell-wall remodelling enzymes and regulators of apoptosis.

What is claimed is:

1. A RNAi payload construct comprising the nucleotide sequences set forth in SEQ ID NO:22, SEQ ID NO:23, SEQ ID NO:27 and SEQ ID NO:29.

* * * * *